United States Patent
Tufaro et al.

(10) Patent No.: US 10,238,698 B2
(45) Date of Patent: Mar. 26, 2019

(54) BIOMARKERS AND COMBINATION THERAPIES USING ONCOLYTIC VIRUS AND IMMUNOMODULATION

(71) Applicants: DNA TRIX, INC., Houston, TX (US); MD ANDERSON CANCER CENTER, Houston, TX (US)

(72) Inventors: Frank Tufaro, Rancho Santa Fe, CA (US); Charles Conrad, Spring, TX (US); Juan Fueyo-Margareto, Houston, TX (US); Frederick Lang, Jr., Houston, TX (US); Candelaria Gomez-Manzano, Houston, TX (US); W. K. Alfred Yung, Houston, TX (US); Amy Heimberger, Houston, TX (US)

(73) Assignees: DNATRIX, INC., Houston, TX (US); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/374,619

(22) PCT Filed: Jan. 25, 2013

(86) PCT No.: PCT/US2013/023304
§ 371 (c)(1),
(2) Date: Jul. 25, 2014

(87) PCT Pub. No.: WO2013/112942
PCT Pub. Date: Aug. 1, 2013

(65) Prior Publication Data
US 2014/0377221 A1 Dec. 25, 2014

Related U.S. Application Data

(60) Provisional application No. 61/590,441, filed on Jan. 25, 2012, provisional application No. 61/637,191, filed on Apr. 23, 2012.

(51) Int. Cl.

| | |
|---|---|
| *G01N 33/53* | (2006.01) |
| *A61K 35/761* | (2015.01) |
| *G01N 33/574* | (2006.01) |
| *A61K 38/20* | (2006.01) |
| *A61K 38/21* | (2006.01) |
| *C07K 16/28* | (2006.01) |
| *A61K 45/06* | (2006.01) |
| *A61K 39/395* | (2006.01) |
| *C12N 7/00* | (2006.01) |
| *A61K 39/00* | (2006.01) |

(52) U.S. Cl.
CPC .......... *A61K 35/761* (2013.01); *A61K 38/208* (2013.01); *A61K 38/2013* (2013.01); *A61K 38/217* (2013.01); *A61K 39/3955* (2013.01); *A61K 45/06* (2013.01); *C07K 16/28* (2013.01); *C07K 16/2818* (2013.01); *C12N 7/00* (2013.01); *G01N 33/57484* (2013.01); *G01N 33/57488* (2013.01); *A61K 2039/505* (2013.01); *C07K 2317/21* (2013.01); *C07K 2317/76* (2013.01); *C12N 2710/10033* (2013.01); *C12N 2710/10332* (2013.01); *G01N 2333/52* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,677,178 | A | 10/1997 | McCormick |
| 5,801,029 | A | 9/1998 | McCormick |
| 5,846,782 | A | 12/1998 | Wickham et al. |
| 5,856,181 | A | 1/1999 | McCormick |
| 6,080,578 | A | 6/2000 | Bischoff et al. |
| 6,096,718 | A | 8/2000 | Weitzman et al. |
| 6,403,370 | B1 | 6/2002 | Alemany et al. |
| 6,455,498 | B1 | 9/2002 | Vogelstein |
| 6,740,525 | B2 | 5/2004 | Roelvink et al. |
| 6,756,044 | B1 | 6/2004 | Roelvink et al. |
| 6,824,771 | B1 | 11/2004 | Curiel et al. |

(Continued)

FOREIGN PATENT DOCUMENTS

| | | |
|---|---|---|
| CN | 101607985 | 12/2009 |
| EP | 2383577 | 11/2011 |

(Continued)

OTHER PUBLICATIONS

Lee et al (Clin Cancer Res, 2006, 12(19): 5859-5868).*
Jarnagin et al (Cancer Gene Therapy, 2003, 10: 215-223).*
Senzer et al (Journal of Clinical Oncology, 2009, 27(34): 5763-5771).*
Alonso et al (Molecular Therapy, 2008, 16(3): 487-493).*
Jiang et al (PLOS One, 2014, 9(5): e97407).*
Terando et al (Cancer Immunol Immunother, 2003, 52: 680-685).*
Su et al (Journal of Clinical Oncology, 2004, 22(4): 610-616).*
Kim et al (Immunology, 2007, 122: 615-622).*
Curran et al (PNAS, 2010, 107(9): 4275-4280).*
Tockman et al (Cancer Res., 1992, 52:2711s-2718s).*
Yong et al (Cancer Research, 2009, 69(23): 8932-8940).*

(Continued)

*Primary Examiner* — Sean E Aeder
(74) *Attorney, Agent, or Firm* — Parker Highlander PLLC

(57) ABSTRACT

The invention disclosed herein describes biomarkers useful for prognosis, selection and monitoring of oncolytic virus therapy for patients with various types of cancer. In particular, the present invention provides identification of proteins whose expression patterns are strongly predictive of the outcome of oncolytic virus therapy in a patient with cancer. The present invention provides a method for identifying and selecting cancer patients who are likely to be non-responsive to onocolytic virus therapy. These patients can be co-administered an agent that stimulates a cell-mediated immune response in the patient with the oncolytic virus or can be administered a therapy other than oncolytic virus therapy.

6 Claims, 7 Drawing Sheets

(56) References Cited

U.S. PATENT DOCUMENTS

| | | | |
|---|---|---|---|
| 8,168,168 | B2 | 5/2012 | Fueyo et al. |
| 2003/0138405 | A1 | 7/2003 | Fueyo et al. |
| 2004/0175362 | A1 | 9/2004 | Curiel et al. |
| 2006/0147420 | A1 | 7/2006 | Fueyo et al. |
| 2007/0141028 | A1 | 6/2007 | Hamada et al. |
| 2009/0155282 | A1 | 6/2009 | Weber et al. |
| 2012/0207711 | A1 | 8/2012 | Fueyo et al. |
| 2013/0071403 | A1* | 3/2013 | Rolland ........... A61K 39/39558 424/142.1 |
| 2014/0227226 | A1 | 8/2014 | Fueyo-Margareto et al. |
| 2014/0377294 | A1 | 12/2014 | Fueyo-Margareto et al. |

FOREIGN PATENT DOCUMENTS

| | | |
|---|---|---|
| EP | 2407177 | 1/2012 |
| JP | 2003-501445 | 1/2003 |
| JP | 2009-504687 | 2/2009 |
| WO | WO 96/17053 | 6/1996 |
| WO | WO 96/34969 | 11/1996 |
| WO | WO 98/39467 | 9/1998 |
| WO | WO 00/29599 | 5/2000 |
| WO | WO 00/56909 | 9/2000 |
| WO | WO 00/67576 | 11/2000 |
| WO | WO 00/75292 | 12/2000 |
| WO | WO 01/23004 | 4/2001 |
| WO | WO 01/28569 | 4/2001 |
| WO | WO 2003/087319 | 10/2003 |
| WO | WO 2005/094867 | 10/2005 |
| WO | WO 2007/025365 | 3/2007 |
| WO | WO 2009/1117656 | 9/2009 |
| WO | WO 2010/072900 | 7/2010 |
| WO | WO 2010/135242 | 11/2010 |
| WO | WO 2011/134670 | 11/2011 |
| WO | WO 2011/140284 | 11/2011 |
| WO | WO 2013/076374 | 5/2013 |
| WO | WO 2013/116778 | 8/2013 |
| WO | WO 2014/204814 | 12/2014 |

OTHER PUBLICATIONS

Gruber et al (Am J Clin Oncol, 2004, 27: 33-38).*
Ge et al (Clinical Developmental Immunology, 2010, 19 pages).*
Alonso et al (Cancer Res, 2007, 67(24): 11499-11504).*
Weinberg et al (Journal of Immunology, 2000, 164: 2160-2169).*
Nettelbeck et al (Cancer Research, 2002, 62: 4663-4670).*
Quirt et al (The Oncologist, 2007, 12(9): 1114-1123).*
Brahnner et al (Journal of Clinical Oncology, 2010, 28(19): 3167-3175).*
Alonso et al., "Adenovirus-based strategies overcome temozolomide resistance by silencing the O6-methylguanine-DNA methyltransferase promoter ," Cancer Res, 67(24): 11499-504, 2007.
Office Communication issued in corresponding New Zealand Application No. 627736, dated Aug. 26, 2016.
Jarnagin et al., "Neoadjuvant treatment of hepatic malignancy: an oncolytic herpes simplex virus expressing IL-12 effectively treats the parent tumor and protects against recurrence-after resection ," Cancer Gene Therapy, 10: 215-223, 2003.
Kim et al., "Enhanced antitumour immunity by combined use of temozolomide and TAT-survivin pulsed dendritic cells in a murine glioma" Immunology, 122: 615-622, 2007.
Office Communication issued in corresponding Chinese Application No. 201380010639.1, dated Jul. 5, 2016.
Cascallo et al. (2007). "Systemic toxicity-efficacy profile of ICOVIR-5, a potent and selective oncolytic adenovirus based on the pRB Pathway." Mol Therapy 15(9): 1607-15.
Hedley et al. (2006) Targeted and Shielded Adenovectors for Cancer Therapy. Cancer Immunol. Immunother. 55, 1412-1419.
Hedley et al. (2009) Assessment of genetic shielding for adenovirus vectors. Open Gene Therapy J., 2, 1-11.
Kaliberov, S. A., L. N. Kaliberova, et al. (2013). "Retargeting of gene expression using endothelium specific hexon modified adenoviral vector." Virology 447(1-2): 312-25.

Kurihara et al. (2000). Selectivity of a replication-competent adenovirus for human breast carcinoma cells expressing the MUC1 antigen. J. Clin. Invest., 106(6), 763-771.
Mathis et al. (2011) Genetic incorporation of human metallothionein into the adenovirus protein IX for non-invasive SPECT imaging. PLOS One. 6(2), e16792.
Office Communication issued in corresponding European Application No. 13706770.8, dated Nov. 28, 2016.
Piao et al. (2009). "Oncolytic adenovirus retargeted to delta-EGFR induces selective antiglioma activity." Cancer Gene Ther. 16(3): 256-265.
Worgall et al. (2004). Modification to the capsid of the adenovirus vector that enhances dendritic cell infection and transgene-specific cellular immune responses. J Virol, 78(5), 2572-2580.
Worgall et al. (2005). Protection against P. aeruginosa with an adenovirus vector containing an OprF epitope in the capsid. J Clin Invest, 115(5), 1281-1289.
Wu H. T. Han, et al. (2005). "Identification of sites in adenovirus hexon for foreign peptide incorporation." J Virol 79(6): 3382-90.
Adachi Y, et al., "A midkine promoter-based conditionally replicative adenovirus for treatment of pediatric solid tumors and bonemarrowtumorpurging," Cancer Res., 61(21): 7882-8, 2001.
Alemany et al., "CAR-binding ablation does not change biodistribution and toxicity of adenovirus vectors," Gene Therapy, 8: 1347-1353, 2001.
Alemany, R., et al., "Gene Therapy for Gliomas: Molecular Targets, Adenoviral Vectors, and Oncolytic Adenoviruses," Exp. Cell. Res., 252: 1-12, 1999.
Alemany, R., et al., "Growth inhibitory effect of anti-K-ras adenovirus on lung cancer cells," Cancer Gene Therapy, 3(5): 296-301, 1996.
Alonso et al., "Delta-24-RGD in combination with RAD001 induces enhanced anti-glioma effect via autophagic cell death", Molecular Therapy, 16(3): 487-493, 2008.
Alonso, "Can oncolytic adenovirus be implemented as therapeutic strategies for DIPGs?", DIPG European Meeting Barcelona, Feb. 2012.
Amalfitano, A., et al., "Improved adenovirus packaging cell lines to support the growth of replication-defective gene-delivery vectors," Proc Natl Acad Sci USA, 93: 3352-6, 1996.
Anderson et al., "Plasmid DNA and viral vector-based vaccines for the treatment of cancer", Vaccine, 25S: B24-B34, 2007.
Anderson, W.F., "Human Gene Therapy," Nature, 392: 25-30, 1998.
Arap, W., et al., "Cancer Treatment by Targeted Drug Delivery to Tumor Vasculature in a Mouse Model," Science, 279: 377-80, 1998.
Babiss et al., "Cellular Promoters Incorporated into the Adenovirus Genome," J. Mol. Biol., 193: 643-650, 1987.
Bangma et al., "Free Serum Prostate-Specific Antigen and Screening for Prostate Cancer," JAMA, 275(11 ): 837-8, 1996.
Barnes, et al., "Conditionally Replicative Adenoviruses for Ovarian Cancer Therapy", Mol. Cancer Thera., 1:435-439, 2002.
Beck et al., "The Thymidine Kinase/Ganciclovir-Mediated "Suicide" Effect Is Variabkle in Different Tumor Cells", Human Gene Therapy, 6: 1525-1530, 1995.
Bergelson, J.M., et al., "Isolation of a Common Receptor for Coxsackie B Viruses and Adenoviruses 2 and 5," Science, 275: 1320-3, 1997.
Bien et al., "Pre-treatment serum levels of interleukin-10, interleukin-12 and their ratio predict response to therapy and probability of event-free and overall survival in childhood soft tissue sarcomas, Hodgkin's lymphomas and acute lymphoblastic leukemias", Clinical Biochemistry, 42(10-11): 1144-1157, 2009.
Bischoff, J. R., et al., "An Adenovirus Mutant That Replicates Selectively in p53-Deficient Human Tumor Cells," Science, 274:373-376, 1996.
Blackwell, J., et al., "Retargeting to EGFR Enhances Adenovirus Infection Efficiency of Squamous Cell Carcinoma," Arch. Otolaryngol. Head Neck Surg., 125: 856-863, 1999.
Bonetta et al., "Research Notes", Nature Genetics, 34(2): 133, 2003.
Carbone, F.R., et al., "Cross-presentation: A General Mechanism for CTL Immunity and Tolerance," Immunol. Today, 19(8): 368-73, 1998.

(56) References Cited

OTHER PUBLICATIONS

Chartier, C., et al., "Efficient Generation of Recombinant Adenovirus Vectors by Homologous Recombination in *Escherichia coli,*" *J. Virol.*, 70(7): 4805-10, 1996.
Chiocca, "Oncolytic viruses", *Nat Rev Cancer*, 2(12): 938-50, 2002.
Cook, D.R., et al., "Gene Therapy for B -cell Lymphoma in a SCID Mouse Model using an Immunoglobulin-Regulated Diphtheria Toxin Gene Delivered by a Novel Adenovirus-Polylysine Conjugate," *Cancer Biother.*, 9(2): p. 131-41, 1994.
Curiel, "Strategies to Adapt Adenoviral Vectors for Targeted Delivery," *Annals New York Academy of Sciences*, 886: 158-171, 1999.
Curiel, D.T., "Strategies to improve the therapeutic utility of conditionally replicative adenoviruses (CRAds) for cancer therapy," *Proc. Amer. Assoc. Cancer Res. Ann. Meet.* 43: 662-663, abstract 3287, Mar. 2002.
Dachs et al., "Targeting gene therapy to cancer: A Review," *Oncology Res.*, 9: 313-325, 1997.
Database Accession No. AYD24277, dated Aug. 19, 2010.
Database Accession No. AYD74276, dated Aug. 19, 2010.
Deng, Y., et al., "MHC Immunodominance Affinity, Peptide Liberation, T Cell Repertoire, and All Contribute to the Paucity of MHC Class I-Restricted Peptides Recognized by Antiviral CTL," *J. Immunol.*, 158: 1507-15, 1997.
Dion, L.D., et al., "E1A RNA transcripts amplify adenovirus-mediated tumor reduction," *Gene Therapy*, 3: 1021-5, 1996.
Dion, L.D., et al., "Quantitative and in vivo activity of adenoviral-producing cells made by cotransduction of a replication-defective adenovirus and a replication-enabling plasmid," *Cancer Gene Therapy*, 3( 4): 230-7, 1996.
Dmitriev, I., et al., "An Adenovirus Vector with Genetically Modified Fibers Demonstrates Expanded Tropism via Utilization of a Coxsackievirus and Adenovirus Receptor-Independent Cell Entry Mechanism," *J. Virol.*, 72(12): 9706-13, 1998.
Dobner, T., et al., "Blockage by Adenovirus E4orf6 of Transcriptional Activation by the p53 Tumor Suppressor," *Science*, 272: 1470-3, 1996.
Eck et al., "Gene based therapy," *Goodman & Oilman's the Pharmacological Basis of Therapeutics*, 9th Ed., McGraw-Hill, 1996. 77-101. Print.
Eustace, D., et al., "Interleukin-6 (IL-6) Functions as an Autocrine Growth Factor in Cervical Carcinomas in Vitro," *Gynecol. Oncol.*, 50: 15-19, 1993.
Fallaux, F.J., et al., "New Helper Cells and Matched Early Region I-Deleted Adenovirus Vectors Prevent Generation of Replication-Competent Adenoviruses," *Human Gene Therapy*, 9: 1909-17, 1998.
Fechner, H., et al., "Expression of Coxsackie adenovirus receptor and alphav-integrin does not correlate with adenovector targeting in vivo indicating anatomical vector barriers," *Gene Therapy*, 6: 1520-1535, 1999.
Ferguson et al., "Systemic delivery of oncolytic viruses: hopes and hurdles", *Advances in Virology*, 2012: 805629, 2012.
Ferrin, L.J., "Manipulating and Mapping DNA with RecA-Assisted Restriction Endonuclease (RARE) Cleavage," *Genet. Eng.*, 17: 21-30, 1995.
Fick et al., "The extent of heterocellular communication mediated by gap junctions is predictive of bystander tumor cytotoxicity in vitro", *Proc. Natl. Acad. Sci.*, 92: 11071-11075, 1995.
Forsythe JA, et al., "Activation of vascular endothelial growth factor gene transcription by hypoxia-inducible factor 1," *MolCell Biol.*, 16(9):4604-13, 1996.
Fox, "Investigation of gene therapy begins", *Nature Biotechnology*, 18: 143-144, 2000.
Freytag et al., "A Novel Three-Pronged Approach to Kill Cancer Cells Selectively: Concomitant Viral, Double Suicide Gene, and Radiotherapy", *Human Gene Ther.*, 9: 1323-1333, 1998.
Fueyo et al., "Preclinical characterization of the antiglioma activity of a tropism-enhanced adenovirus targeted to the retinoblastoma pathway", *Journal of National Cancer Institute*, 95(9): 652-60, 2003.

Fueyo, J. et al., "A mutant oncolytic adenovirus targeting the Rb pathway produces anti-glioma effect in vivo," *Oncogene*, 19: 2-12, 2000.
Garver R., Jr., et al., "Strategy for achieving selective killing of carcinomas," *Gene Therapy*, 1: 46-50, 1994.
Goldman, C.K, et al., "Targeted Gene Delivery to Kaposi's Sarcoma Cells via the Fibroblast Growth Factor Receptor," *Cancer Res.*, 57: 1447-51, 1997.
Goldsmith, K.T., et al., "trans E1 Component Requirements for Maximal Replication of E1-Defective Recombinant Adenovirus," *Virology*, 248: 406-19, 1998.
Goldsmith, K.T., et al., "Trans Complementation of an E1A-Deleted Adenovirus with Codelivered E1A sequences to Make Recombinant Adenoviral Producer Cells," *Human Gene Therapy*, 5: 1341-8, 1994.
Gomez-Manzano, C., et al., "Adenovirus-mediated Transfer of the p53 Gene Produces Rapid and Generalized Death of Human Glioma Cells via Apoptosis," *Cancer Res.*, 56: 694-9, 1996.
Goodrum, F.D., et al., "p53 Status Does Not Determine Outcome of E1B 55-Kilodalton Mutant Adenovirus Lytic Infection," *J. Virol.*, 72(12): 9479-90, 1998.
Gotoh, A., et al., "Development of Prostate-Specific Antigen Promoter-Based Gene Therapy for Androgen-Independent Human Prostate Cancer," *J. Urol.*, 160: 220-9, 1998.
Green and Seymour, "Adenoviral vectors: systemic delivery and tumor targeting", *Cancer Gene Therapy*, 9: 1036-1042, 2002.
Hall, A.R. et al., "p53-dependent cell death/apoptosis is required for a productive adenovirus infection," *Nat. Med.*, 4(9): 1068-72, 1998.
Hardy, S. et al, "Construction of Adenovirus Vectors through Cre-lox Recombination," *J. Virol.*, 71(3): 1842-1849, 1997.
He et al., "A simplified system for generating recombinant adenoviruses," *Proc Natl Acad Sci U S A.*, 95(5): 2509-14, 1998.
Hearing and Shenk, "Sequence-independent autoregulation of the adenovirus type 5 E1A transcription unit", *Molecular and Cellular Biology*, 5(11):3214-3221, 1985.
Heise et al., "An adenovirus E1A mutant that demonstrates potent and selective systemic anti-tumoral efficacy," *Nature Medicine*, 6(10):1134-1139, 2000.
Heise, C., et al., "ONYX-015, an E1B gene-attenuated adenovirus, causes tumor-specific cytolysis and antitumoral efficacy that can be augmented by standard chemotherapeutic agents," *Nat. Med.*, 3: 639-645, 1997.
Heise, C.C., et al., "Efficacy of a replication-competent adenovirus (ONYX-015) following intratumoral injection: Intratumoral spread and distribution effects," *Cancer Gene Therapy*, 6: 499-504, 1996.
Hemmi, S., et al., "The Presence of Human Coxsackievirus and Adenovirus Receptor Is Associated with Efficient Adenovirus-Mediated Transgene Expression in Human Melanoma Cell Cultures," *Human Gene Therapy*, 9: 2363-73, 1998.
Hemminki and Johansson, "Cancer gene therapy in humans", Cancer Gene Therapy Group—University of Helsinki, dated Apr. 6, 2011.
Hemminki et al., "Serotype chimeric oncolytic adenovirus Ad5/3-Δ74 for targeted virotherapy of ovarian cancer", RAID application dated Aug. 2003.
Hobbs et al., "Regulation If transport pathways in tumor vessels: Role of tumor type and microenvironment", *Proc. Natl. Acad. Sci.*, 95: 4607-4612, 1998.
Hofmann, C., et al., "Ovine Adenovirus Vectors Overcome Preexisting Humoral Immunity against Human Adenoviruses In Vivo," *J. Virol.*, 73: 6930-36, 1999.
Imler et al., "Novel complementation cell lines derived from human lung carcinoma A549 cells support the growth of E1-deleted adenovirus vectors," *Gene Ther.* 3: 75-84, 1996.
Jain, "Delivery of Molecular and Cellular Medicine to Solid Tumors", *Journal of Controlled Release*, 53: 49-67, 1998.
Jiang et al., "Examination of the therapeutic potential of delta-24-RGD in brain tumor stem cells: role of autophagic cell death", *Journal of the National Cancer Institute* (GB), 99(18): 1410-1414, 2007.
Jiang et al., "Oncolytic adenovirus: preclinical and clinical studies in patients with human malignant gliomas", *Curr Gene Ther.*, 9(5):422-427, 2009.

(56) References Cited

OTHER PUBLICATIONS

Kasono, K., et al., "Selective Gene Delivery to Head and Neck Cancer Cells via an Integrin Targeted Adenoviral Vector," *Clin. Cancer Res.*, 5: 2571-2579, 1999.
Kirn, D., et al., "ONYX-015: Clinical data are encouraging," *Nat. Med.*, 4(12): 1341-2, 1998.
Kirn, D., et al., "Replicating Viruses as Selective Cancer Therapeutics," *Mol. Med. Today*, 2(12): 519-27, 1996.
Koivunen, E. et al., "Identification of Receptor Ligands with Phage Display Peptide Libraries," *J. Nucl. Med.*, 40: 883-888, 1999.
Kong, B., et al., "IL-6 Antisense-Mediated Growth Inhibition of a Choriocarcinoma Cell Line: An Intracellular Autocrine Growth Mechanism," *Gynecol. Oncol.*, 63: 78-84, 1996.
Krasnykh, V., et al., "Characterization of an Adenovirus Vector Containing a Heterologous Peptide Epitope in the HI Loop of the Fiber Knob," *J. Virol.*, 72(3): 1844-52, 1998.
Krasnykh, V., et al., "Generation of Recombinant Adenovirus Vectors with Modified Fibers for Altering Viral Tropism," *J. Virol.*, 70: 6839-6846, 1996.
Krause et al., "Epitopes expressed in different adenovirus capsid proteins induce different levels of epitope-specific immunity", *Journal of Virology*, 80(11): 5523-5530, 2006.
Kremer, E. J., et al., "Canine Adenovirus Vectors: an Alternative for Adenovirus-Mediated Gene Transfer," *J. Virol.*, 74: 505-512, 2000.
Laquerre et al., "Recombinant Herpes Simplex Virus Type 1 Engineered for Targeted Binding to Erythropoietin Receptor-Bearing Cells," *Journal of Virology*, 72(12): 9683-9697, 1998.
Lee et al., "Enhanced antitumor effect of oncolytic adenovirus expressing interleukin-12 and B7-1 in an immunocompetent murine model", *Clinical Cancer Research*, 12:5859-5868, 2006.
Leissner et al., "Influence of adenoviral fiber mutations on viral encapsidation, infectivity and in vivo tropism," Gene Therapy 8: 49-57, 2001.
Majem et al., "Control of E1A under an E2F-1 promoter insulated with the myotonic dystrophy locus insulator reduces the toxicity of oncolytic adenovirus Ad-Δ24RGD," *Cancer Gene Therapy*, 13:696-705, 2006.
Miller, C.R., et al., "Differential Susceptibility of Primary and Established Human Glioma Cells to Adenovirus Infection: Targeting via the Epidermal Growth Factor Receptor Achieves Fiber Receptor-independent Gene Transfer," *Cancer Res.*, 58: 5738-48, 1998.
Miller, N., et al., "Progress in Transcriptionally Targeted and Regulatable Vectors for Genetic Therapy," *Human Gene Therapy*, 8: 803-15, 1997.
Mittereder, N., et al., "Evaluation of the Concentration and Bioactivity of Adenovirus Vectors for Gene Therapy," *J. Virology*, 70(11):7498-509, 1996.
Mocellin et al., "Kinetics of cytokine expression in melanoma metastases classifies immune responsiveness", *Int J Cancer*, 93: 236-242, 2001.
Moolten, F. L., "Drug Sensitivity ("suicide") genes for selective cancer chemotherapy," *Cancer Gene Therapy*, 1(4): 279-87, 1994.
Moran, E., "Interaction of adenoviral proteins with pRB and p53," *Faseb J*, 7: 880-5, 1993.
Murray, E.J., et al., "Sequences and Factors Required for the F9 Embryonal Carcinoma Stem Cell E1a-Like Activity," *Mol. Cell Biol.*, 11(11): 5534-40, 1991.
NCBI Reference Sequence: GenBank Accession No. AC _000008. 1, Dec. 1, 2004.
Nelson, J.E., et al., "Persistence of Recombinant Adenovirus In Vivo Is Not Dependent on Vector DNA Replication," *J. Virol.*, 71(11): 8902-7, 1997.
Nokisalmi et al., "Oncolytic adenovirus ICOVIR-7 in patients with advanced and refractory solid tumors", *Clinical Cancer Research*, 16(11):3035-3043, 2010.
Office Communication issued in Chinese Application No. 201380010639.1, dated Sep. 6, 2015.
Office Communication issued in New Zealand Application No. 627736, dated Mar. 31, 2015.
Office Communication issued in Chinese Application No. 201380017639.4, dated Sep. 15, 2015.
Office Communication issued in European Application No. 13704334. 5, dated Mar. 2, 2016.
Office Communication issued in New Zealand Application No. 628213, dated Apr. 24, 2015.
Ohta Y, et al., "Significance of vascular endothelial growth factor messenger RNA expression in primary lung cancer," *ClinCancer Res.*, 2(8): 1411-6, 1996.
O'Riordan, C., et al., "PEGylation of Adenovirus with Retention of Infectivity and Protection from Neutralizing Antibody in Vitro and in Vivo," *Human Gene Therapy*, 10: 1349-1358, 1999.
Paillard, F., "The Search for the "Best" Cytokine to Induce Anti-tumor Immunity," *Hum Gene Therapy*, 9: 2457-8, 1998.
Pasqualini, R., et al., "αv Integrins as receptors for tumor targeting by circulating ligands," *Nat. Biotechnol.*, 15: 542-6, 1997.
PCT International Preliminary Report on Patentability issued in International Application No. PCT/US2013/024506, dated Aug. 14, 2014.
PCT International Preliminary Report on Patentability issued in International Application No. PCT/US2013/023304, dated Aug. 7, 2014.
PCT International Search Report and Written Opinion issued in International Application No. PCT/US2013/023304, dated Apr. 11, 2013.
PCT International Search Report and Written Opinion issued in International Application No. PCT/US2013/024506, dated Oct. 28, 2013.
PCT International Search Report and Written Opinion issued in International Application No. PCT/US2014/042375, dated Oct. 7, 2014.
PCT Invitation to Pay Additional Fees issued in International Application No. PCT/US2013/023304, dated Apr. 19, 2013.
Peng et al., "Viral vector targeting," *Current Opinion in Biotechnology*, 10: 454-457, 1999.
Raben, D., et al., "Enhancement of radiolabeled antibody binding and tumor localization through adenoviral transduction of the human carcinoembryonic antigen gene," Gene Therapy, 3: 567-80, 1996.
Rajotte, "Molecular Heterogeneity of the Vascular Endothelium Revealed by in Vivo Phage Display," *J. Clin. Invest.*, 102: 430-437, 1998.
Rancourt et al., "Conditionally replicative adenoviruses for cancer therapy", *Advanced Drug Delivery Reviews*, 27: 67-81, 1997.
Rasmussen, et al., "Matrix Metalloproteinase Inhibition as a Novel Anticancer Strategy: A Review with Special Focus on Batimastat and Marimastat," *Pharmacol Ther.*, 75(1): 69-75, 1997.
Reid et al., "Intravascular adenoviral agents in cancer patients: lessons from clinical trials", *Cancer Gene Therapy*, 9: 979-986, 2002.
Rodriguez, R., et al., "Prostate Attenuated Replication Competent Adenovirus (ARCA) CN706: A Selective Cytotoxic for Prostate-specific Antigen-positive Prostate Cancer Cells," *Cancer Res.*, 57(13): 2559-63, 1997.
Roelvink et al., "The coxsachievirus-adenovirus receptor protein can function as a cellular attachment protein for adenovirus serotypes from subgroups A, C, D, E, and F," *J. Virol.*, 72(10): 7909-7915, 1998.
Roelvink, P. W., et al., "Identification of a Conserved Receptor-Binding Site on the Fiber Proteins of CAR-Recognizing Adenoviridae," *Science*, 286: 1568-1571, 1999.
Rokhlin, O.W., et al., , "Expression of Cellular Adhesion Molecules on Human Prostate Tumor Cell Lines," *Prostate*, 26: 205-212, 1995.
Roth, J., et al., "Gene Therapy for Cancer: What Have We Done and Where Are We Going?," *J. Natl Cancer Inst.*, 89(1): 21-39, 1997.
Rothmann, T., et al., , "Replication of ONYX-015, a Potential Anticancer Adenovirus, Is Independent of p53 Status in Tumor Cells," *J. Virol.*, 72(12): 9470-8, 1998.
Rouslahti and Rajotte, "An address system in the vasculature of normal tissues and tumors", *Annu Rev Immunol.*, 18:813-27, 2000.
Russell, S.J., "Replicating vectors for cancer therapy: a question of strategy," *Semin. Cancer Biol.*, 5: 437-43, 1994.

(56) References Cited

OTHER PUBLICATIONS

Sandhu et al., "Human Gene Therapy," *Critical Reviews in Biotechnol.*, 17(4): 307-326, 1997.
Scaria, A., et al., "Complementation of a human adenovirus early region 4 deletion mutant in 293 cells using adenovirus polylysine-DNA complexes," *Gene Therapy*, 2: 295-8, 1995.
Schreiber H. "Tumor Immunology," *Fundamental Immunology*, 4th Ed., W.E. Paul, Editor. Lippincott-Raven Publishers: Philadelphia, 1999. 1237-1270. Print.
Schuepbach, J., et al., "Inverse Correlation of Antiviral Antibody Titers and the Remission Length in Patients Treated with Viral Oncolysate: A Possible New Prognostic Sign in Acute Myelogenous Leukemia," *Cancer*, 48: 1363-7, 1981.
Shi, Q. et al., "Modulation of the Specificity and Activity of a Cellular Promoter in an Adenoviral Vector," *Human Gene Therapy*, 8: 403-10, 1997.
Shinoura N, et al., "Highly augmented cytopathic effect of a fiber-mutant E1B-defective adenovirus for gene therapy of gliomas," *Cancer Res.*, 59(14): 3411-6, 1999.
Sinkovics, J., et al., "New Developments in the Virus Therapy of Cancer: A Historical Review," *Intervirology*, 36: 193-214, 1993.
Smith, C.A., et al., "Adenovirus-Pulsed Dendritic Cells Stimulate Human Virus-Specific T-Cell Responses In Vitro," *J. Virology*, 70(10): 6733-40, 1996.
Spergel, J., et al., "Interleukin 6 enhances a cellular activity that functionally substitutes for E1A protein in transactivation," *Proc Natl Acad Sci USA*, 88: 6472-6, 1991.
Stevenson et al., "Selective Targeting of Human Cells by a Chimeric Adenovirus Vector Containing a Modified Fiber Protein", *Journal of Virology*, 71(6): 4782-4790, 1997.
Stevenson, S., et al., "Human Adenovirus Serotypes 3 and 5 Bind to Two Different Cellular Receptors via the Fiber Head Domain," *J. Virol.*, 69: 2850-2857, 1995.
Sussenbach, J, "The Structure of the Genome", *The Adenoviruses* (1984), Chapter 3, pp. 35-124.
Suzuki et al., "A conditionally replicative adenovirus with enhanced infectivity shows improved oncolytic potentcy", *Clinical Cancer Research*, 7: 120-126, 2001.
Tahara et al., "Emerging concepts in biomarker discovery; the US-Japan workshop on immunological molecular markers in oncology", *Journal of Translational Medicine*, 7(1): 45, 2009.
Takayama et al., "Conditionally replicative adenovirus, AdVEGFE1, has a possibility for universal application in various cancer treatments", *Mol. Ther.*, 5: S268, abstract 821, May 2002.
Takayama et al., "VEGF promoter based conditionally replicative adenovirus are useful for the treatment of lung cancer", *Mol. Ther.* 7(5, Part 2): S420, abstract 1089, 2003.
Takayama K, et al., "Suppression of tumor angiogenesis and growth by gene transfer of a soluble form of vascular endothelial growth factor receptor into a remote organ," *Cancer Res.*, 60(8):2169-77, 2000.
Takayama K, et al., "The levels of integrin alpha v beta 5 may predict the susceptibility to adenovirus-mediated gene transfer in human lung cancer cells," *Gene Ther.*, 5(3):361-8, 1998.
Takenawa, J., et al., "Enhanced Expression of interleukin-6 in Primary Human Renal Cell Carcinomas", *J Natl Cancer Inst*, 83(22): 1668-72, 1991.
Tanaka, T., et al., "Viral Vector-targeted Antiangiogenic Gene Therapy Utilizing an Angiostatin Complementary DNA," *Cancer Res.*, 58: 3362-9, 1998.
Todo, T., et al., "Systemic Antitumor Immunity in Experimental Brain Tumor Therapy Using a Multimutated, Replication-Competent herpes Simplex Virus," *Human Gene Therapy*, 10: 2741-2755, 1999.
Urban, J.L., et al., "Stepwise Immunologic Selection of Antigenic Variants During Tumor Growth," *J. Immunology*, 137(9): 3036-41, 1986.
Vanderkwaak et al., "Adenovirus with RGD-modified fiber demonstrates improved gene transfer into ovarian carcinoma cell lines and ovarian primary tumors" in Abstracts Presented for the thirtieth annual meeting of the society of gynecologic oncologists, *Gynecologic Oncology*, 72(3): 443-527, 1999. Abstract 254, p. 505.
Verma et al., "Gene therapy—promises, problems and prospects", *Nature*, 389: 239-242, 1997.
Vile et al., "The oncolytic virotherapy treatment platform for cancer: Unique biological and biosafety points to consider", *Cancer Gene Therapy*, 9:1062-1067, 2002.
Von Seggern et al., "Adenovirus Vector Pseudotyping in Fiber-Expressing Cell Lines: Improved Transduction of Epstein-Barr Virus-Transformed B Cells," *J. Virol.*, 74: 354-362, 2000.
Wen et al., "Tricistronic viral vectors co-expressing interleukin-12 (IL-12) and CD80 (B7-1) for the immunotherapy of cancer: preclinical studies in myeloma", *Cancer Gene Therapy*, 8(5): 361-370, 2001.
Whyte et al., "Cellular targets for transformation by the adenovirus E1A proteins," *Cell*, 56:67-75, 1989.
Whyte et al., "Two regions of the adenovirus early region 1A proteins are required for transformation," *Journal of Virology*, 62(1):257-265, 1988.
Wickham, T., et al., "Increased In Vitro and In Vivo Gene Transfer by Adenovirus Vectors Containing Chimeric Fiber Proteins," *J. Virol.*, 71(11): 8221-9, 1997.
Wildner, O., et al., "Adenoviral vectors capable of replication improve the efficacy of HSVtk/GCV suicide gene therapy of cancer," *Gene Therapy*, 6: 57-62, 1999.
Wildner, O., et al., "Therapy of Colon Cancer with Oncolytic Adenovirus Is Enhanced by the Addition of Herpes Simplex Virus-thymidine kinase," *Cancer Res.*, 59: 410-413, 1999.
Wittke et al., "Interleukin 10 (IL-10): an immunosuppressive factor and independent predictor in patients with metastatic renal cell carcinoma", *British Journal of Cancer*, 79(7/8): 1182-1184, 1999.
Wongthida et al., "Type III IFN interleukin-28 mediates the antitumor efficacy of oncolytic virus VSV in immune-competent mouse models of cancer", *Cancer Research*, 70(11): 4539-4549, 2010.
Worgall, S., et al., "Innate Immune Mechanisms Dominate Elimination of Adenoviral Vectors Following In Vivo Administration," *Human Gene Therapy*, 8: 37-44, 1997.
Worschech et al., "Systemic treatment of xenografts with vaccinia virus GLV-1h68 reveals the immunologic facet of oncolytic therapy", *BMC Genomics*, 10(1): 301, 2009.
Xia, et al., "Structure of the Receptor Binding Domain of Adenovirus Type 5 Fiber Protein," *Curr. Top. Microbiol. Immunol.*, 199 (1): 39-46, 1995.
Yang, Y., et al., "Recombinant IL-12 prevents formation of blocking IgA antibodies to recombinant adenovirus and allows repeated gene therapy to mouse lung," *Nat. Med.*, 1: 890-893, 1995.
Yeh, P., et al., "Advances in adenoviral vectors: from genetic engineering to their biology," *FASEB J*, 11: 615-23, 1997.
Yoshida, Y., et al., "Generation of Fiber-Mutant Recombinant Adenoviruses for Gene Therapy of Malignant Glioma," *Human Gene Therapy*, 9: 2503-15, 1998.
Yu, D. C., et al., "Identification of the Transcriptional Regulatory Sequences of Human Kallikrein 2 and Their Use in the Construction of Calydon Virus 764, an Attenuated Replication Competent Adenovirus for Prostate Cancer Therapy", *Cancer Res.*, 59: 1498-1504, 1999.
Yu, D., et al., "Enhanced c-erbB-2/neu Expression in Human Ovarian Cancer Cells Correlates with More Severe Malignancy that can be Suppressed by E1A", *Cancer Res.*, 53: 891-8, 1993.
Yurkovetsky et al., "Multiplex analysis of serum cytokines in melanoma patients treated with interferon-2b", *Clinical Cancer Research*, 13(8): 2422-2428, 2007.
Zhang et al., "Eradication of solid human breast tumors in nude mice with an intravenously injected light-emitting oncolytic vaccinia virus", *Cancer Research*, 67(20): 10038-10046, 2007.
Zhang, J., et al., "Vectors for Cancer Gene Therapy," *Cancer Metastasis Rev.*, 15: 385-401, 1996.
Zheng, D. Q., et al., "Prostatic Carcinoma Cell Migration via alpha(v)beta3 Integrin is Modulated by a Focal Adhesion Kinase Pathway," *Cancer Res.*, 59: 1655-1664, 1999.
Office Communication issued in corresponding Japanese Application No. 2014-554887, dated Oct. 2, 2017. (English translation).

(56) References Cited

OTHER PUBLICATIONS

Cerullo et al. "Immunological effects of low-dose cyclophosphamide in cancer patients treated with oncolytic adenovirus", *Molecular Therapy*, 19(9): 1737-1746, 2011.

Dziurzynski et al. "Cytomegalovirus Subverts the Monocyte Lineage to Become Glioma Propagating," *Neuro-Oncology*, 13: iii30-iii33, 2011.

Grauer et al. "CD4+FoxP3+ regulatory T cells gradually accumulate in gliomas during tumor growth and efficiently suppress antiglioma immune responses in vivo", *Int. J. Cancer*, 121: 95-105, 2007.

Murphy et al. "Janeway's Immunobiology", $7^{th}$ ed. 2008. Japanese Translation of pp. 427-429.

Office Communication issued in corresponding Japanese Application No. 2014-554887, dated Dec. 26, 2016.

Office Communication issued in corresponding Chinese Application No. 201380010639.1, dated Jan. 16, 2017.

Szabo and Carpentier, "Immunotherapy in human glioblastoma", *Revue Neurologique*, 167(10): 668-672, 2011.

\* cited by examiner

Figure 3
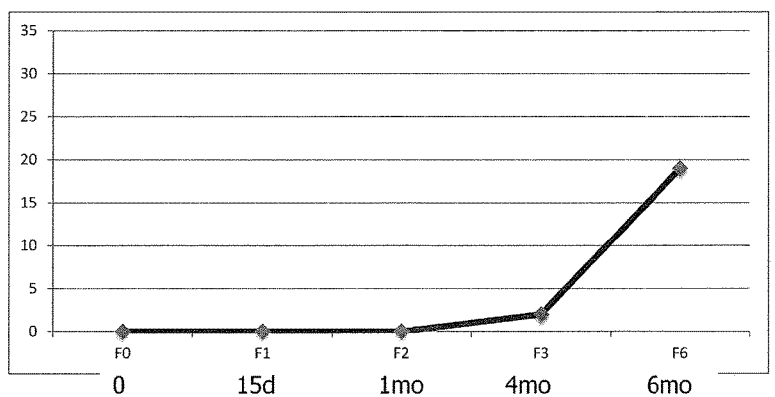
 

Figure 4

Patient G (26 months, alive)

| (months) | 0 | 1 | 4 | 6 |
|---|---|---|---|---|
| | G0 | G2 | G3 | G6 |
| BRAF | 0.335 | 0.275 | 0.229 | 0.265 |
| CABYR | 0.52 | 0.437 | 0.435 | 0.166 |
| CRISP3 | 0.237 | 0.252 | 0.255 | 0.277 |
| CSAG2 | 0.194 | 0.185 | 0.261 | 0.304 |
| CTAG2 | 0.327 | 0.266 | 0.284 | 0.471 |
| DHFR | 0.467 | 0.221 | 0.287 | 0.225 |
| FHLT17 | 0.416 | 0.34 | 0.411 | 0.205 |
| GAGE1 | 0.284 | 0.204 | 0.295 | 0.35 |
| LDHC | 0.254 | 0.168 | 0.171 | 0.224 |
| MAGEA1 | 0.496 | 0.39 | 0.383 | 0.265 |
| MAGEA3 | 0.374 | 0.281 | 0.507 | 0.191 |
| MAGEA4 | 0.347 | 0.27 | 0.37 | 0.257 |
| MAGEB6 | 0.354 | 0.268 | 0.322 | 0.24 |
| MAPK1 | 0.439 | 0.294 | 0.347 | 0.175 |
| MICA | 0.363 | 0.33 | 0.332 | 0.288 |
| MUC1 | 0.41 | 0.26 | 0.308 | 0.274 |
| NLRP4 | 0.506 | 0.298 | 0.481 | 0.273 |
| NYESO1 | 0.463 | 0.445 | 0.507 | 0.209 |
| P53 | 0.367 | 0.26 | 0.409 | 0.239 |
| PBK | 0.405 | 0.307 | 0.411 | 0.221 |
| PRAME | 0.271 | 0.285 | 0.352 | 0.268 |
| SOX2 | 0.355 | 0.169 | 0.333 | 0.254 |
| SPANXA1 | 0.357 | 0.319 | 0.284 | 0.27 |
| SSX2 | 0.432 | 0.417 | 0.418 | 0.212 |
| SSX4 | 0.306 | 0.21 | 0.302 | 0.275 |
| SSX5 | 0.431 | 0.368 | 0.433 | 0.254 |
| TSGA10 | 0.315 | 0.182 | 0.325 | 0.232 |
| TSSK6 | 0.388 | 0.327 | 0.32 | 0.231 |
| TULP2 | 0.302 | 0.29 | 0.367 | 0.253 |
| XAGE2 | 0.393 | 0.318 | 0.476 | 0.344 |
| ZNF165 | 0.434 | 0.342 | 0.461 | 0.275 |
| SCORE | 0 | 0 | 0 | 0 |

Patient I (6 months, deceased)

| (months) | 0 | 1 | 3 | 4 |
|---|---|---|---|---|
| | I0 | I2 | I2.5 | I3 |
| BRAF | 0.34 | 0.387 | 0.875 | 0.804 |
| CABYR | 0.612 | 0.762 | 0.545 | 0.632 |
| CRISP3 | 0.377 | 0.403 | 0.562 | 0.697 |
| CSAG2 | 0.299 | 0.324 | 0.481 | 0.618 |
| CTAG2 | 0.491 | 0.569 | 0.938 | 0.927 |
| DHFR | 0.411 | 0.51 | 0.658 | 0.753 |
| FHLT17 | 0.569 | 0.654 | 0.678 | 0.883 |
| GAGE1 | 0.345 | 0.378 | 0.687 | 0.763 |
| LDHC | 0.275 | 0.289 | 0.593 | 0.628 |
| MAGEA1 | 0.649 | 0.739 | 0.581 | 0.709 |
| MAGEA3 | 0.603 | 0.71 | 0.72 | 0.776 |
| MAGEA4 | 0.519 | 0.614 | 0.737 | 0.747 |
| MAGEB6 | 0.651 | 0.713 | 0.625 | 0.69 |
| MAPK1 | 0.579 | 0.599 | 0.706 | 0.789 |
| MICA | 0.412 | 0.424 | 0.594 | 0.872 |
| MUC1 | 0.546 | 0.494 | 0.559 | 0.615 |
| NLRP4 | 0.755 | 0.767 | 0.747 | 0.815 |
| NYESO1 | 0.774 | 0.759 | 0.666 | 0.696 |
| P53 | 0.579 | 0.787 | 0.545 | 0.608 |
| PBK | 0.609 | 0.759 | 0.679 | 0.832 |
| PRAME | 0.465 | 0.562 | 0.721 | 0.765 |
| SOX2 | 0.381 | 0.496 | 0.66 | 0.804 |
| SPANXA1 | 0.47 | 0.622 | 0.649 | 0.796 |
| SSX2 | 0.631 | 0.745 | 0.623 | 0.737 |
| SSX4 | 0.393 | 0.537 | 0.609 | 0.728 |
| SSX5 | 0.681 | 0.768 | 0.625 | 0.784 |
| TSGA10 | 0.54 | 0.748 | 0.689 | 0.793 |
| TSSK6 | 0.525 | 0.622 | 0.617 | 0.7 |
| TULP2 | 0.461 | 0.627 | 0.686 | 0.793 |
| XAGE2 | 0.584 | 0.684 | 0.592 | 0.611 |
| ZNF165 | 0.603 | 0.867 | 0.693 | 0.736 |
| SCORE | 10 | 18 | 22 | 31 |

BIOMARKERS AND COMBINATION THERAPIES USING ONCOLYTIC VIRUS AND IMMUNOMODULATION

CROSS-REFERENCE TO RELATED APPLICATIONS

This application is a national phase application under 35 U.S.C. § 371 of International Application No. PCT/US2013/023304, filed Jan. 25, 2013, which claims the benefit of U.S. Provisional Application No. 61/590,441, filed Jan. 25, 2012, and U.S. Provisional Application No. 61/637,191, filed Apr. 23, 2012, the entire content of each of which is specifically incorporated herein by reference.

BACKGROUND

I. Field of Invention

The present invention relates generally to the fields of oncology and cancer therapy. In some aspects, the present invention concerns combination therapies including oncolytic viruses such as adenoviruses and immune modulating therapies. In other aspects, the present invention concerns the measurement or detection of biomarkers that distinguish responders from non-responders to oncolytic viral therapy.

II. Background

It is estimated that 43,800 new cases of primary brain tumor, both malignant and nonmalignant, were diagnosed in the U.S. in 2005. It was estimated at 20,500 primary malignant brain tumors including astrocytic (42%) were expected in 2007. This was a more male predominant disease with estimated 11,700 in men and 8,800 in women in 2007. There were approximately 12,700 people who died with brain disease from these tumors estimated in the US in 2007. These tumors account for 1.4% of all adult cancers and 22% of all childhood cancers. This accounts for 2.4% of all cancer related deaths (SEER Cancer Statistics Review).

Onocolytic viruses have shown potential as anti-cancer agents. Genetic modification of the viruses to selectively replicate in cancer cells further increases their efficacy. In gliomas, for example, three kinds of viruses have been shown to be useful in animal models: reoviruses that can replicate selectively in tumors with an activated ras pathway (Coffey et al., 1998); genetically altered herpes simplex viruses (Martuza et al., 1991; Mineta et al., 1995; Andreanski et al., 1997), including those that can be activated by the different expression of protein in normal and cancer cells (Chase et al., 1998); and mutant adenoviruses that are unable to express the E1B55 kDa protein and are used to treat p53-mutant tumors (Bischof et al., 1996; Heise et al., 1997; Freytag et al., 1998; Kim et al., 1998). In all three systems, the goal is the intratumoral spread of the virus and the ability to selectively kill cancer cells. Genetically modified adenoviruses that target cellular pathways at key points have both potent and selective anti-cancer effects in gliomas. Frequently tested modifications of the adenovirus include deletion of the viral genes that interact with tumor suppressor genes, the modification of the tropism to infect cancer cells with more potency, and the inclusion in the viral genome of elements of transcription that are sensitive to transcription factors upregulated in cancer cells.

The role that preexisting immune conditions play and their influence in the overall clinical outcome of oncolytic virus therapy is presently unknown. The ability to accurately predict survival in patients treated with oncolytic viruses such as Delta-24-RGD would improve current treatment decisions. Furthermore, it would aid in the design of new therapies that may be tailored, with the basis of tumor properties and immune status. A significant advance in the field of biotherapy would occur because there is presently a dramatic lack of clinical biomarkers for cancer immunotherapy strategies.

The need for therapies effective against primary tumors of the nervous system, such as diffuse gliomas, anaplastic astrocytomas, anaplastic oligodendrogliomas, anaplastic mixed oligoastrocytoma, glioblastoma, ependymomas, and anaplastic ependymomas, or any primary brain tumor is particularly acute.

SUMMARY

The present invention relates to the identification of Th1 (inflammatory) cytokines and antibodies against tumor associated antigens as biomarkers for correlating their expression patterns as predictors of responsiveness to treatment with oncolytic viruses in patients with cancer. The invention thus provides for the identification and use of expression profiles which correlate with (and thus are able to discriminate between) patients with good or poor treatment outcomes. In several embodiments, the invention provides expression patterns that are able to identify patients with cancer that are likely to be non-responsive to treatment with an oncolytic virus from those that are responsive or likely to be responsive to treatment with an oncolytic virus. Responsiveness may be viewed in terms of better survival outcomes over time. Responsiveness may also be viewed in terms of reduction in tumor size according to e.g. the RECIST criteria.

The present invention also relates to novel methods for treating cancer patients comprising the co-administration of oncolytic virus and agents which stimulate a Th1 immune response in the patient and/or suppress a Th2 immune response and/or suppress regulatory T cells in the patient.

In one aspect, the present invention provides an objective means for identifying patients with cancer as likely to respond, or not respond, to treatment with an oncolytic virus by assaying for the expression level of one or more of the biomarkers described herein. Expression of these biomarkers thus provides an objective means to determine cancer prognosis (treatment outcome) with significant accuracy. These biomarkers may be used in combination with subjective criteria.

The biomarkers described herein are identified as correlating with oncolytic virus treatment outcome in patients with cancer such that their expression levels are relevant to determining appropriate treatment protocols. In one embodiment, the patient is a patient with a high grade glioma and the oncolytic virus is an adenovirus such as Delta-24-RGD.

The biomarkers described herein may be used singly with significant accuracy or in any combination, such as in the format of a ratio of expression levels, to increase the ability to accurately correlate an expression profile with a treatment outcome. The biomarkers can be used to predict treatment responsiveness, survival outcome and determination and/or alteration of therapy. The ability to identify patients likely to respond to, or likely not to respond to, oncolytic virus therapy is conferred by the identification of an expression level of the biomarkers and not by the methodology used to determine such expression level. Thus, the assay may utilize any feature of a biomarker described herein as long as the assay provides a qualitative or preferably a quantitative expression of the protein (or gene). By way of example, a biomarker can be measured or detected by a variety of methods, including, but not limited to immunohistochemistry (IHC), immunoassays, protein arrays, reverse protein arrays, nucleic acid arrays, mass spectroscopy, polymerase chain reaction (PCR) and the like.

In several embodiments, a method for predicting whether a patient having or suspected of having cancer will respond therapeutically to a method of treating cancer comprising administering an oncolytic virus is provided comprising the steps of (a) determining the level of expression of one or more Th1 biomarkers and/or one or more Th2 biomarkers and/or one or more antibodies against one or more tumor associated antigens in a test sample from the patient relative to a control (b) comparing the level of expression of one or more Th1 biomarkers and/or one or more Th2 biomarkers and/or one or more antibodies against one or more tumor associated antigens in the test sample to that in the control, wherein a change in the level of expression of one or more Th1 and/or one or more Th2 biomarkers and/or antibodies against one or more tumor associated antigens in the test sample relative to the control sample is predictive of the patient's treatment response to the oncolytic virus. The test samples include but are not limited to blood, plasma, serum, tissue biopsy, and cerebrospinal fluid. In related embodiments, the method comprises determining the level of at least one Th1 biomarker and the level of antibodies against at least one tumor associated antigen in step (a) and comparing these levels to a control in step (b).

The expression level of the one or more biomarkers can be determined prior to, simultaneous with or after administration of an oncolytic virus in order to predict the outcome of the therapy. In one embodiment, a method for treating cancer in a patient is provided comprising (a) determining the level of expression of one or more Th1 biomarkers and/or one or more Th2 biomarkers and/or one or more antibodies against one or more tumor associated antigens in a test sample from the patient obtained prior to administration of an oncolytic virus relative to a control (b) comparing the level of expression of one or more Th1 biomarkers and/or one or more Th2 biomarkers and/or one or more antibodies against one or more tumor associated antigens in the test sample to that in the control, wherein a change in the level of expression of one or more Th1 and/or one or more Th2 biomarkers and/or antibodies against one or more tumor associated antigens in the test sample relative to the control sample is predictive of the patient's treatment response to the oncolytic virus and optionally (c) administering the oncolytic virus to the patient if the patient is determined to be likely to respond to treatment with the virus. In a preferred embodiment, oncolytic virus is an adenovirus such as Delta-24-RGD, the test sample is a serum sample and the levels IL-12p70 and optionally at least one additional Th1 biomarker are determined in the sample and compared to a control.

In a related embodiment, the patient is determined as unlikely to respond to the oncolytic virus treatment if low levels of one or more Th1 biomarkers (e.g. IL-12p70) and/or high levels of antibodies against one or more tumor associated antigens (e.g. NLRP4) are determined in the test sample relative to a control. For example, step (b) as described above may comprise detecting the level of one or more Th1 biomarkers and/or antibodies against one or more tumor associated antigens in the test sample relative to the level of one or more Th1 biomarkers and/or antibodies against one or more tumor associated antigens from a subject having the same cancer that is responsive to treatment with the oncolytic virus, wherein lower levels of one or more Th1 biomarkers and/or higher levels of antibodies against one or more tumor associated antigens in the subject having the same cancer that is responsive to treatment indicates that the patient is non-responsive to treatment with the oncolytic virus. Preferably, the test sample from the patient and the sample from the subject are taken at the same time point. Thus, the expression pattern of the biomarkers described herein is useful for the identification of patients presenting with cancer that are unlikely to respond to treatment with an oncolytic virus. These patients are thus identified as good candidates for co-administration of agents which stimulate a Th1 immune response with an oncolytic virus. Alternatively, these patients are identified as good candidates for alternative treatment modalities.

In another related embodiment, the patient is determined as likely to respond to oncolytic virus treatment if high levels of one or more Th1 biomarkers (e.g. IL-12p70) and/or low levels of antibodies against one or more tumor associated antigens (e.g. NLRP4) are determined in the test sample relative to a control. For example, step (b) as described above may comprise detecting the level of one or more Th1 biomarkers and/or antibodies against one or more tumor associated antigens in the test sample relative to the level of one or more Th1 biomarkers and/or antibodies against one or more tumor associated antigens from a subject having the same cancer that is not responsive to treatment with the oncolytic virus, wherein higher levels of one or more Th1 biomarkers and/or lower levels of antibodies against one or more tumor associated antigens in the subject having the same cancer that is not responsive to treatment indicates that the patient is responsive to treatment with the oncolytic virus. Preferably, the test sample from the patient and the sample from the subject are taken at the same time point. Thus, the expression pattern of the biomarkers described herein is useful for the identification of patients presenting with cancer that that are likely to respond to treatment with an oncolytic virus. These patients are good candidates for administration of the oncolytic virus and may be administered the virus.

In other embodiments, a method for evaluating a patient with cancer for responsiveness to oncolytic viral therapy is provided comprising (a) measuring or detecting one or more biomarkers indicative of the immunologic status of the subject in a test sample from the subject (b) identifying, based on the levels of the one or more biomarkers, a subject having cancer that is likely or not likely to respond to the therapy, wherein a favorable response is likely if the immune status of the subject indicates a Th1 polarization and optionally (c) administering the subject an oncolytic viral therapy if a favorable response is likely. In certain aspects, the biomarker is a cytokine, cell surface marker, or antibody.

In one aspect, a method for predicting the likelihood that a subject will respond therapeutically to a method of treating cancer by administering an oncolytic virus comprises the following steps: (a) measuring the expression level of at least one biomarker suitable for determining the Th1 and/or Th2 immunologic status of the subject prior to administration of the virus (b) comparing the expression level of step (a) to a predetermined control, whereby an increase in one or biomarkers of Th1 immune status relative to the control and/or a decrease in one or more biomarkers of Th2 immune status relative to the control indicates an increased likelihood that the subject will respond therapeutically to said method of treating cancer and optionally (c) administering an oncolytic virus to the subject if an increased likelihood of response is indicated.

In another aspect, the expression level of one or more biomarkers in a patient with cancer is assessed at multiple time points as a means of predicting the patient's clinical outcome wherein the patient is undergoing oncolytic virus therapy. This method comprises measuring at least one Th1 biomarker and/or antibodies against at least one tumor associated antigen in two or more test samples from the patient over a period of time in order to determine whether a patient should continue treatment with the oncolytic virus or alternatively whether the patient is a candidate for co-administration of an agent to produce a Th1 phenotype. A decrease in at least one Th1 biomarker and/or an increase in antibodies against one or more tumor associated antigens compared to the level of the same Th1 biomarker(s) and/or antibodies at an earlier time point indicates that the patient is at risk for a negative outcome. Alternatively, a decrease in at least one Th1 biomarker and/or an increase in antibodies against one or more tumor associated antigens compared to the level of the same Th1 biomarker(s) and/or antibodies in another patient undergoing the same treatment indicates that the patient is at risk for a negative outcome. Thus, in one embodiment, a method for treating cancer in a patient having or suspected of having cancer is provided comprising (a) administering an oncolytic virus (b) measuring the level of one or more Th1 biomarkers and/or antibodies against one or more tumor associated antigens at a first time point and at a subsequent second time point and (c) comparing the level of one or more Th1 biomarkers and/or antibodies against one or more tumor antigens at the first time point and the second time point wherein a decrease in one or more Th1 biomarkers and/or an increase in antibodies against one or more tumor antigens at the second time point compared to the first time point or compared to the level of the same Th1 biomarkers and/or antibodies in another patient with the same cancer and administered the same oncolytic virus indicates that the patient is non-responsive to treatment with the oncolytic virus. Onocolytic virus therapy may be discontinued in patients identified as non-responsive to the virus; alternatively, one or more agents that produce a Th1 phenotype may be co-administered to the patient with the virus.

In one aspect, biomarkers of Th1 immune status (i.e. Th1 biomarkers) include, without limitation, immunomodulators such as IL-1β, IL-2, IL-8, IL-12, IL-18, IFN-γ, TNF-α, TNF-β, GM-CSF, cleaved caspase-3, neopterin, and β2-microglobulin. Th1 biomarkers may be used alone or in any combination according to the methods described herein. In a preferred embodiment, the expression of at least 1, at least 2, at least 3, at least 4, at least 5, at least 6, at least 7, at least 8, at least 9, at least 10, at least 11 or all 12 Th1 biomarkers selected from the group consisting of IL1β, IL-2, IL-8, IL-12, IL-18, IFN-γ, TNF-α, TNF-β, GM-CSF, cleaved caspase-3, neopterin, and β2 microglobulin is measured in a test sample from a patient. In a particularly preferred embodiment, the expression of IL-12 and optionally at least 1, at least 2, at least 3 at least 4, at least 5, at least 6, at least 7, at least 8, at least 9, or at least 10 biomarkers selected from the group consisting of IL1β, IL-2, IL-8, IL-18, IFN-γ, TNF-α, TNF-β, GM-CSF, cleaved caspase-3, neopterin, and β2 microglobulin is measured in a test sample from a patient. In other preferred embodiments, the expression of at least 1, 2, 3, 4, 5, 6, 7 or all 8 Th1 biomarkers selected from the group consisting of IL1β, IL-2, IL-8, IL-12 IFN-γ, TNF-α, GM-CSF, and cleaved caspase-3 is measured in a test sample from a patient. Elevated expression of any (and preferably of the majority or all) of these biomarkers relative to a predetermined control indicates an increased likelihood that the patient will respond to oncolytic virus therapy. It should be understood that if, for example 10 Th1 biomarkers are assessed in a test sample from the patient, a high level of 1, 2, 3, 4, 5, 6, 7, 8, or 9 of these biomarkers, in any combination, or a high level of all 10 of these biomarkers, indicates that the patient is likely to respond favorably to oncolytic virus therapy.

In other aspects, biomarkers of Th2 immune status (i.e. Th2 biomarkers) include, without limitation, IL-4, IL-5, IL-6, IL-10, IL-13, TGF-β and phosphorylated STAT3. Th2 biomarkers may be used alone or in any combination according to the methods described herein. Preferably, at least one, at least 2, 3, 4, 5, or at least 6 Th2 biomarkers selected from the group consisting of IL-4, IL-5, IL-6, IL-10, IL-13, TGF-β and phosphorylated STAT3 are measured in a test sample from a patient. It should be understood that if, for example 5 Th2 biomarkers are assessed in a test sample from the patient, a high level of 1, 2, 3, or 4 of these biomarkers, in any combination, or a high level of all 5 of these biomarkers, indicates that the patient is unlikely to respond favorably to oncolytic virus therapy.

In related embodiments, the expression of at least 1, 2, 3, 4, 5, 6, 7, or all 8 Th1 biomarkers selected from the group consisting of IL1β, IL-2, IL-8, IL-12, IFN-γ, TNF-α, GM-CSF and cleaved caspase-3, and at least one, at least two or all three Th2 biomarkers selected from the group consisting of IL-6, IL-10 and phosphorylated STAT3 (Tyr 705) are measured in a test sample from a patient according to the methods of the invention. In a particularly preferred embodiment, the methods comprise measuring the expression of IL-12 and optionally at least 1, 2, 3, 4, 5, 6, or all 7 biomarkers selected from the group consisting of IL1β, IL-2, IL-8, IFN-γ, GM-CSF, TNF-α and cleaved caspase-3, and measuring the expression of at least 1, 2, or all 3 biomarkers selected from the group consisting of IL-6, IL-10 and phosphorylated STAT3 (Tyr 705). Elevated expression of any (and preferably all) of the Th1 biomarkers and similar or decreased expression of any (and preferably all) of the Th2 biomarkers relative to a predetermined controls indicates an increased likelihood that the subject will respond to oncolytic virus therapy. Preferably, the expression of the Th1 biomarkers and the Th2 biomarkers is calculated and a ratio of Th1/Th2 biomarker expression is calculated, whereby a ratio higher than that of a predetermined control indicates an increased likelihood that the subject will respond to oncolytic virus therapy. For example, a ratio above 0.2, 0.5, 0.75, 1.0, 1.5, 2.0, 2.5, 3.0, 3.5, 4.0, 5.0 or more indicates an increased likelihood that the subject will respond to oncolytic virus therapy. In a related embodiment, the method comprises measuring the expression of IL-12 and optionally IL-6 or IL-10 in a test sample from the subject, wherein an increased ratio of IL-12/IL-6 and/or IL-12/IL-10 expression relative to a predetermined control indicates an increased likelihood that the subject will respond to oncolytic virus therapy.

In another aspect, biomarkers of Th1 immune status include cell surface markers including, without limitation, CXCR3, CCR5, CCR1 and IL-12 receptor β1 and α chains. In other aspects, biomarkers of Th2 immune status include, without limitation, cell surface markers including, without limitation, CXCR4, CCR3, CCR4, CCR7, CCR8, IL-1 receptor and CD30.

In another aspect, biomarkers that may be measured as a means for determining the immune status of a patient with cancer include without limitation, antibodies against tumor associated antigens (e.g. cancer/testis antigens) selected from the group consisting of BRAF, CABYR, CRISP3, CSAG2, CTAG2, DHFR, FTHL17, GAGE1, LDHC, MAGEA1, MAGEA3, MAGEA4, MAGEB6, MAPK1, MICA, MUC1, NLRP4, NYES01, P53, PBK, PRAME, SOX2, SPANXA1, SSX2, SSX4, SSX5, TSGA10, TSSK6, TULP2, XAGE2, and ZNF165. Anti-tumor associated antigen antibody biomarkers may be used alone or in any combination according to the methods described herein. Thus, the expression level of antibodies against at least 1, at least 2, at least 3, 4, 5, 6, 7, 8, 9, 10, 11, 12, 13, 14, 15, 16, 17, 18, 19, 20, 21, 22, 23, 24, 25, 26, 27, 28, 29 or at least 30 tumor associated antigens selected from the group consisting of: BRAF, CABYR, CRISP3, CSAG2, CTAG2, DHFR, FTHL17, GAGE1, LDHC, MAGEA1, MAGEA3, MAGEA4, MAGEB6, MAPK1, MICA, MUC1, NLRP4, NYES01, P53, PBK, PRAME, SOX2, SPANXA1, SSX2, SSX4, SSX5, TSGA10, TSSK6, TULP2, XAGE2, and ZNF165 may be measured in a test sample according to the methods described herein. Preferably, the expression level of antibodies against at least one, at least 2, 3, 4, 5, 6, 7, 8, or at least 9 tumor associated antigens selected from the group consisting of: CABYR, MAGEA1, MAGEA3, MAGEB6, NLRP4, NYESO1, PBK, SSX2, SSX5, and ZNF165 is measured in a test sample from the patient. In related embodiments, the expression level of antibodies against NLRP4 and optionally at least one, 2, 3, 4, 5, 6, 7, or at least 8 tumor associated antigens selected from the group consisting of CABYR, MAGEA1, MAGEA3, MAGEB6, NYESO1, PBK, SSX2, SSX5, and ZNF165 is measured in a test sample from the subject. A high level of expression of one or more of these tumor associated antigens compared to a control level indicates that the patient is unlikely to respond to oncolytic virus therapy. It should be understood that if, for example antibodies against 9 tumor associated antigens (biomarkers) are assessed in a test sample from the patient, a high level of 1, 2, 3, 4, 5, 6, 7 or 8 of these biomarkers, in any combination, or a high level of all 9 of these biomarkers, indicates that the patient is unlikely to respond favorably to oncolytic virus therapy.

In related embodiments, the expression of at least 1, 2, 3, 4, 5, 6, 7, or all 8 Th1 biomarkers selected from the group consisting of IL1β, IL-2, IL-8, IL-12, IFN-γ, TNF-α, GM-CSF and cleaved caspase-3, and the expression of antibodies against at least 1, at least 2, at least 3, 4, 5, 6, 7, 8, 9, 10, 11, 12, 13, 14, 15, 16, 17, 18, 19, 20, 21, 22, 23, 24, 25, 26, 27, 28, 29 or at least 30 tumor associated antigens selected from the group consisting of: BRAF, CABYR, CRISP3, CSAG2, CTAG2, DHFR, FTHL17, GAGE1, LDHC, MAGEA1, MAGEA3, MAGEA4, MAGEB6, MAPK1, MICA, MUC1, NLRP4, NYES01, P53, PBK, PRAME, SOX2, SPANXA1, SSX2, SSX4, SSX5, TSGA10, TSSK6, TULP2, XAGE2, and ZNF165 are measured in a test sample from a patient according to the methods of the invention. In a particularly preferred embodiment, the methods comprise measuring the expression of IL-12 and optionally at least 1, 2, 3, 4, 5, 6, or all 7 biomarkers selected from the group consisting of IL1β, IL-2, IL-8, IFN-γ, GM-CSF, TNF-α and cleaved caspase-3, and measuring the expression of antibodies against at least one, at least 2, 3, 4, 5, 6, 7, 8, or at least 9 tumor associated antigens selected from the group consisting of: CABYR, MAGEA1, MAGEA3, MAGEB6, NLRP4, NYESO1, PBK, SSX2, SSX5, and ZNF165. Elevated expression of any (and preferably all) of the Th1 biomarkers and/or decreased expression of any (and preferably all) of the antibodies against tumor associated antigens relative to a predetermined controls indicates an increased likelihood that the subject will respond to oncolytic virus therapy.

In a preferred embodiment, the test sample obtained from the patient is a serum sample and the level of IL-12 and optionally at least one additional Th1 biomarker is determined e.g. by ELISA. Alternatively or additionally the level of at least one Th2 biomarker and/or the level of antibody against NLRP4 and optionally at least one additional tumor associated antigen is measured in a serum sample from the patient.

In yet another aspect, the immunologic status of the patient is determined by measuring the level of one or more Th1 biomarkers and the level of antibodies against one or more tumor antigens as described above in a test sample (e.g. serum) from a patient prior to or during oncolytic virus therapy. Thus, a patient with a low level of one or more Th1 biomarkers (e.g. IL-12) and a high level of antibodies against one or more tumor antigens (e.g. NLRP4) compared to a control level of Th1 biomarkers and antibodies against one or more tumor antigens is unlikely to respond to oncolytic virus therapy. Conversely, a patient with a high level of one or more Th1 biomarkers and a low level of antibodies against one or more tumor antigens compared to a control level is likely to respond favorably to oncolytic virus therapy.

In other related aspects, the method comprises isolating lymphocytes from a tissue sample from the subject. In one aspect, the concentration of $CD4^+$ and $CD8^+$ T cells is measured (e.g. by flow cytometric analysis following treatment with anti-CD4 and anti-CD8 antibodies) and a ratio of $CD8^+/CD4^+$ cells in the test sample is calculated, whereby an increased ratio of $CD8^+/CD4^+$ cells in the test sample relative to a predetermined control indicates an increased likelihood that the subject will respond to oncolytic virus therapy. In another aspect, lymphocytes are isolated from a tissue sample from the subject and a ratio of $FoxP3^-/FoxP3^+$ cells is calculated, whereby an increased ratio of $FoxP3^-/FoxP3^+$ cells in the test sample relative to a predetermined control indicates an increased likelihood that the subject will respond to oncolytic virus therapy. FoxP3 is predominantly expressed on and therefore serves as a marker for regulatory T cells which act to suppress cell mediated immunity. Optionally, FoxP3 is measured along with CD25 and CD4 as a method for determining the level of regulatory T cells. CD4+, CD8+ or regulatory T cells can be detected for example with anti-FoxP3, anti-CD4, anti-CD8, anti-CD38, and anti-HLA-DR antibodies. Surface marker profiles specific for T cell subsets are known in the art.

In related aspects, the method comprises measuring in at least one test sample from a subject (i) the percentage of $CD4^+$ cells, $CD8^+$ cells and optionally $FOXP3^+$ cells relative to total lymphocytes in the sample and (ii) the level of antibodies against at least one tumor associated antigen and/or (iii) the level of at least one Th1 biomarker, whereby a percentage of $CD4^+$ and/or $FoxP3^+$ cells greater than 50, 60, 70, 80 or 90% of total lymphocytes and a high level of antibody against at least one tumor associated antigen and/or a low level of Th1 biomarker relative to a predetermined control indicates that the subject is unlikely to respond to oncolytic viral therapy. Conversely, a higher percentage of $CD8^+$ cells relative to $CD4^+$ and/or $FoxP3^+$ cells and/or a low level of antibody against at least one tumor associated antigen and/or a high level of Th1 biomarker relative to a predetermined control indicates that the subject is likely to respond to oncolytic viral therapy.

In another embodiment, a method for treating cancer in a subject is provided comprising the following steps: (a) administering to the subject an oncolytic virus for a treatment period (b) measuring one or more Th1 and/or Th2 biomarkers in a test sample from the subject at least twice during the treatment period and (c)(1) co-administering a Th1 stimulating agent with the oncolytic virus or (c)(2) discontinuing administration of the oncolytic virus if a decrease in the level of one or more Th1 biomarkers is detected. Optionally, one or more Th1 and/or Th2 biomarkers are measured in a test sample just before or at the beginning of the treatment period in order to provide a baseline measurement. A reduction in one or more Th1 biomarkers during the treatment period indicates a need for either co-administration of a Th1 stimulating agent with the virus or termination of oncolytic virus therapy, particularly if the level of one or more Th2 biomarkers is not reduced (e.g. remains substantially the same or increases).

Test samples obtained from a subject according to the methods, include without limitation, one or more samples obtained from tissue (e.g. tumor biopsy), cerebrospinal fluid (CSF), lymph, blood, plasma, serum, peripheral blood mononuclear cells (PBMCs), lymph fluid, lymphocytes, synovial fluid and urine. In particular embodiments, the test sample is obtained from CSF or tumor tissue. In other particular embodiments, the test sample is obtained from tumor tissue and e.g. the relative number of CD4+ and/or CD8+ cells in the sample is determined and/or the level of one or more Th1 and/or Th2 cytokines in the sample is measured e.g. by immunofluorescent staining of fixed and permeabilized cells from the sample with antibodies against the Th1 and/or Th2 cytokines. In other particular embodiments, the test sample is obtained from blood and e.g. the level of one or more Th1 and/or Th2 cytokines in the sample is measured by ELISA.

In a broad aspect, the present invention also provides a combination therapy for treating cancer in a patient comprising co-administering the patient an oncolytic virus and one or more agents that produce a Th1 immune phenotype. This methodology of using both oncolytic viruses (e.g. adenoviruses) and immune stimulatory agents is counterintuitive since activating the immune system could potentially reduce the level of oncolysis produced by viruses such as Delta-24-RGD. An activated immune system would be expected to clear the virus at an accelerated rate and thus reduce the effectiveness of the oncolytic virus therapy. Indeed, evidence suggests that slowing the development of Th1 responses is important for the efficacy of oncolytic therapy. The present inventors, however, have surprisingly discovered that the patients who exhibit strong tumor responses radiographically as well as prolonged survival show virus replication, immune stimulation, and activation of T-cell mediated cytotoxicity. Contrariwise, the present inventors have surprisingly discovered that patients demonstrating a relatively strong Th1 profile are more likely to exhibit a positive response to oncolytic therapy.

The agent that produces a Th1 immune phenotype in the patient can be administered prior to, during or after administration of the oncolytic virus. In one embodiment, a patient with cancer that is determined to be at risk for not responding favorably to oncolytic virus therapy according to any of the methods heretofore described, is co-administered with the virus one or more Th1 stimulating agents in an amount sufficient to increase the level of one or more Th1 biomarkers of the invention and/or decrease the level of one or more Th2 biomarkers and/or decrease the level of antibodies against one or more tumor associated antigens. In a preferred embodiment, the patient is administered one or more agents that produce a Th1 immune phenotype prior to administration of the oncolytic virus in order to "prime" the patient's immune system to respond favorably to oncolytic virus therapy and therefore increase the likelihood that the patient will have a favorable clinical outcome. In another embodiment, a patient with cancer that is determined to be likely to respond favorably to oncolytic virus therapy according to any of the methods heretofore described, is co-administered with the virus one or more Th1 stimulating agents in an amount sufficient to increase the level of one or more Th1 biomarkers of the invention and/or decrease the level of one or more Th2 biomarkers and/or decrease the level of antibodies against one or more tumor associated antigens. In a preferred embodiment, the patient is administered one or more agents that produce a Th1 immune phenotype prior to administration of the oncolytic virus in order "prime" the patient's immune system in order to boost the anti-tumor response to the oncolytic virus.

Certain embodiments are directed to methods of treating cancer in a patient comprising administering (i) a replication competent oncolytic virus (e.g. adenovirus), and (ii) an agent that upregulates or activates the cellular immune system. The agent can be administered prior to, during or subsequent to administration of the virus. The upregulation or activation of the cellular immune system can be accomplished by either stimulating the cellular immune system or suppressing the inhibition of the cellular immune system. The methods can be used for the treatment of primary tumors or tumors formed from metastasis. In certain aspects, the virus further comprises a targeting moiety. In further aspects, the replication competent virus is an adenovirus such as delta-24. In still a further aspect, the delta-24 adenovirus comprises a targeting moiety. In certain aspects the targeting moiety is an RGD containing peptide. In certain aspects, the RGD or other naturally occurring cell surface binding peptide confers an immune privilege to the oncolytic virus enabling the virus to remain therapeutic during times of elevated immune system activity.

In one preferred embodiment, a method for treating cancer in a patient is provided comprising: (a) administering to the patient a cytokine (e.g. e.g. recombinant IL-12p70 or recombinant IFN-γ) or one or more agents (e.g. Revlimid or lenalidomide) to increase the production of Th1 cytokines such as IL-12p70 or IFN-γ (b) administering to the patient an oncolytic virus (e.g. Delta-24-RGD) and optionally (c) administering to the patient an agent to suppress regulatory T cells (e.g. temozolomide, cyclophosphamide, CCNU, BCNU, melphalan, busulfan) and/or stimulate a cell mediated immune response (e.g. Ipilimumab, Tremelimumab, MDX-1106, MK-3475, AMP-224, Pidilizumab, MDX-1105). Preferably the oncolytic virus is administered by intratumoral injection into one or multiple areas of the tumor. The patient may have been previously determined by methods of the invention to be likely to respond to oncolytic virus therapy or alternatively may have been previously determined to be unlikely to respond to oncolytic virus therapy. Preferably, the cytokine or agent to increase production of Th1 cytokines is administered prior to the oncolytic virus and the agent to suppress regulatory T cells and/or stimulate a cellular immune response is administered during or subsequent to oncolytic virus therapy. In a related embodiment, step (a) further or alternatively comprises administering one or more agents to suppress the production of Th2 cytokines such as IL-10 and IL-4.

In certain aspects the agent that produces a Th1 phenotype is administered to the patient 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 or more days, 1, 2, 3, 4 weeks or 1, 2, 3, 4, 5, 6 months, including all values and ranges there between, prior to or after administration of the oncolytic virus. In a preferred embodiment, the agent that produces a Th1 phenotype is administered prior to administration of the oncolytic virus and optionally is continued after administration of the virus. In one embodiment, the agent that that produces a Th1 phenotype is administered to the patient between 1 and 14 days prior to or after administration of the oncolytic virus. In another embodiment, the agent is administered between 1 and 4 weeks prior to or after administration of the oncolytic virus. In other embodiments, the agent is simultaneously co-administered to the patient with the oncolytic virus.

In certain aspects, an assessment of cellular immune function will be carried out prior to, during, or after administration of the oncolytic virus or the immune activation agent e.g. by measuring the level of one or more Th1 and/or Th2 biomarkers as described herein and/or antibodies to one or more tumor related antigens in the blood. Alternatively, immune cell infiltrates such as antigen presenting cells (e.g. macrophages, dendritic cells, astrocytes and microglia), cytotoxic T cells, or natural killer cells can be detected in biopsy samples from a tumor.

In one aspect, a concentration of tumor infiltrating $CD4^+$ and $CD8^+$ lymphocytes is assessed, wherein a patient with a high $CD4^+/CD8^+$ ratio compared to a control (indicating a Th2 profile) is simultaneously, separately or consecutively co-administered a replication competent oncolytic virus and an agent that upregulates or activates the cellular immune system. In another aspect, the relative number of Th1/Th2 CD4+ cells in a test sample (e.g. biopsy or peripheral blood mononuclear cells) from the subject is determined by measuring co-expression of CD4 and one more Th1 cytokines (e.g. IL-12p70 or IFN-γ) and Th2 cytokines (e.g. IL-4) and determining the relative number of Th1/Th2 CD4+ cells. Preferably, the cells are stimulated (e.g. with Phorbol ester plus Ionomycin), fixed, permeabilized, stained with appropriate antibodies and subjected to flow cytometric analysis. In one embodiment, one or more cytokine levels indicative of a Th1 profile can be measured in the blood, serum or other fluids. In one aspect, a patient with a low level of Th1 cytokines compared to an appropriate control or a high level of Th2 cytokines compared to an appropriate control is co-administered a replication competent oncolytic virus, and an agent that upregulates or activates the cellular immune system.

In a related embodiment, one or more Th1 cytokines selected from the group consisting of IL1β, IL-2, IL-8, IL-12, IL-18, IFN-γ, TNF-α, TNF-β and GM-CSF are measured. Other Th1 biomarkers such as cleaved caspase-3, neopterin and β2 microglobulin may also be measured as part of a Th1 profile. In another related embodiment, one or more Th2 cytokines selected from the group consisting of IL-4, IL-5, IL-6, IL-10 and IL-13 and TGF-β are measured. Other Th2 biomarkers such as phosphorylated STAT3 (Tyr 705) may also be measured as part of a Th2 profile. In other aspects, cytokines or other biomarkers indicative of a Th1 and/or Th2 profile are monitored during oncolytic virus (e.g. adenovirus) therapy wherein a patient exhibiting a shift from a Th1 profile to a Th2 profile during therapy is administered an agent that upregulates or activates the cellular immune system. Therapy induced necrosis can be detect and/or measured.

In certain embodiments the agent that produces a Th1 phenotype (upregulates or activates the cellular immune system) is an antagonist of a suppressor of cellular immunity (antagonist of cellular immune-suppression). Antagonists of cellular immune-suppression are agents that act on cells or molecules that suppress the cellular immune system. Antagonists of cellular immune-suppression include cytotoxic T-lymphocyte antigen 4 (CTLA-4; also known as CD152) antagonists such as Ipilimumab (also known as Yervoy™, MDX-010 or MDX-101; a humanized monoclonal antibody against CTLA-4 developed by Bristol-Myers Squibb) and Tremelimumab (formerly ticilimumab, CP-675, 206; a humanized monoclonal antibody against CTLA-4 MedImmune/AstraZeneca); PD-1/PD-L1-receptor antagonists such as MDX-1106 (an α-PD-1 humanized monoclonal antibody, Bristol-Myers Squibb); MK-3475 (an α-PD-1 humanized monoclonal antibody, Merck); AMP-224 (Fc-PD-1 fusion protein that blocks interaction between PD-1 and ligands B7-DC and B7-H1; Glaxo Smith Kline); Pidilizumab (also known as CT-011; a humanized monoclonal antibody against αPD-1, Chirotech); MDX-1105 (an α-PD-L1 humanized monoclonal antibody, Bristol-Myers Squibb); antibodies that specifically bind to B7-H3 such as MGA271 (an α-B7-H3 humanized monoclonal antibody, Microgenics) or other antibodies as described in US Application Publication Number 2012-0294796, the contents of which are incorporated herein by reference; or indoleamine-2,3-dioxygenase (IDO) inhibitors such as D-1-methyl-tryptophan (Lunate) and other compounds described in U.S. Pat. No. 7,799,776, the contents of which are incorporated herein by reference.

In certain embodiments, the agent that upregulates the cellular immune system is a cellular immune system stimulator. An immuno-stimulator is a small molecule, peptide, polypeptide (e.g. antibody), or cell that when introduced into a subject results in increases the activity of cell mediated immune response. Immuno-stimulators include co-stimulatory pathway agonists, such as CD137 agonists including without limitation BMS-663513 (an α-CD137 humanized monoclonal antibody agonist, Bristol-Myers Squibb); agonists to CD40, such as CP-870,893 (α-CD40 humanized monoclonal antibody, Pfizer); OX40 (CD134) agonists (e.g. anti-OX40 humanized monoclonal antibodies, AgonOx and those described in U.S. Pat. No. 7,959,925); or agonists to CD27 such as CDX-1127 (α-CD27 humanized monoclonal antibody, Celldex).

In certain aspects, an immune-stimulator is an agent that induces or stimulates antigen-presenting cells relative to Delta-24-RGD antigens, such as antagonists of CD47 or SIRPα by either monoclonal antibodies or small molecule inhibitors including without limitation SIRPαFc (Trillium Therapeutics Inc.) and other inhibitors as described in US Patent Publication Number 2012/0189625, the contents of which are incorporated herein by reference.

Small molecule inhibitors that disrupt the immuno-silencing of tumors include inhibitors of JAK-2, JAK-3, STAT-3, or STAT-5 such as Lestaurtinib (CEP-701 hydrate, (9S,10S,12R)-2,3,9,10,11,12-Hexahydro-10-hydroxy-10-(hydroxymethyl)-9-methyl-9,12-epoxy-1H-diindolo[1,2,3-fg:3′,2′,1′-kl]pyrrolo[3,4-i][1,6]benzodiazocin-1-one; Sigma-Aldrich; JAK-2 inhibitor), Pacritinib (SB1518; 11-(2-pyrrolidin-1-yl-ethoxy)-14,19-dioxa-5,7,26-triaza-tetracyclo[19.3.1.1(2,6).1(8,12)]heptacosa-1(25),2(26),3,5,8,10,12(27),16,21,23-decaene; JAK-2/FLT3 inhibitor), Tofacitinib (CP-690550; 3-[(3R,4R)-4-methyl-3-[methyl(7H-pyrrolo[2,3-d]pyrimidin-4-yl)amino]piperidin-1-yl]-3-oxopropanenitrile; JAK-3 inhibitor, Pfizer); Ruxolitinib ((3R)-3-cyclopentyl-3-[4-(7H-pyrrolo[2,3-d]pyrimidin-4-yl)pyrazol-1-yl]propanenitrile; JAK-1/JAK-2 inhibitor, Incyte and Novartis); CYT387 (JAK-2 inhibitor; N-(Cyanomethyl)-4-[2-(4-morpholinoanilino)pyrimidin-4-yl]benzamide; YM BioSciences); Baricitinib (LY3009104; 2-[1-ethylsulfonyl-3-[4-(7H-pyrrolo[2,3-d]pyrimidin-4-yl)pyrazol-1-yl]azetidin-3-yl]acetonitrile; JAK-1/JAK-2 inhibitor); and TG101348 (N-tert-Butyl-3-{5-methyl-2-[4-(2-pyrrolidin-1-yl-ethoxy)-phenylamino]-pyrimidin-4-ylamino}-benzenesulfonamide; JAK-2 inhibitor).

In further aspects patients with cancer can be administered one or more biological modifiers that produce a Th1 phenotype (activate the cellular immune response) such as cytokines (preferably recombinant) including without limitation GM-CSF, IL-2, IL-12, IL-18 and interferon-γ prior to or during oncolytic virus therapy in order to improve the patient's response to the virus. IFN-γ and IL-12 are known to inhibit production of Th2 cytokines and are therefore particularly preferred cytokines for activating the cellular immune response. Alternatively, these patients can be administered one or more agents that stimulate production of IL-12p70 and/or other Th1 cytokines such as lenalidomide (Revlimid), or pomalidomide. In a related aspect, these patients can alternatively or additionally be administered one or more agents that decrease T-regulatory cells such as alkylating agents including without limitation Temozolomide, cyclophosphamide, lomustine (CCNU), bis-chloroethylnitrosourea (BCNU), melphalan hydrochloride, busulfan (butane-1,4-diyl dimethanesulfonate), mechlorethamine (nitrogen mustard), chlorambucil, ifosfamide, streptozocin, dacarbazine (DTIC), thiotepa, altretamine (hexamethylmelamine), cisplatin, carboplatin, and oxalaplatin, prior to, during or after oncolytic virus therapy. In another related aspect, these patients can be administered one or more agents which neutralize Th2 cytokines such IL-4, IL-5, IL-6, IL-10 and IL-13, particularly IL-4 and IL-10 prior to or during oncolytic virus therapy; because these Th2 cytokines suppress the Th1 pathway, their neutralization should improve the patient's response to the virus.

The present inventors have discovered that administration of an alkylating agent such as temozolomide to a patient with cancer prior to administering an oncolytic virus such as Delta-24-RGD surprisingly increases the likelihood that the patient will respond favorably to the virus. Without being bound by theory, it is believed that lymphopenia induced in glioma patients following treatment with alkylating agents such as temozolomide may result in a shift in the tumor environment from a predominantly Th2 phenotype to a Th1 phenotype, thereby potentiating the tumor to treatment with an oncolytic virus. Thus, in a preferred embodiment of the invention, a method for treating cancer in a patient is provided comprising administering to the patient an alkylating agent and subsequently administering to the patient an oncolytic virus. Preferably, the patient is a patient with a primary or metastatic brain tumor such as a glioma, the virus is an adenovirus such as Delta-24 or Delta-24-RGD, and the alkylating agent is selected from the group consisting of Temozolomide, cyclophosphamide, lomustine (CCNU), bis-chloroethylnitrosourea (BCNU), melphalan hydrochloride and busulfan (butane-1,4-diyl dimethanesulfonate). In a particularly preferred embodiment, the alkylating agent is temozolomide. The alkylating agent can be administered 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 or more days, 1, 2, 3, 4 weeks or 1, 2, 3, 4, 5, 6 months, including all values and ranges there between, prior to administration of the oncolytic virus.

In other embodiments, the oncolytic virus is co-administered with one or more adjuvants which promote a Th1 response nonlimiting examples of which include monophosphoryl lipid A (MPL®), QS-21 (plant extract comprising soluble triterpene glucoside compounds) or other saponin, oligodeoxynucleotides comprising or consisting of CpG, and ribosomal protein extract (RPE).

In certain aspects the cancer to be treated according to the present methods is a cancer of the central nervous system. In related aspect, the cancer is a neuroepithelial tumor such as, without limitation, an astrocytic tumor (e.g. astrocytoma, anaplastic astrocytoma, glioblastoma, gliosarcoma, pilocytic astrocytoma, giant cell astrocytoma, pleomorphic xanthoastrocytoma), an oligodendroglioma, an ependymoma, an oligoastrocytoma, a spongioblastoma, an astroblastoma, a choroid plexus papiloma, a choroid plexus carcinoma, a gangliocytoma, a ganglioglioma, a neurocytoma, a neuroepithelial tumor, a neuroblastoma, a pineal region tumor (such as a pineocytoma, a pineoblastoma, or a mixed pineocytoma/pineobastoma), a medulloepithelioma, a medulloblastoma, a neuroblastoma or ganglioneuroblastoma, a retinoblastoma, or an ependymoblastoma. In another related aspect, the cancer is a central nervous system neoplasm such as, without limitation, a tumor of the sellar region (such as a pituitary adenoma, a pituitary carcinoma, or a craniopharyngioma), a hematopoietic tumor (such as a primary malignant lymphoma, a plasmacytoma, or a granulocytic sarcoma), a germ cell tumor (such as a germinoma, an embryonal carcinoma, a yolk sac tumor, a choriocarcinoma, a teratoma or a mixed germ cell tumor), a meningioma, a mesenchymal tumor, melanocytoma, or a tumor of cranial or spinal nerves (such as a schwannoma, or a neurofibroma). In a particular aspect, the cancer is a low-grade glioma (e.g. ependymoma, astrocytoma, oligodendroglioma or mixed glioma) or high-grade (malignant) glioma (e.g. glioblastoma multiforme). In another aspect, the cancer is a primary or metastatic brain tumor. In other aspects, the cancer is a primary or metastatic brain tumor comprising brain tumor cell stem cells. In a preferred embodiment, the cancer is a malignant glioma comprising brain tumor cell stem cells.

In other aspects, cancers to be treated according to the present methods include without limitation, lung, ovary, breast, cervix, pancreas, stomach, colon, skin, larynx, bladder, and prostate cancer. Preferably the cancer to be treated exhibits a disrupted Rb pathway. In yet other aspects, the oncolytic virus is administered to treat a hyperproliferative disorder such as metaplasias, dysplasias or hyperplasia.

In certain aspects, the oncolytic virus is an adenovirus such as Delta-24-RGD. Oncolytic adenoviruses such as Delta-24-RGD have the ability to replicate in a variety of cell lines including lung, breast, prostate, sarcomas and glioma stem-like cells. Thus, e.g. oncolytic adenoviruses such as Delta-24-RGD may be administered to a patient having any cancer permissive to replication of the virus in order to treat the cancer.

BRIEF DESCRIPTION OF THE DRAWINGS

FIG. 3. Correlation of anti-tumor associated antigen antibodies with tumor recurrence. The upper panel is a graph depicting the correlation of antibodies against tumor antigens with tumor recurrence in a glioma patient (Patient F). Antibodies against an array of tumor associated antigens (those described in FIG. 1) were measured in a serum sample from the patient at the end of Delta-24-RGD therapy and at 15 days, 1 month, 4 months and 6 months post therapy. No antibodies were detected at the 15 day or 1 month period. However, between the four month and six month period the number of positive antibodies jumped from two to twenty and coincided with recurrence of the tumor. The lower panel depicts a scan of Patient F at the end of Delta-24-RGD therapy (left) and at 6 months after therapy (right). The recurrence of tumor can be seen in the scan at the 6 month timepoint.

FIG. 4. Comparison of Patients G and I. A heat map depicting the results of a peptide array to detect antibodies against a panel of tumor associated antigens (those described in FIG. 1) in sera from two glioma patients (Patient G, a complete responder (left panel), and Patient I who progressed (right panel)) treated with Delta-42-RGD taken prior to treatment with the virus (0 months) and one, four and six months after treatment (Patient G) and one, three and four months after treatment (Patient I). The results depicted in the heat map are raw data obtained from absorbance analysis (i.e. not background subtracted). An average background of ~0.2 was observed and accordingly a cutoff that could be applied universally to all antigens for positive versus negative results was 3×background=0.6. Patient G survived is presently still alive over 30 months after treatment with the virus. Patient I deceased 6 months after therapy. Patient G had a score of 0 at each time point, (negative for antibodies in the serum against all of the 31 tumor associated antigens tested). Patient I on the other hand had a score of 10 prior to treatment with the virus (positive for antibodies against CABYR, MAGEA1, MAGEA3, MAGEB6, NLRP4, NYESO1, PBK, SSX2, SSX5 and ZNF165) and this number increased to 18 at the one month time point, 22 at the three month time point and 31 (i.e. antibodies against all tumor associated antigens tested) at the four month time point. This clearly demonstrates the usefulness of these tumor antigens as biomarkers for predicting the likelihood of response to oncolytic virus therapy such as Delta-42-RGD.

FIG. 7 is a graph (on a logarithmic scale) depicting IL-12p70 (picograms/ml) in sera of glioma patients treated with Delta-24-RGD prior to therapy (pre-op) and one month, two months and three months post treatment. Patients 12A, 30A and 33A had very high IL-12p70 levels at baseline (prior to treatment with the virus) and these levels increased after treatment with the virus. Patients 12A and 30A and 33A showed a complete response to the virus and this correlated with IL-12p70 levels both prior to and after treatment (IL-12p70 levels were over 100-fold and over 1000-fold higher in these patients relative to non-responders). On the other hand, the remaining patients depicted on the graph exhibited low levels of IL-12p70 prior to and after administration of the virus and did not respond to the virus. Patient 37A (not shown on the graph) had low baseline IL-12p70 levels and was given IFN-γ approximately 2 months after treatment with the virus to stimulate a Th1 immune response and increase IL-12p70 levels. Administration of IFN-γ to Patient 37A caused a significant increase in IL-12p70 levels (indicating a switch to a Th1 immune response) and corresponded with a complete response to the virus. Thus, IL-12p70 levels (e.g. pretreatment) correlate very well with treatment outcome, with responders having high levels of IL-12 both prior to and during therapy. Conversely, non-responders had low levels of IL-12 prior to and during therapy. Strikingly, administration of the Th1 stimulating agent IFN-γ to a patient exhibiting low IL-12p70 levels boosted IL-12p70 levels in the patient and a complete response to the virus was observed in the patient.

DESCRIPTION

Definitions

Figure 1:
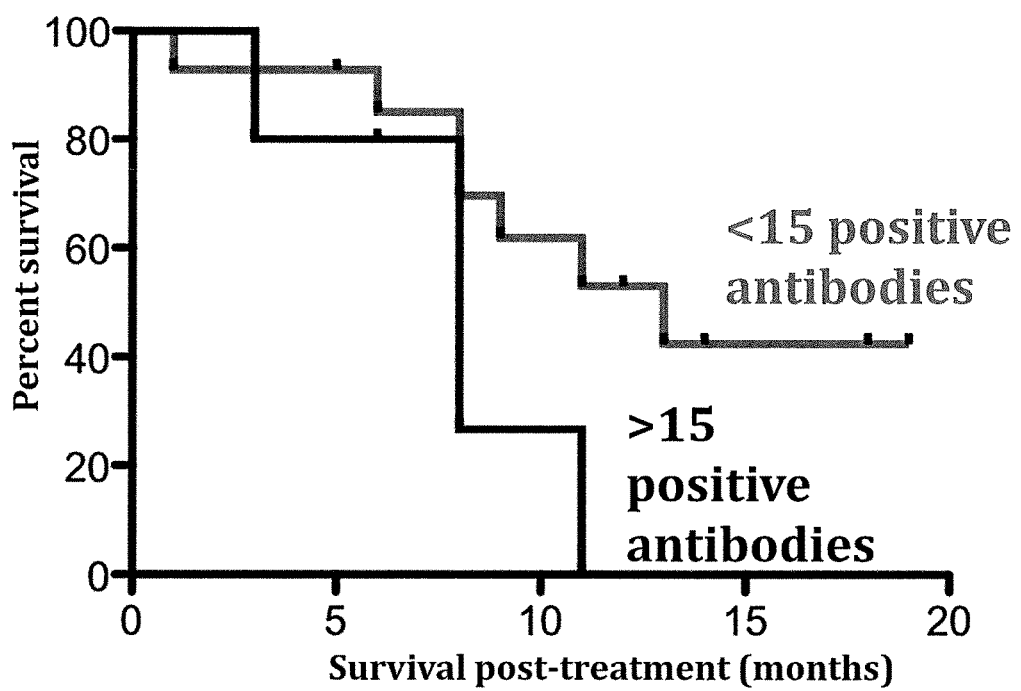
FIG. 1. Antibodies vs. Survival (Humoral vs Cellular skew). A graph depicting the correlation between antibodies against tumor associated antigens and survival in patients with gliomas treated with oncolytic adenovirus (Delta-24-RGD). Briefly, serum from a subset of 20 glioma patients was assessed prior to Delta-24-RGD therapy for antibodies against 31 tumor associated antigens including BRAF, CABYR, CRISP3, CSAG2, CTAG2, DHFR, FTHL17, GAGE1, LDHC, MAGEA1, MAGEA3, MAGEA4, MAGEB6, MAPK1, MICA, MUC1, NLRP4, NYES01, P53, PBK, PRAMS, SOX2, SPANXA1, SSX2, SSX4, SSX5, TSGA10, TSSK6, TULP2, XAGE2, and ZNF165 by automated protein microarray using a modified solid-phase ELISA (Serametrix). Over 40% of patients with fewer than 15 positive antibodies survived more than 20 months after treatment whereas every patient with more than 15 positive antibodies did not survive past 11 months. Moreover, those patients with fewer than 15 positive antibodies who did not survive more than 20 months experienced an improved clinical outcome relative to those having more than 15 positive antibodies.
Figure 2:
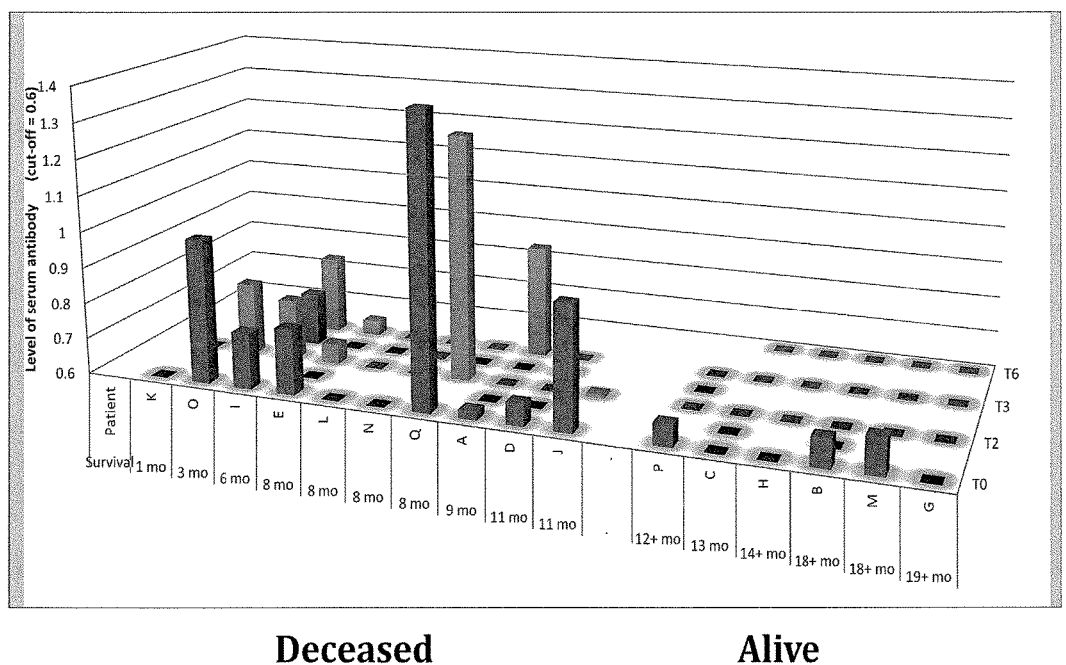
FIG. 2. Immunity to antigen NLRP4 vs. survival. A graph depicting immunity to tumor associated antigen NLRP4 as a function of survival in glioma patients treated with Delta-24-RGD. Antibodies against NLRP4 were assessed in sera from glioma patients prior to administering the virus and at several time points thereafter generally in monthly intervals. Patients K, O, I, E, L, N, Q, A, D and J, surviving between 1 month and 11 months post treatment, experienced a relatively high level of antibodies against NLRP4 whereas patients P, C, H, B, M and G, surviving from more than 12 months to more than 19 months post treatment, experienced very low to undetectable levels of antibodies against NLRP4. Patient G exhibited a complete response to the therapy.
Figure 5:
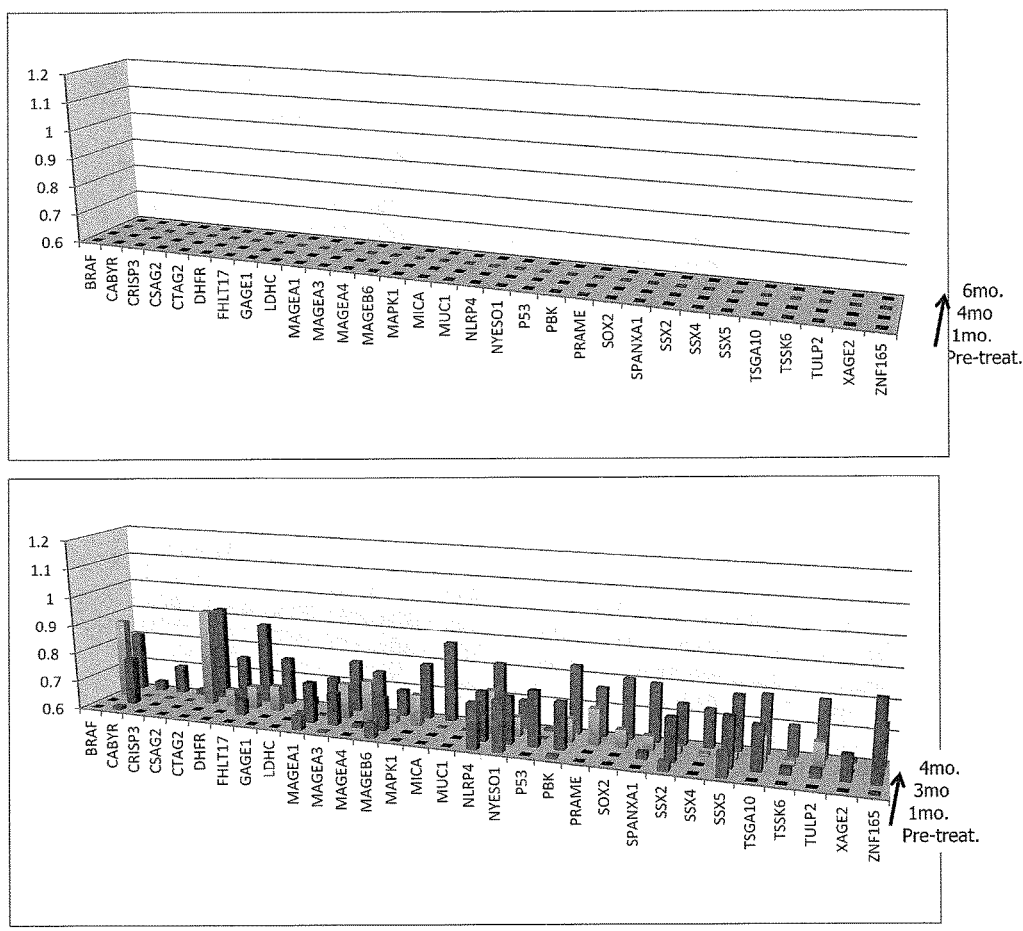
FIG. 5. A graph depicting the results of the peptide analysis described in FIG. 4. The upper panel illustrates the results of serum analysis from Patient G, a complete responder. The lower panel illustrates the results of serum analysis from Patient I who did not respond. Serum samples were obtained and analyzed for antibodies reactive against the specified tumor associated antigens pre-treatment (both patients) with the virus and one month, four months and six months after treatment with the virus (Patient G) and one month, three months and four months after treatment with the virus (Patient I). Antibody levels are on the "y" axis; antigens are on the "x" axis. Patient G was negative for all 31 antibodies both prior to and after treatment with the virus. Patient H was positive for 10 antibodies prior to treatment with the virus and was positive for all 31 antibodies at the four month time point.
Figure 6:
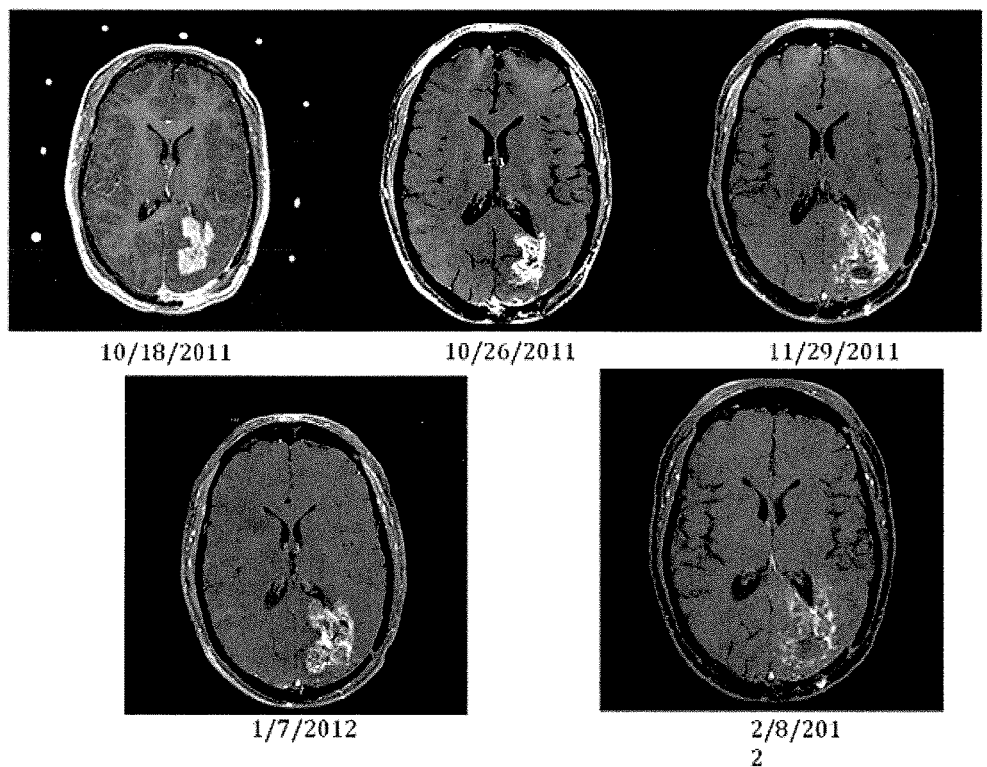
FIG. 6. Brain scans from a glioma patient (Patient 30A) who exhibited very high levels of IL-12p70 prior to treatment with Delta-42-RGD are depicted. The upper left scan demonstrates the glioma in the patient prior to administering Delta-42-RGD therapy (Nov. 18, 2011). The upper middle scan demonstrates a positive response in the tumor eight days after therapy (Oct. 26, 2011) and eleven days after therapy (Oct. 29, 2011). The bottom left scan demonstrates the response nearly two months after therapy (Jan. 7, 2012) and nearly three months after therapy (Feb. 8, 2012).
Figure 7:
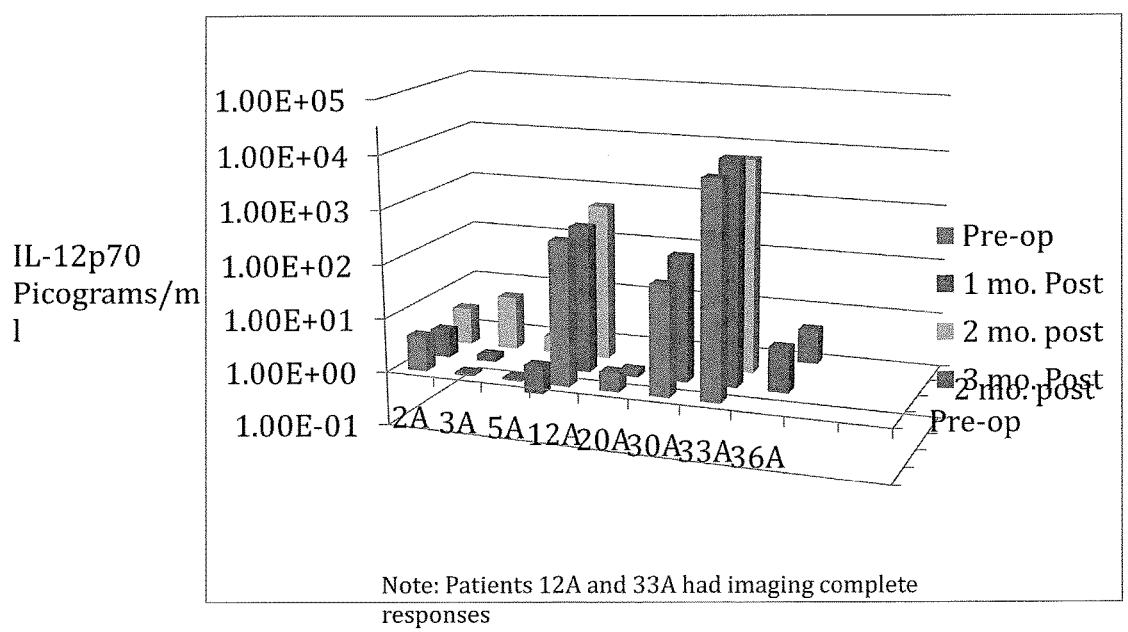
FIG. 7. Measurement of IL-12p70 (in picograms/ml) in patient sera samples.

As used herein, the term "antigen" is a molecule capable of being bound by an antibody or T-cell receptor. An antigen is additionally capable of inducing a humoral immune response and/or cellular immune response leading to the production of B- and/or T-lymphocytes. The structural aspect of an antigen, e.g., three dimensional conformation or modification (e.g., phosphorylation) that gives rise to a biological response is referred to herein as an "antigenic determinant" or "epitope." B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant need not be a contiguous sequence or segment of protein and may include various sequences that are not immediately adjacent to one another. In certain aspects, Tau oligomers are utilized as antigens.

The term "antibody" or "immunoglobulin" is used to include intact antibodies and binding fragments/segments thereof. Typically, fragments compete with the intact antibody from which they were derived for specific binding to an antigen. Fragments include separate heavy chains, light chains Fab, Fab', F(ab')2, Fabc, and Fv. Fragments/segments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes a bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann (1990); Kostelny et al. (1992).

In one aspect, the term "control" or "predetermined control" as used herein refers to a baseline level of a Th1 and/or Th2 biomarker and/or antibody against a tumor associated antigen as determined from one, or preferably an average obtained from more than one, "normal" or "healthy" subjects believed not to or confirmed by diagnosis not to have a cancer. Once a level has become established for a standard population, results from test samples can be directly compared with the predetermined control. For example, a baseline may be obtained from at least one subject and preferably is obtained from an average of subjects, wherein the subject or subjects have no prior history of cancer. By way of example, a level of a Th1 biomarker such as IL-12p70 in a serum sample from a patient may be compared to the serum level of the same Th1 biomarker in an undiseased subject or an average serum level of more than one undiseased subjects.

In another aspect, the term "control" or "predetermined control" refers to a baseline level of a Th1 and/or Th2 biomarker and/or antibody against a tumor associated antigen as determined from an average value in subjects having the same type of cancer as the patient to be treated. By way of example, a level of a Th1 biomarker such as IL12p70 in a serum sample from a patient may be compared to an average serum level obtained from multiple subjects with the same type of cancer as the patient to be treated. Glioma patients generally exhibit IL-12p70 serum levels in the range of 10-20 picograms/ml.

In a related aspect, the term "control" or "predetermined control" refers to a level of a Th1 and/or Th2 biomarker and/or antibody against a tumor associated antigen in one subject, or preferably an average level of more than one subject, having the same type of cancer as the patient to be treated who have been administered the same oncolytic virus and shown to have not responded to the virus. For example, a level of a Th1 cytokine such as IL-12p70 in a serum sample from the patient is compared to an average serum level obtained from more than subject with the same type of cancer who did not respond to the virus, whereby a high level of the Th1 cytokine compared to the average level from non-responders indicates that the patient is likely to respond favorably to the virus.

In another related aspect, the term "control" or "predetermined control" refers to a level of biomarker in one subject, or preferably an average level of more than one subject, having the same type of cancer as the patient to be treated who have been administered the same oncolytic virus and shown to have responded well to the virus. For example, a level of a Th1 cytokine such as IL-12p70 in a serum sample from the patient is compared to an average serum level obtained from more than subject with the same type of cancer who responded well to the virus, whereby a low level of the Th1 cytokine compared to the average level from good responders indicates that the patient is unlikely to respond favorably to the virus.

For purposes of comparison, the level of Th1 and/or Th2 biomarker and/or antibody against a tumor associated antigen in a test sample to be measured is of the same type (obtained from the same biological source) and is processed in the same way as what is used for determination of the baseline control level. For example, if a level of IL-12p70 is determined in by measuring the level of IL-12p70 in serum, the baseline level of IL-12p70 is determined by measuring the level of IL-12p70 in serum from e.g. normal healthy subjects. As used herein, a "high" level or an "increase" in the measured level of a Th1 biomarker relative to a predetermined control means that the amount or concentration of Th1 biomarker in a test sample is sufficiently greater in the test sample relative to the predetermined control level of Th1 biomarker. For example, an increase in the level of a Th1 biomarker relative to a predetermined control may be any statistically significant increase which is detectable such as without limitation, about a 1%, about a 5%, about a 10%, about a 15%, about a 20%, about a 30%, about a 40%, about a 60%, about an 80%, about a 2-fold, about a 3-fold, about a 5-fold, about an 8-fold, about a 10-fold, about a 20-fold 50-fold, 100-fold, 200-fold, 500-fold or even 1000-fold elevation or more relative to the predetermined control. In another aspect, a "high level" of biomarker in a test sample compared to control may refer to a detection level of an antibody above a predetermined threshold wherein the control level is below the predetermined threshold.

The term "correlate" or "correlation" or equivalents thereof refer to an association between expression of one or more genes or proteins and a treatment outcome of a cancer cell and/or cancer patient in comparison to the lack of response. The invention provides for the correlation between increases in expression of one or more of the herein disclosed biomarkers and responsiveness of a cancer patient to oncolytic virus therapy.

The term "glioma" refers to a tumor originating in the neuroglia of the brain or spinal cord. Gliomas are derived from the glial cell types such as astrocytes and oligodendrocytes, thus gliomas include astrocytomas and oligodendrogliomas, as well as anaplastic gliomas, glioblastomas, and ependymomas. Astrocytomas and ependymomas can occur in all areas of the brain and spinal cord in both children and adults. Oligodendrogliomas typically occur in the cerebral hemispheres of adults. Other brain tumors are meningiomas, ependymomas, pineal region tumors, choroid plexus tumors, neuroepithelial tumors, embryonal tumors, peripheral neuroblastic tumors, tumors of cranial nerves, tumors of the hemopoietic system, germ cell tumors, and tumors of the stellar region.

The term "IL-12p70" or "IL-12" refers to the biologically active form of IL-12, a 70 kDa (p70) cytokine produced mainly be monocytes, macrophages, B-lymphocytes and dendritic cells. IL-12 is a heterodimer composed of two subunits, one 40 kDa (p40) and the other 35 kDa (p35) linked together by disulfide bonds.

As used herein the term "normal" in the context of a diagnosis or prognosis refers to an individual or group of individuals who have not shown any symptoms of cancer and are not known to suffer from the disorder. Preferably, the normal individual(s) is not on medication for treating cancer and if possible has not been diagnosed with cancer or any other hyperproliferative disorder. "Normal" according to the invention also refers to samples isolated from normal individuals.

The term "oncolytic virus" refers generally to any virus capable of replicating in and killing tumor cells. Preferably, the virus is engineered e.g. to increase tumor cell selectivity. Representative examples of oncolytic virus include without limitation, adenovirus, reovirus, herpes simplex virus (HSV), Newcastle disease virus, poxvirus, myxoma virus, rhabdovirus, picornavirus, influenza virus, coxsackievirus and parvovirus. In preferred embodiments, the oncolytic virus is a vaccinia virus (e.g. Copenhagen, Western Reserve, Wyeth strain), rhabdovirus (e.g. vesicular stomatitis virus (VSV)), or adenovirus (e.g. ONYX-015, Delta-24-RGD). In a particularly preferred embodiment, the oncolytic virus is an adenovirus. A preferred adenovirus is Delta-24-RGD. Delta-24-RGD is a tumor-selective adenovirus serotype 5 strain comprising a 24 base-pair deletion of the EIA region that encompasses the area responsible for binding Rb protein (nucleotides 923-946) corresponding to an eight amino-acids 120-127 in the encoded E1A protein (Fueyo J et al., Oncogene, 19:2-12 (2000)). Delta-24-RGD further comprises an insertion of the RGD-4C sequence (which binds strongly to $\alpha v\beta 3$ and $\alpha v\beta 5$ integrins) into the H1 loop of the fiber knob protein (Pasqualini R. et al., Nat Biotechnol, 15:542-546 (1997)). The E1A deletion increases the selectivity of the virus for cancer cells; the RGD-4C sequence increases the infectivity of the virus in gliomas.

The term "providing" is used according to its ordinary meaning to indicate "to supply or furnish for use." In some embodiments, a protein is provided directly by administering the protein, while in other embodiments, the protein is effectively provided by administering a nucleic acid that encodes the protein.

The term "respond" generally means that a patient exhibits a complete or partial response to the oncolytic therapy as defined in the Response Evaluation Criteria in Solid Tumors (RECIST) criteria (Eisenhauer et al., European Journal of Cancer, 45:228-247 (2009), incorporated herein by reference). A complete response means a disappearance of all target lesions. A partial response means at least a 30% decrease in the sum of the longest diameter (LD) of target lesions, taking as a reference the baseline sum LD. In particular, a response generally refers to a complete or partial change in tumor size. Similarly, patients who fail to respond to oncolytic therapy are those that exhibit stable disease (neither sufficient shrinkage to qualify as a partial response nor sufficient increase to qualify as progressive disease) or progressive disease (at least a 20% increase in the sum of the LD of target lesions, taking as reference the smallest sum LD since the treatment started). The skilled clinician/radiologist will understand the appropriate methods for determining tumor measurements using e.g. computed tomography (CT) or magnetic resonance imaging (MRI), in conjunction with clinical assessment.

The term "therapeutic benefit" or "treatment" refers to anything that promotes or enhances the well-being of the subject with respect to the medical treatment of his/her condition, which includes treatment of pre-cancer, cancer, and hyperproliferative diseases. A list of nonexhaustive examples of this includes extension of the subject's life by any period of time, decrease or delay in the neoplastic development of the disease, decrease in hyperproliferation, reduction in tumor growth, delay of metastases, reduction in cancer cell or tumor cell proliferation rate, and a decrease in pain to the subject that can be attributed to the subject's condition. It is not necessary that the cancer be cured to accomplish a meaningful treatment, all that is required is that the cancer be slowed to some degree or some condition associated with the cancer is ameliorated.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

A common feature to both primary and metastatic tumors to the brain is a lack of immunosurveillance with these tumors. The normal antigen presenting cells within the brain, known as microglia, are frequently found to be "turned off" and therefore have a functional lack of antigen presentation activities to the immune system. This lack of immunosurveillance is thought to be one reason why these tumors are so difficult to treat.

Data from a phase-1 clinical trial for treating malignant glioma with an oncolytic adenovirus (Delta-24-RGD) that replicates within primary gliomas showed unexpectedly that an immune response was raised not only to adenoviral antigens but also cancer related antigens. Briefly, it has been discovered that these tumor associated antigens are released (or exposed) after the infection of Delta-24 in glioma cell lines. In addition, this phase-1 clinical study unexpectedly showed massive recruitment of a large population of cytotoxic T-cell infiltrates with large regions of treatment related necrosis. This finding suggests a process of not only active oncolysis with the Delta-24-RGD agent but also cell mediated cytotoxicity to the tumor cells. Without being bound by theory it is believed that, in patients for whom treatment with virus is successful, an initial immune response to the oncolytic virus is generated followed by a shift in immunity towards cancer related antigens.

The present inventors have discovered that a predominant expression of Th1 (inflammatory) cytokines correlates well with a positive outcome in patients undergoing oncolytic virus therapy; accordingly the extent of Th1 polarization in these patients can be used to predict the outcome of oncolytic virus therapy in patients with cancers such as gliomas. Without being bound by theory, it is proposed that patients having a predominantly Th1 cytokine profile are primed to mount a cell-mediated antitumor immunoresponse to oncolytic viruses. In particular, the present inventors have surprisingly discovered that glioma patients with measurable responses to the oncolytic adenovirus Delta-24-RGD in a positive clinical outcome have high levels of Th1 cytokines IL-12p70, IL-2 and IFN-γ whereas responses of Th2 humoral antibodies predicts that these patients will not respond to the virus. In the Phase I clinical study, patients that had a complete response or a high level of response had high levels of Th1 cytokine interleukin-12p70 pre-operatively (serum levels were highly elevated compared to the rest of the population within the phase I trial) and this level increased after injection of the virus. The three patients who had a complete response to the virus also had serum levels of IL-12p70, which were highly elevated compared to the rest of the population within this phase I trial. The use of Th1 biomarkers for predicting the response of a patient with cancer to oncolytic virus therapy is provided.

One patient in the clinical trial that exhibited low baseline levels of IL-12p70 (i.e. prior to treatment with Delta-24-RGD) was administered IFN-γ two months after the virus was administered. IFN-g stimulated a Th1 immune response in the patient (indicated by an increase in IL-12 production) and corresponded with a very good response to the virus. Thus, methods for treating cancer comprising administration of agents which stimulate or boost the Th1 response and/or suppress regulatory T cells in combination with an oncolytic virus to cancer patients are also provided.

Malignant gliomas constitute the majority of primary cerebral malignant neoplasms. These deadly tumors invariably recur after conventional therapy and the median survival time of patients with glioblastoma (GBM) the most common form of malignant high-grade gliomas is 14 months. In addition to the difficulties to drug delivery imposed by the blood-brain-barrier, conventional chemotherapy and small-molecule approaches have been unable to significantly improve the prognosis of these patients. Oncolytic viruses such as Delta-24-RGD have emerged as a promising alternative to conventional therapies for the treatment of these tumors. However, it is currently not possible to predict whether a patient will respond favorably to such treatment. Although emerging evidence suggests immune response during virotherapy is involved in anti-tumor activity, the role that pre-existing immune conditions play during oncolytic virus treatment and its influence in clinical outcome is currently unknown. The present inventors have discovered that treatment with oncolytic viruses such as Delta-24-RGD induces autophagic cell death leading to endoplasmic reticulum stress with antigen processing and epitope presentation in glioma-infected cells. The present inventors have also surprisingly discovered that patients who are good responders to oncolytic virus therapy exhibit a skew to the T-cell effector response rather than a humoral skewed response. Patients who are good responders to oncolytic virus therapy exhibit a specific Th1 biomarker profile. These biomarkers are of value in the prognosis and treatment of brain and other cancers including determining the optimum group of patients with cancers such as malignant gliomas that are likely to have positive clinical outcomes when treated with oncolytic viruses and thus significantly increase their survival and determining whether a patient is a good candidate for an additional treatment modality. It is expected that the present biomarker profiles are of relevance to the vast majority of solid tumors for which there is currently a dramatic paucity of biomarkers.

Biomarkers that may be measured or detected include, without limitation, proteins (e.g. cytokines, antibodies), cells (e.g. lymphocytes), nucleic acid, and metabolites. Proteins that can be used as biomarkers of the likelihood for response to an oncolytic virus therapy include, but are not limited to cytokines such as lymphokines, monokines, growth factors and traditional polypeptide hormones. Included among the cytokines are growth hormones such as human growth hormone, N-methionyl human growth hormone, and bovine growth hormone; parathyroid hormone; throxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin; fibroblast growth factor; prolactin; placental lactogen; OB protein; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-1 and -II; erythropoietin (EPO); osteoinductive factors; interferons such as interferon-alpha, -beta and -gamma; colony stimulating factors (CSFs) such as macrophage-CSF (M-CSF); granuloctye-macrophage-CSF (GM-CSF); and granulocyte-CSF (G-CSF); interleukins (ILs) such as IL-1, IL-1 alpha, IL-2, 11-3, IL-4, IL-5, IL-6, IL-7, IL-8, IL-9, IL-10, IL-11, IL-12, IL-13, IL-14, IL-15, IL-16, IL-17, 11-18, IL-19, IL-20, IL-24, G-CSF, GM-CSF, EPO, kit-ligand or FLT-3. Other antigens can be measured, for example CMV antigens, EGFRvIII or IL13R. In a further aspect, markers can be measured or detected that are indicative for blood vessel formation in general and for angiogenesis and/or vasculogenesis of tumors in particular fibronectin, fibrinogen and acidic calponin 3 and colligin 2.

Nucleic acids that can be measured or detected include those mRNAs encoding the proteins described above, as well as various non-coding nucleic acid such as miRNAs. A number of nucleic acid arrays are commercially available for mRNA and miRNA.

Antibodies that can be measured or detected as biomarkers of the likelihood for responding to oncolytic virus therapy include, but are not limited to, antibodies against tumor associated antigens such as BRAF (v-raf murine sarcoma viral oncogene homolog B1), CABYR (calcium binding tyrosine-(Y)-phosphorylation regulated), CRISP3 (cysteine-rich secretory protein 3), CSAG2 (CSAG family, member 2), CTAG2 (cancer/testis antigen 2), DHFR (dihydrofolate reductase), FTHL17 (ferritin, heavy polypeptide 1; testis-specific expression), GAGE1 (G antigen 1), LDHC (lactate dehydrogenase C), MAGEA1 (melanoma antigen family A, 1), MAGEA3 (melanoma antigen family A, 3), MAGEA4 (melanoma antigen family A, 4), MAGEB6 (melanoma antigen family B, 6), MAPK1 (mitogen-activated protein kinase 1), MICA (MHC Class I polypeptide-related sequence A), MUC1 (mucin 1, cell surface associated), NLRP4 (NLR family, pyrin domain containing 4), NY-ES-01 (New York oesophageal squamos cell carcinoma 1), P53, PBK (PDZ binding kinase), PRAME (preferentially expressed antigen in melanoma), SOX2 (sex determining region Y-box 2), SPANXA1 (sperm protein associated with the nucleus, X-linked, family member A1), SSX2 (synovial sarcoma, X breakpoint 2), SSX4 (synovial sarcoma, X breakpoint 4), SSX5 (synovial sarcoma, X breakpoint 5), TSGA10 (testis specific, 10), TSSK6 (testis-specific serine kinase 6), TULP2 (tubby like protein), XAGE2 (X antigen family, member 2), and ZNF165 (zinc finger protein 165). It should be understood that antibody biomarkers of the invention are not limited and extend to antibodies against any tumor associated antigen. In a particular aspect, antibodies against cancer/testis antigens are used as biomarkers of the invention. Antibodies against tumor associated antigens that have been identified as occurring in patients with brain cancers such as gliomas are preferable for use as biomarkers of the invention which include but are not limited to: AIM2 (absent in melanoma 2), BMI1 (BMI1 polycomb ring finger oncogene), COX-2 (cyclooxygenase-2), TRP-1 (tyrosine related protein 2) TRP-2 (tyrosine related protein 2), GP100 (glycoprotein 100), EGFRvIII (epidermal growth factor receptor variant III), EZH2 (enhancer of zeste homolog 2), L1CAM (human L1 cell adhesion molecule), Livin, Livinβ, MRP-3 (multidrug resistance protein 3), Nestin, OLIG2 (oligodendrocyte transcription factor), SOX2 (SRY-related HMG-box 2), ART1 (antigen recognized by T cells 1), ART4 (antigen recognized by T cells 4), SART1 (squamous cell carcinoma antigen recognized by T cells 1), SART2, SART3, B-cyclin, b-catenin, Gli1 (glioma-associated oncogene homolog 1), Cav-1 (caveolin-1), cathepsin B, CD74 (cluster of Differentiation 74), E-cadherin (epithelial calcium-dependent adhesion), EphA2/Eck (EPH receptor A2/epithelial kinase), Fra-1/Fosl 1 (fos-related antigen 1), GAGE-1 (G antigen 1), Ganglioside/GD2, GnT-V, β1,6-N (acetylglucosaminyltransferase-V), Her2/neu (human epidermal growth factor receptor 2), Ki67 (nuclear proliferation-associated antigen of antibody Ki67), Ku70/80 (human Ku heterodimer proteins subunits), IL-13Ra2 (interleukin-13 receptor subunit alpha-2), MAGE-A (melanoma-associated antigen 1), MAGE-A3 (melanoma-associated antigen 3), NY-ESO-1 (New York oesophageal squamos cell carcinoma 1), MART-1 (melanoma antigen recognized by T cells), PROX1 (prospero homeobox protein 1), PSCA (prostate stem cell antigen), SOX10 (SRY-related HMG-box 10), SOX11, Survivin, UPAR (urokinase-type plasminogen activator receptor, and WT-1 (Wilms' tumor protein 1).

Thus, in one embodiment, the expression level of antibodies against any combinatino of at least 1, at least 2, at least 3, 4, 5, 6, 7, 8, 9, 10, 11, 12, 13, 14, 15, 16, 17, 18, 19, 20, 25, 30, 35, 40, 45, 50, 55, 60, 65, or at least 70 or more tumor associated antigens selected from the group consisting of: BRAF, CABYR, CRISP3, CSAG2, CTAG2, DHFR, FTHL17, GAGE1, LDHC, MAGEA1, MAGEA3, MAGEA4, MAGEB6, MAPK1, MICA, MUC1, NLRP4, NYES01, P53, PBK, PRAMS, SOX2, SPANXA1, SSX2, SSX4, SSX5, TSGA10, TSSK6, TULP2, XAGE2, ZNF165, AIM2, BMI1, COX-2, TRP-1, TRP-2, GP100, EGFRvIII, EZH2, L1CAM, Livin, Livinβ, MRP-3, Nestin, OLIG2, SOX2, ART1, ART4, SART1, SART2, SART3, B-cyclin, b-catenin, Gli1, Cav-1, cathepsin B, CD74, E-cadherin, EphA2/Eck, Fra-1/Fosl 1, Ganglioside/GD2, GnT-V,β1,6-N, Her2/neu, Ki67, Ku70/80, IL-13Ra2, MART-1, PROX1, PSCA, SOX10, SOX11, Survivin, UPAR, and WT-1 may be measured in a test sample according to the methods described herein.

Thus, in one embodiment, the expression level of antibodies against any combination of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 or at least 46 glioma associated antigens selected from the group consisting of: AIM2, BMI1, COX-2, TRP-1, TRP-2, GP100, EGFRvIII, EZH2, L1CAM, Livin, Livinβ, MRP-3, Nestin, OLIG2, SOX2, ART1, ART4, SART1, SART2, SART3, B-cyclin, b-catenin, Gli1, Cav-1, cathepsin B, CD74, E-cadherin, EphA2/Eck, Fra-1/Fosl 1, GAGE-1, Ganglioside/GD2, GnT-V,β1,6-N, Her2/neu, Ki67, Ku70/80, IL-13Ra2, MAGE-A, MAGE-A3, NY-ESO-1, MART-1, PROX1, PSCA, SOX10, SOX11, Survivin, UPAR, and WT-1 may be measured in a test sample according to the methods described herein.

In other embodiments, the expression level of antibodies against any combination of tumor associated antigens as described herein and the expression level of one or more Th1 biomarkers and optionally the expression level of one or more Th2 biomarkers may be measured in a test sample according to the methods described herein.

Cells that can be measured or detected include CD4 T cells, CD8 T cells, regulatory T cells, microglia and the like.

CD4 T cells express the CD4 protein on their surface. Upon presentation of antigens by major histocompatibility complex (MHC) class II molecules, naïve CD4 T cells mainly differentiate into Th1, Th2 or Th17 (regulatory T cells) cells, each type secreting a different set of cytokines to facilitate a different type of immune response. For example, Th1 cells secrete IL-2, IFN-γ and TNF-β; Th2 cells secrete IL-4, IL-5, IL-6, IL-10 and IL-13; and Th17 cells secrete IL-17α.

CD8 T cells (cytotoxic T cells or CTLs) express the CD8 glycoprotein at their surface and upon presentation of antigen associated with MHC class I molecules, destroy virally infected cells and tumor cells.

Regulatory T cells (also known as suppressor T cells or Th17 cells) are CD4$^+$CD25$^+$FoxP3$^+$ and act to shut down T cell mediated-immunity toward the end of an immune reaction and suppress auto-reactive T cells that escape negative selection in the thymus.

Natural killer T (NKT) cells bridge the adaptive immune system with the innate immune system. Unlike conventional T cells that recognize peptide antigens presented by MHC molecules, NKT cells recognize glyclolipid antigen presented by a molecule called CD1d. Once activated, these cells can produce cytokines and release cytolytic/cell killing molecules. They are also able to recognize and eliminate some tumor cells and cells infected with viruses.

Microglia are glial cells that are the resident macrophages of the brain and spinal cord, and the primary mediator of active immune defense in the central nervous system (CNS). Microglia constitute 20% of the total glial cell population within the brain. Microglia are constantly scavenging the CNS for infective agents. The brain and spinal cord are considered "immune privileged" organs in that they are separated from the rest of the body by a series of endothelial cells known as the blood-brain barrier, which prevents most infections from reaching the vulnerable nervous tissue. In the case where the infectious agents are directed introduced to the brain or cross the blood-brain barrier, microglial cells must react quickly to decrease inflammation and destroy the infectious agents before they damage the sensitive neural tissue. Due to the unavailability of antibodies from the rest of the body (few antibodies are small enough to cross the blood brain barrier), microglia must be able to recognize foreign bodies, swallow them, and act as antigen-presenting cells activating T cells.

Isolation of Samples

Samples (test samples) can be obtained from a patient prior to, concurrently with, or subsequent to treatment with an oncolytic virus from, without limitation, tissue (e.g. tumor biopsy), cerebrospinal fluid, blood, plasma, serum, lymph, and synovial fluid. Standard procedures that are known in the art for obtaining such samples are used. In a preferred embodiment, the sample is a serum sample and the level of one or more biomarkers described herein is determined by enzyme linked immunosorbent assay (ELISA).

Procedures used to biopsy a tumor include, but are not limited to, stereotactic biopsy, which can be done by precise introduction of a metal probe into the brain tumor, cutting a small piece of the brain tumor, and removing it so that it can be examined. For example, the patient is transported to the MRI or CAT scan suite, and a frame is attached to the scalp under local anesthesia. The "pins" of the frame attach to the skull for rigid fixation (frame will not and can not move from that point forward until completion of the biopsy). The scan (MRI or CT) is obtained. The neurosurgeon examines the scan and determines the safest trajectory or path to the target. This means avoiding critical structures. The spatial co-ordinates of the target are determined, and the optimal path is elected. The biopsy is carried out under general anesthesia. A small incision is created over the entry point, and a small hole is drilled through the skull. The "dura" is perforated, and the biopsy probe is introduced slowly to the target. The biopsy specimen is withdrawn and placed in fluids or preservative to assess biomarkers.

Once samples are obtained, the immune status of a subject is determined by measuring or detecting or analyzing various biomarkers to produce data for the determination of the subject's immune status (e.g. the degree of Th1 polarization) in order to determine e.g. the susceptibility of a patient to oncolytic virus therapy, or the need for co-administration of an agent that stimulates a Th1 immune response with the oncolytic virus therapy.

In certain embodiments, the interaction or response of the tumor to the therapy is related to the immunologic status of the tumor or surrounding tissue, the pre-existence of anti-virus antibodies and/or the presence and degree of lymphopenia prior to treatment. It is envisaged that a patient having an immunologic status that suggests immunosuppression may indicate that a tumor will be resistant to oncolytic virus therapy.

Assessment of Biomarkers

Assessment of expression levels of the markers discussed above may be direct, as in the use of immunohistochemistry (IHC) (including semi-quantitative or quantitative IHC) or other antibody-based assays (Western blot, fluorescent immunoassay (FIA), fluorescence in situ hybridization (FISH), radioimmunoassay (RIA), radioimmunoprecipitation (RIP), enzyme-linked immunosorbent assay (ELISA), immunoassay, immunoradiometric assay, fluoroimmunoassay, chemiluminescent assay, bioluminescent assay, gel electrophoresis), or indirectly by quantitating the transcripts for these genes (e.g. by in situ hybridization, nuclease protection, Northern blot, polymerase chain reaction (PCR) including reverse transcriptase PCR (RT-PCR)). Cells, for example, lymphocytes, can be analyzed using FACs technology or paraffin embedded tumor sections using antibodies. Relevant methodologies are discussed below.

Antibodies can be used in the present invention to characterize the protein content of target cells through techniques such as immunohistochemistry, ELISAs and Western blotting. This may provide a screen e.g. for the presence or absence of a subject likely to respond favorably to oncolytic virus therapy and/or a need for co-administering an immune stimulating agent with an oncolytic virus.

Immunohistochemistry is typically performed on a sample of tissue from a biopsy. The sample can be examined fresh or frozen. The tissue sample is sliced extremely thin, so that it is approximately one cell thick, then the sample is fixed onto a glass slide. The cells in the sample have characteristic antigens on their cell surfaces that can be used to help identify the specific type of cell. Antibodies against these characteristic antigens are added to the sample on the slide and the antibodies bind wherever the antigens are present. Excess antibody is then washed away. The antibodies that remain bound to the cell have labels that either fluoresce or undergo a chemical reaction that makes them visible by microscope.

The use of antibodies in an ELISA assay is contemplated if the sample is a tissue lysate, blood, serum or cerebrospinal fluid. For example, antibodies against the antigen to be detected are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of nonspecific adsorption sites on the immobilizing surface and thus reduced the background caused by non-specific binding of antigen to the surface.

After binding of antibody to the well, coating with a non-reactive material to reduce background, and washing to remove unbound material, the immobilizing surface is contacted with the sample to be tested in conditions conducive to immune complex (antigen/antibody) formation.

Following formation of specific immunocomplexes between the test sample and the bound antibody, and subsequent washing, the occurrence and even amount of immunocomplex formation may be determined by subjecting the same to a second antibody having specificity for an antigen that differs from that recognized by the first antibody. Appropriate conditions preferably include diluting the sample with diluents such as BSA, bovine gamma globulin (BGG) and phosphate buffered saline (PBS)/Tween®. These added agents also tend to assist in reduction of nonspecific background. The layered antisera is then allowed to incubate for from about 2 to about 4 hours, at temperatures preferably on the order of about 25° to 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme, or detectable moiety, that can be detected, e.g., will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g. incubation for 2 hours at room temperature in a PBS-containing solution such as PBS/Tween®).

After incubation with a second detectable antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g. using a visible spectrum spectrophotometer.

The preceding format may be altered by first binding the sample to the assay plate, then contacting the sample with a primary antibody, followed by detecting bound primary antibody using a labeled second antibody with specificity for the primary antibody.

Antibodies can also find use in immunoblots or Western blot analysis. The antibodies may be used as high affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluroescently-tagged secondary antibodies against the antigen of interest are considered to be of particular use in this regard.

Aspects of the methods described herein are related to one or more of (i) stimulating a cellular immune response in a subject in combination with administration of an oncolytic virus (e.g. adenovirus), (ii) antagonizing immune suppression in combination with administration of an oncolytic virus (e.g. adenovirus), or (iii) stimulating a cellular immune response in a subject and antagonizing immune suppression in a subject combination with administration of an oncolytic virus (e.g. adenovirus).

A. Antagonism of Immune Suppression

Immunosuppression involves an act that reduces the activation or efficacy of the immune system. Some portions of the immune system itself have immuno-suppressive effects on other parts of the immune system, and immunosuppression may occur as an affect of certain diseases or conditions. Disease related immunosuppression can occur in, for example, malnutrition, aging, many types of cancer (such as glioma, leukemia, lymphoma, multiple myeloma), and certain chronic infections such as acquired immunodeficiency syndrome (AIDS). The unwanted effect in disease related immunosuppression is immunodeficiency that results in increased susceptibility to the growth of hyperproliferative cells.

In certain aspects, the therapeutic methods described herein may reduce immunosuppression in a subject and enhance the oncolytic effect of viral therapies. In certain aspects, the methods may reduce the immunoregulatory T cell activity in the subject. Reducing immunoregulatory T cell activity may be achieved by administering an agent (e.g. an alkylating agent) to the individual that depletes or inactivates immunoregulatory T cells in the individual. Reducing immunoregulatory T cell activity also may be achieved by using at least one antibody that binds to the immunoregulatory T cells. Such antibody may be selected from, but not limited to anti-CD4, anti-CD25, anti-neuropilin, and/or anti-CTLA4 Immunoregulatory T cell activity may be reduced in the individual before, during, or after administering an oncolytic virus. The term "depleting or inactivating in vivo immunoregulatory T cells" as used herein refers to a reduction in the number or functional capability of immunoregulatory T cells that suppress the host anti-tumor immune response. Antagonism of immune suppression can be effected through a reduction of immunoregulatory T cells (i.e., depletion) or inactivation of anti-tumor immune suppression function of the immunoregulatory T cells. The ultimate result of such treatment is to reduce immunoregulatory T cell activity in the recipient of the treatment.

Depleting or inactivating immunoregulatory T cells may be achieved by administering a pharmaceutical agent such as an antibody specific for the CD4 antigen, the alpha chain subunit of the IL-2 receptor (i.e. CD25), and the like and as described herein. Also, an antibody to gamma delta immunoregulatory T cells can be used to deplete such cells and stimulate anti-tumor immunity. Seo et al., J. Immunol. (1999) 163:242-249. Anti-CD40 ligand, also may be used to deplete or inactivate immunoregulatory T cells.

Partial antibody constructs such as CTLA4Ig, a fusion protein of CTLA-4 and Fc of immunoglobulin (Ig) heavy chain, can be used to inhibit the essential co-stimulatory signal for full T cell activation via blocking the interaction between CD28 and B7 molecules. CTLA4Ig may be administered as a pharmaceutical to render regulatory T cells nonresponsive (i.e. inactivation). See Park et al. Pharm Res. (2003) 20(8):1239-48. An IL-2 fusion to *pseudomonas* exotoxin (OnTac) is yet another agent for depleting or inactivating regulatory T cells.

In another approach, agents may be administered that prevent the induction of CD8+ cytolytic T-lymphocyte (CTL) tumor anergy. Agents that agonize CD137, such as agonistic antibodies, may be used to restore the tumor cytolytic function of established anergic CTLs upon reencountering their cognate antigen. See Wilcox et al., Blood (2004) 103:177-184. This approach can be used to break T-cell tolerance to tumor antigens.

Agents that agonize glucocorticoid-induced tumor necrosis factor receptor (GITR) ligand on CD4/CD25+ immunoregulatory T cells reverses the suppressive action of these cells. GITR ligand agonists are described in Tone et al., PNAS (2003) 100:15059-15064; Stephens et al. 2004 and Shimizu et al. 2002.

Antibodies to neurophilin (e.g. Bruder et al. 2004) and antibodies to CTLA-4 (e.g. Leach et al. 1996) also can be administered in vivo to deplete immunoregulatory T cells or reduce their activity.

Methods of removing, depleting or inactivating immunoregulatory T cells may be used even if the methods are not limited solely to such cells. Effort to remove, deplete or inactivate immunoregulatory T cells may be performed multiple times during a given period of treatment. Also, different methods may be used together (e.g., ex vivo cell removal and in vivo depletion or inactivation). The amount of anti-T cell antibody administered for depletion or inactivation may be similar to the amount used in the transplantation field. See, e.g., Meiser et al., Transplantation. (1994) 27; 58(4): 419-23.

Immunoregulatory T cells may be removed, depleted or inactivated before, during and/or after administration of an oncolytic virus. Immunoregulatory T cells are preferably removed, depleted or inactivated before administering the oncolytic virus.

B. Stimulation of the Immune System

The terms "enhance the cellular immune system" and "stimulate the cellular immune system" (and different tenses of these terms) refer to the ability of an agent to stimulate the generation of antigen-specific cytolytic activity (the activity of immune cells, particularly cytotoxic T-lymphocytes) and/or NK cell activity, improve the cellular immune response to antigens (through the activity of at least cytotoxic T-lymphocytes), improve immune protection (by at least restoring the activity of cytotoxic T-lymphocytes and/or NK cells and enhancing cytokine production), restore immune protection (by at least restoring or stimulating the activity of cytotoxic T-lymphocytes and/or NK cell activity and enhancing cytokine production) or generate pro-inflammatory (Th1) cytokines.

Agents which enhance the cellular immune system (or produce a Th1 phenotype) include cytokines (preferably recombinant) representative examples of which are GM-CSF, IL-2, IL-12, IL-18 and interferon-γ. These cytokines can be administered prior to, during, or subsequent to oncolytic virus therapy in order to improve the patient's response to the virus. Recombinant cytokines are commercially obtainable and are administered according to their recommended dosages. Other agents which produce a Th1 phenotype include agents which stimulate the production of IL-12p70 and/or other Th1 cytokines including without limitation lenalidomide (Revlimid) and pomalidomide.

Other agents which produce a Th1 phenotype include alkylating agents representative examples of which are Temozolomide, cyclophosphamide, lomustine (CCNU), bis-chloroethylnitrosourea (BCNU), melphalan hydrochloride, busulfan (butane-1,4-diyl dimethanesulfonate), mechlorethamine (nitrogen mustard), chlorambucil, ifosfamide, streptozocin, dacarbazine (DTIC), thiotepa, altretamine (hexamethylmelamine), cisplatin, carboplatin, and oxalaplatin. The use of these alkylating agents for treating various types of cancer is well established and they may be used at their recommended dosages in order produce a Th1 phenotype.

Other agents which produce a Th1 phenotype include adjuvants, nonlimiting examples of which are monophosphoryl lipid A (MPL®), QS-21 (plant extract comprising soluble triterpene glucoside compounds) or other saponin, oligodeoxynucleotides comprising or consisting of CpG, and ribosomal protein extract (RPE).

Other agents which produce a Th1 phenotype include CD137 agonists such as BMS-663513, CD40 agonists, such as CP-870,893, OX40 (CD134) agonists and CD27 agonists such as CDX-1127.

Other agents which produce a Th1 phenotype include inhibitors of JAK-2, JAK-3, STAT-3, or STAT-5.

Other agents which produce a Th1 phenotype include CTLA-4 antagonists (e.g. Ipilimumab or Tremelimumab), PD-1/PD-L1-receptor antagonists (e.g. MDX-1106, MK-3475, AMP-224, Pidilizumab, or MDX-1105); antibodies that specifically bind to B7-H3 such as MGA271, and indoleamine-2,3-dioxygenase (IDO) inhibitors such as D-1-methyl-tryptophan (Lunate).

In a further embodiment, the methods for treating cancer may include adoptive transfer of immune cells to enhance anti-tumor immunity. As used herein "adoptive transfer" refers to the administration of immune cells, from another individual or from the same individual. These are preferably T cells, which may be activated ex vivo to enhance their ability to function in supporting an anti-tumor immune response. Adoptively transferred immune cells may be activated ex vivo by any of a variety of well known agents including, for example, exposure to IL-2 and/or to anti-CD3 antibodies. Ex vivo activation also may include exposure to a cancer cell vaccine. Such cancer cell vaccine may constitute live (but non-replicating), or killed cancer cells from the individual to be treated or from another cancer entirely. The vaccine also may be a cancer cell extract or purified vaccine preparation derived from cancer cells. Cancer cell vaccines are well known in the art and may be prepared in accordance with well known methods.

III. Antibodies

An antagonist of an immune suppressor or a stimulator of the immune system can be an antibody. The term "antibody" as used herein includes immunoglobulins, which are the product of B cells and variants thereof as well as the T cell receptor (TCR), which is the product of T cells, and variants thereof. An immunoglobulin is a protein comprising one or more polypeptides substantially encoded by the immunoglobulin kappa and lambda, alpha, gamma, delta, epsilon and mu constant region genes, as well as myriad immunoglobulin variable region genes. A typical immunoglobulin structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Recombinant antibodies may be conventional full length antibodies, antibody fragments known from proteolytic digestion, unique antibody fragments such as Fv or single chain Fv (scFv), domain deleted antibodies, and the like. An Fv antibody is about 50 Kd in size and comprises the variable regions of the light and heavy chain. A single chain Fv ("scFv") polypeptide is a covalently linked VH::VL heterodimer which may be expressed from a nucleic acid including VH- and VL-encoding sequences either joined directly or joined by a peptide-encoding linker. See Huston, et al. (1988) Proc. Nat. Acad. Sci. USA, 85:5879-5883. A number of structures for converting the naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091,513; 5,132,405; and 4,956,778.

An antibody may be a non-human antibody, a human antibody, a humanized antibody or a chimeric antibody, the latter comprising human and non-human antibody sequence. As is known in the art, chimeric antibody is prepared by exchanging a non-human constant region (heavy chain, light chain or both) with a human constant region antibody. See e.g. U.S. Pat. No. 4,816,567. Methods of making humanized antibodies from non-human antibodies such as from murine antibodies are also well known (see, e.g., U.S. Pat. No. 5,565,332).

IV. Oncolytic Virus

Oncolytic viruses that can be administered according to the methods of the invention include, without limitation, adenoviruses (e.g. Delta-24, Delta-24-RGD, ICOVIR-5, ICOVIR-7, Onyx-015, ColoAd1, H101, AD5/3-D24-GMCSF), reoviruses, herpes simplex virus (HSV; OncoVEX GMCSF), Newcastle Disease virus, measles viruses, retroviruses (e g influenza viruses), poxviruses (e.g. vaccinia virus including Copenhagen, Western Reserve, Wyeth strains), myxoma viruses, rhabdoviruses (e.g. vesicular stomatitis virus (VSV)), picornaviruses (e.g. Seneca Valley virus; SVV-001), coxsackievirus and parvovirus.

In preferred embodiments, the oncolytic virus is an adenovirus including members of any of the 57 human serotypes thereof (HAdV-1 to 57). In one aspect, the adenovirus is an Ad5 serotype. In other aspects, the adenovirus is hybrid serotype which may or may not comprise an Ad5 component. Non-limiting examples of adenoviruses that may be administered according to the present methods include Delta-24, Delta-24-RGD, ICOVIR-5, ICOVIR-7, ONYX-015, ColoAd1, H101 and AD5/3-D24-GMCSF. Onyx-015 is a hybrid of virus serotype Ad2 and Ad5 with deletions in the E1B-55K and E3B regions to enhance cancer selectivity. H101 is a modified version of Onyx-015. ICOVIR-5 and ICOVIR-7 comprise an Rb-binding site deletion of EIA and a replacement of the EIA promoter by an E2F promoter. ColoAd1 is a chimeric Add11p/Ad3 serotype. AD5/3-D24-GMCSF (CGTG-102) is a serotype 5/3 capsid-modified adenovirus encoding GM-CSF (the Ad5 capsid protein knob is replaced with a knob domain from serotype 3).

In one particularly preferred embodiment, the oncolytic virus is Delta-24 or Delta-24-RGD. Delta-24 is described in U.S. Patent Application Publication Nos. 20030138405, and 20060147420, each of which are incorporated herein by reference. The Delta-24 adenovirus is derived from adenovirus type 5 (Ad-5) and contains a 24-base-pair deletion within the CR2 portion of the E1A gene. Delta-24-RGD further comprises an insertion of the RGD-4C sequence (which binds strongly to $\alpha v\beta 3$ and $\alpha v\beta 5$ integrins) into the H1 loop of the fiber knob protein (Pasqualini R. et al., Nat Biotechnol, 15:542-546 (1997)).

Significant antitumor effects of Delta-24 have been shown in cell culture systems and in malignant glioma xenograft models. Currently delta-24 is showing anti-tumor efficacy in clinical trials. Conditionally replicating adenoviruses (CRADs), such as Delta-24, have several properties that make them candidates for use as biotherapeutic agents. One such property is the ability to replicate in a permissive cell or tissue, which amplifies the original input dose of the oncolytic virus and spreads the virus to adjacent tumor cells providing a direct antitumor effect.

The in vitro and in vivo oncolytic effects of delta-24 adenovirus have been demonstrated. Generally, adenovirus is a 36 kb, linear, double-stranded DNA virus (Grunhaus and Horwitz, 1992). Adenoviral infection of host cells results in adenoviral DNA being maintained episomally, which reduces the potential genotoxicity associated with integrating vectors. Also, adenoviruses are structurally stable, and no genome rearrangement has been detected after extensive amplification. Adenovirus can infect virtually most epithelial cells regardless of their cell cycle stage. So far, adenoviral infection appears to be linked only to mild disease such as acute respiratory disease in humans.

Several factors favor the use of oncolytic adenoviruses for the treatment of brain tumors. First, gliomas are typically localized, and therefore an efficient local approach should be enough to cure the disease. Second, gliomas harbor several populations of cells expressing different genetic abnormalities (Sidransky et al., 1992; Collins and James, 1993; Furnari et al., 1995; Kyritsis et al., 1996). Thus, the spectrum of tumors sensitive to the transfer of a single gene to cancer cells may be limited. Third, replication competent adenoviruses can infect and destroy cancer cells that are arrested in $G_0$. Since gliomas invariably include non-cycling cells, this property is important. Finally, the p16-Rb pathway is abnormal in the majority of gliomas (Hamel et al., 1993; Henson et al., 1994; Hirvonen et al., 1994; Jen et al., 1994; Schmidt et al., 1994; Costello et al., 1996; Fueyo et al., 1996b; Kyritsis et al., 1996; Ueki et al., 1996; Costello et al., 1997), thus making the delta-24 strategy appropriate for most of these tumors. Although the loss of the retinoblastoma tumor suppressor gene function has been associated with the causes of various types of tumors and is not limited to treatment of gliomas.

If an adenovirus has been mutated so that it is unable to replicate or is conditionally replicative (replication-competent under certain conditions), a helper cell may be required for viral replication. When required, helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, for example Vero cells or other monkey embryonic mesenchymal or epithelial cells. In certain aspects a helper cell line is 293. Various methods of culturing host and helper cells may be found in the art, for example Racher et al., 1995.

In certain aspects, the adenovirus is typically replication-competent in cells with a mutant Rb pathway. After transfection, adenoviral plaques are isolated from the agarose-overlaid cells and the viral particles are expanded for analysis. For detailed protocols the skilled artisan is referred to Graham and Prevac, 1991.

Alternative technologies for the generation of adenovirus vectors include utilization of the bacterial artificial chromosome (BAC) system, in vivo bacterial recombination in a recA+bacterial strain utilizing two plasmids containing complementary adenoviral sequences, and the yeast artificial chromosome (YAC) system (PCT publications 95/27071 and 96/33280, which are incorporated herein by reference).

Adenovirus is easy to grow and manipulate and exhibits broad host range in vitro and in vivo. This group of viruses can be obtained in high titers (e.g., $10^9$-$10^{11}$ plaque forming units (pfu) per ml), and they are highly infective. The life cycle of adenovirus does not require integration into the host cell genome.

Modifications of oncolytic adenovirus described herein may be made to improve the ability of the oncolytic adenovirus to treat cancer. Such modifications of an oncolytic adenovirus have been described by Jiang et al. (Curr Gene Ther. 2009 October 9(5):422-427), see also U.S. Patent Application No. 20060147420, each of which are incorporated herein by reference.

The absence or the presence of low levels of the coxsackievirus and adenovirus receptor (CAR) on several tumor types can limit the efficacy of the oncolytic adenovirus. Various peptide motifs may be added to the fiber knob, for instance an RGD motif (RGD sequences mimic the normal ligands of cell surface integrins), Tat motif, polylysine motif, NGR motif, CTT motif, CNGRL motif, CPRECES motif or a strept-tag motif (Rouslahti and Rajotte, 2000). A motif can be inserted into the HI loop of the adenovirus fiber protein. Modifying the capsid allows CAR independent target cell infection. This allows higher replication, more efficient infection, and increased lysis of tumor cells (Suzuki et al., 2001, incorporated herein by reference). Peptide sequences that bind specific human glioma receptors such as EGFR or uPR may also be added. Specific receptors found exclusively or preferentially on the surface of cancer cells may be used as a target for adenoviral binding and infection, such as EGFRvIII.

Oncolytic viruses according to the invention may be administered locally or systemically. For example, without limitation, oncolytic viruses according to the invention can be administered intravascularly (intraarterially or intravenously), intratumorally, intramuscularly, intradermally, intraperitoneally, subcutaneously, orally, parenterally, intranasally, intratracheally, percutaneously, intraspinally, ocularly, or intracranially.

Oncolytic viruses according to the invention may be administered in a single administration or multiple administrations. The virus may be administered at dosage of $1\times10^5$ plaque forming units (PFU), $5\times10^5$ PFU, at least $1\times10^6$ PFU, $5\times10^6$ or about $5\times10^6$ PFU, $1\times10^7$, at least $1\times10^7$ PFU, $1\times10^8$ or about $1\times10^8$ PFU, at least $1\times10^8$ PFU, about or at least $5\times10^8$ PFU, $1\times10^9$ or at least $1\times10^9$ PFU, $5\times10^9$ or at least $5\times10^9$ PFU, $1\times10^{10}$ PFU or at least $1\times10^{10}$ PFU, $5\times10^{10}$ or at least $5\times10^{10}$ PFU, $1\times10^{11}$ or at least $1\times10^{11}$, $1\times10^{12}$ or at least $1\times10^{12}$, $1\times10^{13}$ or at least $1\times10^{13}$. For example, the virus may be administered at a dosage of between about $10^7$-$10^{13}$, between about $10^8$-$10^{13}$, between about $10^9$-$10^{12}$, or between about $10^8$-$10^{12}$.

Oncolytic viruses according to the invention may also be administered in a cellular carrier. In this respect, neuronal and mesenchymal stem cells have high migratory potential yet remain confined to tumor tissue. A subpopulation of adult mesenchymal cells (bone marrow derived tumor infiltrating cells or BM-TICs) has been shown, following injection into gliomas, to infiltrate the entire tumor. Thus, oncolytic viruses according to the invention can be administered in a virus-producing neuronal or mesenchymal stem cell (e.g. BM-TIC) carrier (e.g. by injection of the carrier cell into the tumor).

A. Combination Therapies

Additional therapies may be combined with any of the methods of the invention heretofore described in order to increase the killing of cancer cells, the inhibition of cancer cell growth, the inhibition of angiogenesis or otherwise improve the reverse or reduction of malignant phenotype of tumor cells. These compositions would be provided in a combined amount effective to kill or inhibit proliferation of the cell. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the oncolytic virus and the other includes a second agent therapy.

Alternatively, the treatment may precede or follow the other agent or treatment by intervals ranging from minutes to weeks. In embodiments where the agents are applied separately to the cell, one would generally ensure that a significant period of time did not expire between each delivery, such that the agents would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) to several months (1, 2, 3, 4, 5, 6, 7 or 8) lapse between the respective administrations.

It also is conceivable that more than one administration of either agent will be desired. Various combinations may be employed, e.g. where one or more oncolytic virus treatment is administered before the administration of a second agent; or the second agent may be administered prior to oncolytic virus administration. Successive administration can include one or more administration of the oncolytic virus therapy or second agent. Again, to achieve cell killing, both agents are delivered to a cell in a combined amount effective to kill the cell. For example, the combination of Delta-24 or Delta-24-RGD and immune modulator.

Alternative Cancer Therapies

In accordance with certain embodiments of the present invention, methods for treating cancer are provided that can be used in conjunction with oncolytic virus therapy once a subject is identified as a responder or likely to respond to such therapy (e.g. delta-24-RGD therapy). Such therapies may be utilized when the assays of the present invention indicate that a subject is unlikely to respond to treatment with a replication competent oncolytic virus such as adenovirus (e.g. delta-24-RGD). Alternatively, such therapies may be utilized in combination with replication competent oncolytic virus such as adenovirus in the case that a subject is identified by the present methods as unlikely to respond to treatment with only replication competent oncolytic virus.

Surgery

Approximately 60% of persons with cancer will undergo surgery of some type, which includes preventative, diagnostic, staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

In certain aspects, a therapy is administered by intratumoral injection prior to surgery or upon excision of a part of or all of cancerous cells, tissue or tumor. Treatment may also be accomplished by perfusion, direct injection or local application of these areas with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages.

Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall within the following categories: alkylating agents, antimetabolites, antitumor antibiotics, topoisomerase inhibitors, and mitotic inhibitors.

Alkylating agents direct interact with genomic DNA to prevent the cancer cell from proliferating. This category of drugs include agents that affect all phases of the cell cycle and are commonly used to treat chronic leukemia, non-Hodgkin's lymphoma, Hodgkin's disease, malignant melanoma, multiple myeloma, and particular cancers of the breast, lung, and ovary. They include nitrogen mustards such as mechlorethamine (nitrogen mustard), chlorambucil, cyclophosphamide (Cytoxan®), ifosfamide and melphalan, nitrosoureas such as streptozocin, carmustine (BCNU) and lomustine, alkyl sulfonates such as busulfan, triazines such as dacarbzine (DTIC) and temozolomide (Temodar®), ethylenimines such as thiotepa and altretamine (hexamethylmelamine), and platinum drugs such as cisplatin, carboplatin, and oxalaplatin.

Antimetabolites disrupt DNA and RNA synthesis. Unlike alkylating agents, they specifically influence the cell cycle during S phase. They have been used to combat chronic leukemias, and tumors of the breast, ovary and gastrointestinal tract. Antimetabolites include 5-fluorouracil (5-FU), 6-mercaptopurine (6-MP), capecitabine (Xeloda®), cladribine, clofarabine, cytarabine (Ara-C®), floxuridine, fludarabine, gemcitabine (Gemzar®), hydroxyurea, methotrexate, pemetrexed, pentostatin and thioguanine.

Antitumor antibiotics have both antimicrobial and cytotoxic activity. These drugs also interfere with DNA by chemically inhibiting enzymes and mitosis or altering cellular membranes. These agents work in all phases of the cell cycle and are used to treat a variety of cancers. Representative examples include daunorubicin, doxorubicin (Adriamycin®), epirubicin, idarubicin, actinomycin-D, bleomycin and mitomycin-C. Generally, these compounds are administered by bolus i.v. injections at doses ranging from 25-100 mg/kg Topoisomerase inhibitors interfere with topoisomerases, enzymes which help separate DNA strands so they can be copied and are used to treat certain leukemias, as well as lung, ovarian, gastrointestinal and other cancers and include topotecan, irinotecan, etoposide (VP-16) and teniposide.

Mitotic inhibitors, often plant alkaloids, work during M phase of the cell cycle and prevent mitosis or inhibit enzymes from producing proteins required for cell reproduction. Representative examples include taxanes such as paclitaxel (Taxol®) and docetaxel (Taxotere®), epothilones such as ixabepilone (Ixempra®), vinca alkaloids such as vinblastine (Velban®), vincristine (Onocovin®) and vinorelbine (Navelbine®), and Estramustine (Emcyt®).

Other chemotherapeutic agents include targeted therapies such as imatinib (Gleevec®), gefitinib (Iressa®), sunitinib (Sutent®), sorafenib (Nexavar®), bortezomib (Velcade®), bevacizumab (Avastin®), trastuzumab (Herceptin®), cetuximab (Erbitux®), and panitumumab (Vectibix®), hormone therapies including antiestrogens such as fulvestrant (Faslodex), tamoxifen, toremifine, aromatase inhibitors such as anastrozole, exemstane and letrozole, progestins such as megestrol acetate, and gonadotropin-releasing hormone and immunotherapies such as antibodies against tumor specific antigens (e.g. prostate specific antigen, carcinoembryonic antigen, urinary tumor associated antigen, fetal antigen, tyrosinase (p97), gp68, TAG-72, HMFG, Sialyl Lewis Antigen, MucA, MucB, PLAP, estrogen receptor, laminin reeptor, erb B and p155) which may be conjugated to a drug or toxin (e.g. radionuclide, ricin A chain, cholera toxin, pertussis toxin).

Radiotherapy

Radiotherapy, also called radiation therapy, is the treatment of cancer and other diseases with ionizing radiation which may be used to treat localized solid tumors such as cancers of the skin, tongue, larynx, brain, breast or cervix, or may be used to treat cancers of the blood-forming cells (leukemia) and lymphatic system (lymphoma). Radiation therapy includes, without limitation, the use of y-rays, X-rays and/or the directed delivery of radioisotopes to tumor cells. Other forms of DNA damaging factors are contemplated such as microwaves and UV-irradiation. Dosage ranges for X-rays range from daily doses of 50-200 roentgens for prolonged periods of time (3 to 4 weeks), to single doses of 2000-6000 roentgens.

Radiotherapy also comprises the use of radiolabeled antibodies to deliver doses of radiation directly to the cancer site (e.g. radioimmunotherapy, conformal radiotherapy), high resolution intensity modulated radiotherapy, and stereotactic radio-surgery. Stereotactic radio-surgery (gamma knife) for brain and other tumors employs precisely targeted beams of gamma radiotherapy from hundreds of different angles. Only one session, taking about 4-5 hours is required.

V. Pharmaceutical Compositions

Cells, viruses, polypeptides, peptides, and compounds (i.e, therapeutic agents) described herein can be administered as a pharmaceutical or medicament formulated with a pharmaceutically acceptable carrier. Accordingly, the therapeutic agents may be used in the manufacture of a medicament or pharmaceutical composition. Pharmaceutical compositions of the invention may be formulated as solutions or lyophilized powders for parenteral administration. Powders may be reconstituted by addition of a suitable diluent or other pharmaceutically acceptable carrier prior to use. Liquid formulations may be buffered, isotonic, aqueous solutions. Powders also may be sprayed in dry form. Examples of suitable diluents are normal isotonic saline solution, standard 5% dextrose in water, or buffered sodium or ammonium acetate solution. Such formulations are especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride, sodium citrate, and the like.

Alternately, therapeutic agents may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation may be in the form of a syrup, elixir, emulsion, or an aqueous or non-aqueous suspension. For rectal administration, the invention compounds may be combined with excipients such as cocoa butter, glycerin, gelatin, or polyethylene glycols and molded into a suppository.

Therapeutic agents may be formulated to include other medically useful drugs or biological agents. The therapeutic agents also may be administered in conjunction with the administration of other drugs or biological agents useful for the disease or condition to which the invention compounds are directed.

As employed herein, the phrase "an effective amount," refers to a dose sufficient to provide concentrations high enough to impart a beneficial effect on the recipient thereof. The specific therapeutically effective dose level for any particular subject will depend upon a variety of factors including the disorder being treated, the severity of the disorder, the activity of the specific compound, the route of administration, the rate of clearance of the compound, the duration of treatment, the drugs used in combination or coincident with the compound, the age, body weight, sex, diet, and general health of the subject, and like factors well known in the medical arts and sciences. Various general considerations taken into account in determining the "therapeutically effective amount" are known to those of skill in the art and are described, e.g., in Gilman et al., eds, Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990. Dosage levels typically fall in the range of about 0.001 up to 100 mg/kg/day; with levels in the range of about 0.05 up to 10 mg/kg/day are generally applicable. A compound can be administered parenterally, such as intravascularly, intravenously, intraarterially, intramuscularly, subcutaneously, or the like. Administration can also be orally, nasally, rectally, transdermally or inhalationally via an aerosol. The compound may be administered as a bolus, or slowly infused.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention and thus can be considered to constitute preferred modes for its practice. However, those of skill in the art should, in light of the disclosure, appreciate that many changes can be made in the specific embodiments which are disclosed and still obtain a like or similar result without departing from the spirit and scope of the invention.

Example 1

Phase I Clinical Study

A Phase I, dose-escalation, two-arm clinical trial of conditionally replication-competent adenovirus (Delta-24-RGD) for treatment of malignant gliomas has recently been completed. Arm A of the study tested direct intratumoral injection of a single dose of Delta-24-RGD into a growing area of a recurrent glioma. Arm B tested intratumoral administration of a divided dose into the resection bed following removal of a recurrent glioma. The A arm study started at a dose of $1 \times 10^7$ viral particles (vp) and escalated in half log increments through $3 \times 10^{10}$ vp; no maximum tolerated dose (MTD) was reached because no dose-limiting toxicities were found, nor were any serious adverse events (SAEs) reported. The Phase I trial showed clear evidence of tumor response and good survival in both A and B arms after reaching the relatively low dose of $3 \times 10^8$ vp. The Phase I A arm data (n=24) shows a high response rate by MRI (30-40%), as evidenced by tumor shrinkage and characteristic changes ("signature changes") on MRI. The evidence that these signature changes are relevant is derived from pathology reports on surgically resected tumors. Two tumors were resected several months after Delta-24-RGD therapy in response to what appeared to be tumor progression. In both instances, pathologists reported that the tumors were 80% and 90% dead (necrotic) with the remaining tumor infiltrated by predominantly CD8 T cells. As a practical matter, the signature changes on MRI elicited by intratumoral delivery of Delta-24-RGD can be used as an early indicator of clinical response without having to rely upon accurate measurements of tumor size.

Delta-24-RGD is an adenovirus that has been engineered to infect cells lacking the Rb tumor suppressor gene, a condition unique to tumor cells, with high selectivity. In theory, adenovirus propagation in the tumor mass results in a series of infection-replication-lysis-infection events that will generate a wave of propagation, to potentially eradicate the tumor mass. Oncolytic viruses such as adenoviruses, therefore, hold a unique promise of overcoming the resistance of gliomas to convention therapies and circumvent the inaccessibility of tumor for surgery and the trend of resistance of cancer cells to radiotherapy and chemotherapy. A goal of the Phase I study was to find the maximum tolerable dose of Delta-24-RGD administered by intratumoral injection and into the post-resection cavity in patients with recurrent malignant glioma. Results from this trial revealed that the intratumoral injection of the virus instigated an initial phase of oncolysis followed by a delayed inflammatory (Th1 polarized) response that ultimately resulted in tumor shrinkage with complete regression in a subset of these patients. This is the first evidence that patients with gliomas develop an immune response after exposure to oncolytic virus such as Delta-24-RGD and that this immune response can be used as the basis for predicting success of the treatment.

Although the results described herein were obtained in patients with high-grade gliomas, the ability of oncolytic viruses in general (and Delta-24-RGD virus in particular) to replicate in multiple tumor types has been demonstrated, including without limitation breast carcinoma, prostate carcinoma, large cell lung carcinoma and sarcomas. The data presented herein on the treatment of gliomas is expected to be relevant to the vast majority of other solid tumors.

A finding that was completely unexpected and unique during the phase I clinical trial using Delta-24-RGD was that at least 2 patients who had been previously treated with (and failed) Temozolomide and radiation therapy had a minimum of what appeared to be complete radiographic responses based on serial magnetic resonance imaging (MRI) scans. These patients had classic tumor response by MRI; one showed dramatic changes on MRI without shrinking and upon subsequent resection, the tumor was reported by pathology to be 90% necrotic with the rest infiltrated with immune cells. One of these patients is still alive and well over 2½ years after treatment with a single injection of the virus. This was a striking finding and what was more unexpected was that the 2 patients who had these complete responses also had serum levels of IL-12p70, which were highly elevated compared to the rest of the population within this phase I trial. These IL-12p70 levels of cytokine correlate very well with the hypothesis that a T-helper-one (Th-1) polarization is necessary for optimal action of the oncolytic adenovirus. In fact, all patients who responded to treatment with Delta-24-RGD had significantly elevated IL-12p70 levels prior to and after treatment with the virus (100% correlation). This data is also consistent with the finding, discussed below, that the serum of these patients with complete responses had very low levels of antibodies against cancer-related antigens. Moreover, analysis of resected tumors from patients that responded to the virus during the Phase 1 study demonstrated an infiltration of macrophages at two weeks post-treatment followed by CD8 T cells at several months.

This data suggests that stimulation of a Th1 phenotype (i.e. high levels of Th1 cytokines such as IL-12) in a patient, for example by administering a Th1 cytokine such as human recombinant IL-12p70, IL-2, IFN-γ or an agent which stimulates IL-12p70 production such as Revlimid or lenalidomide prior to or after administration of an oncolytic virus such as Delta-24-RGD could potentially be used to augment the patient's response to the effects of the virus. Thus, one patient with low baseline IL-12p70 levels was administered IFN-γ 2 months after receiving Delta-24-RGD (2 million units of interferon gamma-1b (Actimmune®) subcutaneously on Monday, Wednesday and Friday, continuously) in order to produce a Th1 phenotype and accordingly augment the anti-tumor effects of the virus. The patient responded very well to the virus and appears to be a complete responder, thus providing a proof of principle. Suppression of Th2 cytokines such as IL-4, IL-5, IL-10, IL-13 could also represent a novel strategy for augmenting the effects of oncolytic viruses.

The present inventors have also discovered that patients who had a high level of antibodies against cancer related antigens prior to receiving Delta-24-RGD or who developed an increase in circulating auto-antibodies to cancer antigens during oncolytic virus therapy did not exhibit a response to the virus. Conversely, the serum of patients who were complete responders had very low levels of antibodies against cancer related antigens. A 100% correlation was again observed, consistent with the correlation between IL-12p70 and response to the virus. Thus, a T-helper-one (Th-1) polarization is necessary for optimal action of the oncolytic adenovirus. Briefly, sera of patients entering the Phase I clinical trial were tested for the presence or absence of antibodies against 31 distinct cancer related antigens both prior to receiving Delta-24-RGD and also for the development of antibodies post-treatment. These cancer antigens included cancer/testis antigens, a class of tumor antigens whose expression is normally restricted to germ lines but are activated in a wide range of cancer types, often encoding antigens that are immunogenic in cancer patients. Currently there are no systemic studies on the presence of these antibodies against cancer antigens in patients with glioma. The present inventors have obtained the first evidence that patients with glioma have developed an immune response against cancer antigens. Surprisingly, serum from patients with tumors that had a radiographic response to Delta-24-RGD had low or no humoral antibody response to the defined set of antigens. The lack of antibody response in patients who respond to Delta-24-RGD is consistent with the requirement of a Th1 polarized immune system to respond to the virus.

These unique findings have extremely broad implications: (1) high levels of Th1 cytokines such as IL-12p70 and/or low levels of antibodies to cancer related antigens provides a novel set of biomarkers which can be used to identify a subset of patients who will respond to oncolytic virus (e.g. adenovirus) therapy and (2) administration of agents which produce a Th1 immune phenotype (i.e. increase the levels of IL-12p70 and other Th1 cytokines) can be co-administered prior to or after administration of an oncolytic virus in order to augment oncolytic virus therapy. For instance, recombinant human IL-12p70 (or interferon-gamma or an agent which stimulates production of these cytokines such as Revlimid) could be administered to cancer patients systematically to augment the effect of oncolytic viruses such as adenovirus and thereby increase antitumor activity and improve treatment outcome.

The present inventors have thus discovered that a predominant expression of Th1 cytokines can be used to predict the outcome of oncolytic virus therapy in patients with cancers such as gliomas. Without wishing to be bound by theory, it is proposed that a subset of patients with cancer having a predominantly Th1 cytokine profile are primed to mount a cell-mediated antitumor immunoresponse. In particular, the present inventors have surprisingly discovered that glioma patients with measurable responses to Delta-24-RGD in a positive clinical outcome have high levels of Th1 cytokines IL-12p70, IL-2 and IFN-γ whereas a high level of antibodies against tumor associated antigens seems to predict patients who will not respond to the virus. The patients that had a complete response or a high level of response had high levels of Th1 cytokine interleukin-12p70 pre-operatively (serum levels were highly elevated compared to the rest of the population within the phase I trial) and this level increased after injection of the virus. The two patients who had complete responses also had serum levels of IL-12p70, which were highly elevated compared to the rest of the population within this phase I trial.

The role of other proinflammatory Th1 cytokines (e.g. IFN-γ) and anti-inflammatory Th2 cytokines (e.g. IL-4 and IL-10) in the response of glioma patients to treatment with the oncolytic adenovirus Delta-24-RGD was investigated. The role of phosphoproteins (phospho-STAT3 (Tyr 705)) and cleaved caspase-3 were also examined. Phospho-STAT3 (Tyr705). Thus, phospho-STAT3 (Tyr705) and cleaved caspase-3 in cell lysates and GM-CSF, IFNγ, IL1β, IL-2, IL-6, IL-8, IL-10, IL-12p40 and TNFα levels in cell culture media were determined using custom-coated multispot plates and a Sector Imager 6000 according to the manufacturer's protocol (Meso Scale with minor modifications). For quantitation of cytokines, cell culture media were collected and stored at −80° C. For cleaved caspase-3 and phospho-STAT3 (Tyr 705) quantitation, cells subjected to experimental manipulations were washed with ice-cold phosphate-buffered saline and then lysed by placing on ice in MSD complete lysis buffer (150 mM NaCl, 20 mM Tris [pH 7.5], 1 mM EDTA, 1 mM EGTA, 1% Triton X-100, 10 mM NaF, MSD phosphatase inhibitor I, MSD phosphatase inhibitor II, and Protease Inhibitor Cocktail) with occasional vortex-mixing for 30 min. Following centrifugation at 17,968 g for 10 min at 4° C. the supernatant was collected, and the protein concentration was determined and the cleared lysates were stored at −80° C.

Electrochemiluminescence assays were performed on biological duplicate samples using capture antibody pre-coated 96-well multispot plates from Meso Scale Discovery (MSD; Gaithersburg, Md.). Briefly, plates were blocked for 1 hour at room temperature with shaking and washed four times with Tris-buffered saline with 0.1% Tween-20. Fifteen micrograms of protein or twenty-five microliters of supernatant or calibrator was added to each well and incubated with shaking for 1 hour at room temperature or overnight at 4° C. Plates were washed and then specific protein levels were quantitated by adding 25 µl of 1 µg/ml specific detection antibody labeled with MSD SULFO-TAG reagent to each well and incubated with shaking for 2 hours at room temperature. Plates were washed four times with Tris-buffered saline with 0.1% Tween-20 as before, 150 µl of 2× or 1× read buffer was added, and the plates were immediately read using the SECTOR Imager 6000, and data were quantitated using Discovery Workbench and SOFTmax PRO 4.0.

Data obtained to date has demonstrated that a predominant expression of Th1 cytokines predicts a patient's clinical outcome. Without being bound by theory, it is proposed that a subset of patients with cancer having a predominantly Th1 cytokine profile are primed to mount a cell-mediated antitumor immunoresponse. In particular, the present study demonstrates a Th1-driven immune response by cytokines IL-12 and IFN-γ in glioma patients correlates with a measurable response to Delta-24-RGD and positive clinical outcome, whereas a high level of antibodies against tumor associated antigens seems to predict patients who will not respond to the virus. The response of Th2 cytokines IL-4 and IL-10 are not involved during Delta-24-RGD treatment and their expression levels do not appear to be relevant for clinical outcome. Thus, a skew of the immune response from humoral (as measured by e.g. autoantibody titration) to cellular (as documented e.g. by cytokine analyses) can be used to predict patients that are likely to be responders to oncolytic viruses such as Delta-24-RGD.

An alternative or additional strategy for augmenting the effects of oncolytic viruses such as Delta-24-RGD is to decrease the level of or suppress the T-regulatory cells also known as T-regs which can be accomplished by a number of chemotherapy agents, including a number of alkylating agents such as Temozolomide and cyclophosphamide. The highly Th1 polarized immune systems prior to and during therapy in the two complete responders who had previously failed temozolomide therapy indicates that an agent that suppresses T-regulatory cells could be administered to a glioma or other cancer patient prior to oncolytic virus therapy in order to prime the patient's immune system to respond to the virus. Alternatively, an agent that suppresses T-regulatory cells could be administered after administration of the virus.

Taking advantage of the discoveries described herein, a "perfect storm" treatment is envisioned or embodied by the use of an oncolytic virus such as Delta-24-RGD comprising (a) pre-administration of an IL-12 stimulating agent such as recombinant human IL-12p70 or IFN-γ or agents such as Revlimid (lenalinamide) to stimulate IL-12p70 production prior to administering the virus (b) injection of the virus into multiple areas of the tumor to achieve maximal oncolysis and optionally (c) administering to the patient an agent which can reduce the T-reg population in the proliferate case and/or stimulate a cell mediated immune response. For example, Temozolomide can be used to reduce T-reg populations in a potentially a dose-dense fashion which would be 7 days on and 7 days off or 21 days on and 7 days off or standard dosing, five days on, 23 days off of the drug. This combination therapy would first increase Th1 cytokines, which drive the Th1 or T-helper 1 response, which mediates T-cell effector cells. The introduction of Delta-24-RGD into the tumor mass then creates an "antigen burst" of both viral antigens and presumably cancer-related antigens, as the tumor cells are lysed. Finally, administration of agents that stimulate a cell mediated immune response against tumor related antigens such as CTLA-4 antagonists such as Ipilimumab and PD-1/PD-L1 receptor antagonists stimulate and keep the T-cells mediated clones replicating and active.

Example 2

Phase IB Clincial Trial: Co-Administration of an Oncolytic Virus with a Th1-Stimulating Agent A phase 1B clinical study is underway designed to determine the maximum tolerated dose of Delta-24-RGD, administered by intratumoral injection and into the post-resection cavity concurrent with Ipilimumab, administered intravenously, as well as the dose limiting toxicities and anti-tumor activity of the combination.

Ipilimumab is a fully human cytotoxic T-lymphocyte antigen (CTLA-4)-blocking IgG1k monoclonal antibody (formerly MDX-010). CTLA-4 is a negative regulator of T cell activation. CTLA-4 functions as an immune checkpoint by exerting an inhibitory control on T cell activation and blocking this particular pathway. Blockade with ipilimumab allows the immune response to persist. Ipilimumab binds to CTLA-4 and blocks interaction of CTLA-4 with its ligands CD80/CD86. CTLA-4 blockade has been shown to augment T-cell activation and proliferation; the mechanism of action of ipilimumab may occur through T-cell mediated anti tumor immune responses. Briefly, ipilimumab blocks the regulatory feedback loop mediated by CTLA-4 and thereby effectively stimulates T-cell proliferation and secretion of IL-2. Ipilimumab has gained regulatory approval by the FDA for treatment of unresectable or metastatic melanoma. During a Phase 3 clinical trial in which patients with these cancers were administered either gp100 (a peptide vaccine comprising a melanoma-associated antigen), ipilimumab or a combination of both. Patients treated with ipilimumab alone had a 34% reduction in risk of death over the gp100 arm but no difference in median overall survival (OS) was observed between ipilimumab alone and the combination of gp100+ ipilimumab.

Patient Eligibility—Inclusions

Patients with histologically proven recurrent malignant primary glioma will be eligible. Glioma type will be restricted to: gliobastoma multiforme (GBM) and gliosarcoma (GS). Patients will consent to have a biopsy taken at the time of the stereotactic injection to confirm the presence of malignant glioma (based on frozen section) before injection of Delta-24-RGD-4C. Patients must be willing and able to give informed consent. Patient age must be ≥18 years. Patients must have a Karnofsky performance status >/=60. Patients must have recovered from the toxic effects of prior therapy (i.e. CTC grade 1 or less)—for example, they must be at least 2 weeks after vincristine, 6 weeks after nitrosoureas, and 3 weeks after procarbazine or Temozolomide administration. Patients must have adequate bone marrow function (absolute granulocyte count ≥1,500 and platelet count of ≥75,000), adequate liver function (SGPT and alkaline phosphatase ≤2 times institutional normals and bilirubin <1.5 mg %), and adequate renal function (BUN or creatinine <1.5 times institutional normal) prior to starting therapy. This study was designed to include women and minorities, but was not designed to measure differences of intervention effects. Males and females will be recruited with no preference to gender. No exclusion to this study will be based on race. Minorities will actively be recruited to participate.

Exclusions

Excluded from the study will be patients with: (1) Active uncontrolled infection or unstable or severe intercurrent medical conditions. All patients must be afebrile at baseline (i.e., <38.0° Celsius [C.]). (2) Evidence of bleeding diathesis or use of anticoagulant medication or any medication that may increase the risk of bleeding that cannot be stopped prior to surgery. If the medication can be discontinued ≥1 weeks prior to Delta-24-RGD-4C injection then patient may be eligible. (3) History or current diagnosis of any medical or psychological condition that in the Investigator's opinion, might interfere with the subject's ability to participate or inability to obtain informed consent because of psychiatric or complicating medical problems. (4) Female who is pregnant and/or nursing. Because of the potential risk of a recombinant virus containing a gene involved in cellular growth regulation and differentiation which could potentially affect a developing fetus or growing infant, females who are pregnant, at risk of pregnancy, or breast feeding a baby during the study period are excluded. (5) Immunocompromised subjects, subjects with autoimmune conditions, active hepatitis (A, B, C or D [Delta]) or HIV seropositivity. (6) Patients with Li-Fraumini Syndrome or with a known germ line deficit in the retinoblastoma gene or its related pathways. (7) Multiple intracranial malignant glioma lesions. (7) Documented extracranial metastasis. (8) Biologic/immunotherapy (e.g., IL-2, IL-12, interferon) within 2 weeks of Delta-24-RGD-4C administration. (9) Any contraindication for undergoing MRI such as: individuals with pacemakers, epicardial pacer wires, infusion pumps, surgical and/or aneurysm clips, shrapnel, metal prosthesis, implants with potential magnetic properties, metallic bodies in the eyes, etc. (10) White blood cell (WBC) $<2.5 \times 10^3/$mm$^3$, absolute neutrophil count (ANC) $<1.5 \times 10^3/$mm$^3$, platelet $<75,000/$mm$^3$, hemoglobin (Hgb) $\leq 10.0$ gm/dL, prothrombin time/international normalized ratio (PT/INR) or partial thromboplastin time (PTT) $>1.8 \times$ control. (11) Grade 4 hematological toxicity. (12) Serum creatinine $>1.5$ mg/dL. (13) Liver transaminases (aspartate aminotransferase [AST] and/or alanine aminotransferase [ALT]) or total bilirubin $>2 \times$ the upper limits of normal. (14) Current diagnosis of other cancer except curative cervical cancer in situ, basal or squamous cell carcinoma of the skin. (15) History of encephalitis, multiple sclerosis, other CNS infection or primary CNS disease that would interfere with subject evaluation. (16) Males or females who refuse to use a double-barrier form of birth control during the study and for up to 6 months after injection with Delta-24-RGD-4C Treatment Plan—Study Overview This study will have a limited phase IB component with the combination of ipilimumab with Delta-24-RGD-4C for the treatment of patients with recurrent glioblastoma. Study patients will require biopsy-confirmed recurrent tumor and will allow two prior therapies or two prior tumor recurrences.

Patients with biopsy-confirmed first or section recurrence of GBM will be consented and administered an initial intratumoral or resection bed injection of $3 \times 10^{10}$ vp Delta-24-RGD in 1 ml. Patients will be monitored for viral shedding at a variety of time points and for tumor response by MRI at two and four weeks to look for "signature" evidence of tumor destruction on MRI. Patients who show no evidence of changes on MRI will be offered an additional dose of Delta-24-RGD, followed by the option of a third dose at two months post treatment. This strategy will control for the possibility that Delta-24-RGD may be delivered sub-optimally during a single injection. Sub-optimal delivery could be due to: (1) missing or not selecting an enhancing area of the tumor, (2) reflux of virus out of the tumor due to intratumoral pressure, (3) genetic alterations in the tumor that make it unable to support robust Delta-24-RGD replication, or (4) immune suppression due to prior toxic chemotherapy or corticosteroids that may affect the ability of Delta-24-RGD to establish an antitumor response.

All patients will be monitored for tumor response, safety, progression-free and overall survival and quality of life assessments. Besides all of the standard blood measurements, including Ad seroconversion, we will also catalog the appearance (or disappearance) of serum anti-tumor antibodies using a proprietary assay developed by Serametrix (Carlsbad, Calif.), as well as cytokine assays.

Dose Escalation—Phase I

The dosing of Delta-24-RGD-4C, will be given at one log less than the highest dose which was safely given during the previous phase I study of Delta-24-RGD-4C as a single agent, that being a dose of $3 \times 10^9$ viral particles per ml given as a one ml injection into the tumor bed by a stereotactic framed delivery system. (The highest dose given during the previous phase I single-agent study was $3 \times 10^{10}$ viral particles per ml). The phase I component will be based on a 3×3 design, whereas if no toxicity is seen in the first 3 patients greater than grade 1 or 2, then the patients may escalate to the next dose which will be $1 \times 10^{10}$ viral particles per ml given in 1 ml injection volume, again by stereotactic framed delivery method. Again, if there is no toxicity greater than 1 or 2 at this dose level then we will reach the maximum dose for this trial which will be $3 \times 10^{10}$ viral particles per ml given on day 28 after starting the temozolomide dosing. The patients will be allowed to have up to 3 total injections of the virus on subsequent monthly courses 2 and 3, again given at day 21 after starting a new course of temozolomide. Once the highest dose combination is reached, assuming there is no toxicity greater than grade 1 or 2, then the phase II component of this combination clinical trial will commence.

All Subjects

After virus administration and surgical procedures, all subjects will be transferred to the ICU until stable. Subjects may then be transferred to an in-patient or Step-Down unit based on the primary surgeon's decision. After 3 days, final discharge of subjects will be at the discretion of the Investigator. Subjects will be placed on contact isolation for the duration of their post-operative hospitalization and managed per institutional policies for adenovirus infection.

Dosing and Dose-Escalation

Safety Stopping Rules—The primary safety variable will be the proportion of subjects who experience any grade 3 or greater toxicity that are at least possibly related to Delta-24-RGD-4C (and not to the surgical procedure).

The toxicity rate will be no greater than 30% for any dose level. If the number of subjects who experience grade 3 or greater toxicity that are deemed to be at least possibly related to Delta-24-RGD-4C is greater than or equal to the subject probabilities above who received Delta-24-RGD-4C, then the dose will be considered too toxic and the subjects exhibiting DLT attributable to Delta-24-RGD-4C will be reviewed by Principal Investigator.

Additional study-stopping criteria include (a) death that is at least possibly attributable to Delta-24-RGD-4C, (b) severe allergic reactions at least possibly attributed to Delta-24-RGD-4C (CTC Grade 3 or 4), and/or (c) DLT in $\geq$two patients at the lowest dose level.

Dose Interruption—Delta-24-RGD-4C administration should be interrupted if the subject develops symptoms of decreased cerebral function or cardiovascular perfusion or if there are signs of allergic reaction or anaphylaxis. Signs or symptoms of anaphylaxis include rash, hives, changes in blood pressure, and shortness of breath in subjects not under general anesthesia. Delta-24-RGD-4C administration will also be interrupted for any adverse event that, in the Investigator's opinion, warrants interruption. In addition, if it appears at that ventricular penetration has occurred, the procedure will be aborted and no further Delta-24-RGD-4C will be administered.

Corticosteroids and Anticonvulsants—Decadron will be used in the study because the greatest challenge in viral gene therapy has been the immune response to the virus itself. Steroids will also control brain inflammation and edema. The total daily steroid dose (expressed in mg decadron/day) will be recorded the day before surgery. The dose will be adjusted at the discretion of the Investigator, with the exception that all subjects will receive 10 mg IV just prior to surgery. "Surgery" includes both stereotactic injection and open craniotomy. Efforts will be made to reduce the steroid dose to the minimal clinically efficacious dose. Anticonvulsants will be administered at the discretion of the Investigator.

Excluded Therapy—Subjects may not receive any of the following medications or therapies while on-study following a Delta-24-RGD-4C injection: (1) Vaccinations (2) Gene transfer therapy Dose Modification for Ipilimumab—Recommended Dose Modifications per Prescribing information. Withhold dose for any moderate immune-mediated adverse reactions or for symptomatic endocrinopathy until return to baseline, improvement to mild severity, or complete resolution, and patient is receiving <7.5 mg prednisone or equivalent per day. Permanently discontinue YERVOY for any of the following (1) Persistent moderate adverse reactions or inability to reduce corticosteroid dose to 7.5 mg prednisone or equivalent per day (2) Failure to complete full treatment course within 16 weeks from administration of first dose (3) Severe or life-threatening adverse reactions, including any of the following: (i) Colitis with abdominal pain, fever, ileus, or peritoneal signs; increase in stool frequency (≥7 over baseline), stool incontinence, need for intravenous hydration for >24 hours, gastrointestinal hemorrhage, and gastrointestinal perforation (ii) AST or ALT>5×the upper limit of normal (ULN) or total bilirubin>3×the ULN (iii) Stevens-Johnson syndrome, toxic epidermal necrolysis, or rash complicated by full-thickness dermal ulceration or necrotic, bullous, or hemorrhagic manifestations (iv) Severe motor or sensory neuropathy, Guillain-Barré syndrome, or myasthenia gravis (v) Severe immune-mediated reactions involving any organ system (vi) Immune-mediated ocular disease unresponsive to topical immunosuppressive therapy.

Study Procedures

All patients must have signed the IRB-approved informed consent form before the initiation of any study-related evaluations. In addition, the institution's surgical consent form for invasive procedures will be signed.

Patients will have a complete history (including details of prior tumor therapy and concurrent non-malignant disease) and evaluation of all neurological symptoms within 2 weeks prior to the Day 0/Baseline procedure. Additionally, they will undergo a complete physical examination including a general examination and a neurological examination. Vital sign measurements and weight will be recorded and Karnofsky performance status score determined. Routine baseline laboratory testing will occur within two weeks of Day 0/Baseline procedure. These tests will be evaluated as baseline and for surgical clearance.

Finally, all subjects will undergo MRI of the brain with and without gadolinium administration within two weeks prior to the Day 0/Baseline procedure. Preliminary decisions regarding the eligibility of the subject for gene transfer therapy and the injections and/or procedures required for each subject will be decided based on the scan results.

Special Pretreatment Laboratory Assessments—All subjects will undergo special laboratory studies; Serum will be tested for anti-AdV5 antibody titer (ELISA); Additional serum will be tested for antibodies to specific cancer-related antigens (CRA) as well as cytokine profile using ELISA based MSD; Peripheral blood will be subject to flow cytometry (at the P.I. discretion); Serum pregnancy testing will be performed for females of childbearing potential; HIV-1 testing will be performed on all subjects; Hepatitis screening serology: hepatitis A, B [core antibody and surface antigen], C and D [Delta virus]; The following will be used to test serum, nasopharyngeal secretions, and urine for viral dissemination; and PCR for AdV DNA specific to Delta-24-RGD-4C and wild-type AdV.

Evaluation after Surgical Procedures—Within 36 hours after stereotactic biopsy, subjects will have a CT scan to assess for the presence of hematoma. While the subject is in the hospital, daily assessments will be conducted including short neurologic evaluation, Karnofsky performance status, vital sign measurements, determination of adverse signs or symptoms (clinical toxicity) and corticosteroid dose. On the day after all surgical procedures serum, urine, and nasopharyngeal secretions will be collected for monitoring virus dissemination and serum anti-AdV5 antibody titer determination. Within 24 hours after a procedure, subjects will have serum chemistry and hematological studies performed.

Evaluation after Craniotomy: An MRI of the brain with and without gadolinium will be performed for all subjects within 48 hours after craniotomy to assess the extent of resection and/or adverse effects of intramural injection.

Evaluation after Discharge: Patients can be discharged within 3 days of the procedure. Subjects will then be evaluated on day 28 (+/−2 days) and months 2 (+/−4 days), 3 (+/−4 days), and 4 (+/−4 days). Thereafter, follow-up will occur every two months (+/−7 days).

Follow-Up Assessments—During outpatient follow-up, each subject will undergo a complete physical and neurological examination, assessment of Karnofsky performance status, weight, vital sign measurements, determination of adverse events and an evaluation of steroid and concomitant medication use. An MRI of the brain, without and with gadolinium will be performed. Clinical safety labs will also be performed and samples of serum, urine, and nasopharyngeal secretions obtained for the shedding of systemic AdV. Finally, serum will be collected for anti-AdV5 antibody titer determination.

Specimen Analysis—All laboratory tests will be recorded on the appropriate CRF/worksheet record or electronic database. If unscheduled laboratory tests are performed based on clinical judgment, the results of these tests must also be recorded. Biopsy samples will be collected at the time of stereotactic biopsy. One portion of the biopsy specimen will be frozen in OCT media and another will be fixed in formalin and paraffin-embedded. Remaining biopsy samples will be flash-frozen. The tumor biopsy specimen will be analyzed for the following: H & E staining Specimens for Virus Dissemination Studies—Virus shedding and dissemination will be monitored at the indicated time points in nasopharyngeal secretions, urine and serum. Virus dissemination will be determined by PCR analysis of Delta-24-RGD-4C and wild-type AdV DNA, and culture as required, by noting the appearance of a CPE in a 293 cell-based assay following the addition of a subject sample. The 293 cell line provides the E1 protein in trans, thus supporting the replication of E1-deficient Delta-24-RGD-4C. Confirmation of CPE in select samples as adenoviral-derived will be determined by an ELISA-based assay for hexon protein. Samples will be tested for the presence of replication-competent adenovirus (RCA) by a CPE assay in a 293, cell line that does not provide the E1 proteins in trans.

Statistics

The primary objective of the phase I portion of this study is to determine the MTD for the combination of ipilimumab and Delta-24-RGD.

Phase I: Three patients are entered per dose level if no DLT is encountered in these 3 patients. If DLT is encountered, the cohort will be expanded to 6 patients. A maximum of 4 higher-dose cohorts are expected. If DLT is found at the starting dose, a maximum of two lower-dose cohorts can be explored. At least 6 patients will be treated at the recommended dose (or MTD-1) level. Hence, at least 9 and maximum 12 (two dose levels of virus escalation) patients will be treated in this portion. Patients treated at the MTD in the phase I portion of this study the number of subjects may be expanded for a preliminary Phase II component.

For the current single-stage trial, the hypotheses to be tested are H0: p<p0 versus H1: p>p1, where p is the probability of remaining alive and free from progression at 6 months. If the value of p0 (uninterestingly low response) will be set at 20% and p1 at 40%, a trial with 40 patients will give acceptable error rates for the hypothesis testing and precision for estimation (with alpha of 5% and power of 87%). The trial will be successful (null hypothesis rejected) when 13 or more patients are alive and progression-free at 6 months.

To assure adequate accrual of evaluable patients, the sample size will be increase by 10% (4 additional patients). Therefore a total of 44 patients will be enrolled.

Adverse Events Definitions

For this protocol, an adverse event (AE) is any untoward medical occurrence (e.g., sign, symptom, disease, syndrome, intercurrent illness, abnormal laboratory finding) that emerges or worsens relative to pre-injection baseline, during the administration or follow-up periods in a subject in a clinical investigation who has been administered an investigational product. The untoward medical occurrence may not necessarily have a causal relationship to the administration of the product. An AE can therefore be any unfavorable and/or unintended sign (including an abnormal laboratory result), symptom, or disease temporally associated with the use of a medicinal (investigational) product, whether or not related to the medicinal (investigational) product.

Common events/symptoms surrounding surgical procedures (e.g., pain, headache, standard blood pressure variations even if requiring antihypertensive medication, constipation, etc.) are within normal practice. Chronic, underlying, disease-related conditions that remain unchanged from baseline will not be considered as AEs. Exacerbations of underlying chronic conditions will be assessed for "seriousness" and if they are determined to be "serious" using the regulatory definition, will be reported as Serious Adverse Events (SAEs) on the appropriate forms.

Disability: A substantial disruption of a person's ability to conduct normal life functions.

Life-threatening adverse event: Any adverse drug experience that, in the view of the Investigator, places the subject at immediate risk of death from the reaction as it occurred, i.e., it does not include a reaction that, had it occurred in a more severe form might have caused death.

Unexpected adverse event: Any adverse drug experience, the specificity or severity of which is not consistent with the current Investigator Brochure; or if an Investigator Brochure is not required or available, the specificity or severity of which is not consistent with the risk information described in the general investigational plan or elsewhere in the current application, as amended. For example, under this definition, hepatic necrosis would be unexpected (by virtue of greater severity) if the Investigator Brochure or other product literature only referred to elevated hepatic enzymes or hepatitis. Similarly, cerebral vasculitis would be unexpected (by virtue of greater specificity) if the Investigator Brochure only listed cerebral vascular accidents. "Unexpected," as used in this definition, refers to an adverse drug experience that has not been previously observed (e.g., included in the Investigator Brochure) rather than from the perspective of such an experience not being anticipated from the pharmacological properties of the investigational product.

Associated with the use of the Investigational drug (Causality i.e., investigational study drug-related): There is a reasonable possibility that the experience may have been caused by the investigational agent. The Principal Investigator must review each adverse event and determine whether or not it is related to the investigational agent.

Serious Adverse Events—An adverse event occurring at any dose (including overdose) should be classified as SERIOUS if: (1) It resulted in death (i.e., the AE caused or led to death) (2) It was life-threatening (i.e., the AE placed the subject at immediate risk of death; it does not apply to an AE that hypothetically might have caused death if it were more severe) (3) It required or prolonged in-subject hospitalization (i.e., the AE required at least a 24-hour in-subject hospitalization or prolonged a hospitalization beyond the expected length of stay. Hospitalizations for elective medical/surgical procedures, scheduled treatments, or routine check-ups are not SAEs by this criterion) NOTE: The illness leading to the surgical or diagnostic procedure should be recorded as the AE or SAE, not the procedure itself. The procedure should be captured in the case narrative as part of the action taken in response to the illness.

It was disabling (i.e., the AE resulted in a substantial disruption of the subject's ability to carry out normal life functions)

It is a congenital anomaly/birth defect (i.e., an adverse outcome in a child or fetus of a subject exposed to the molecule or Investigational drug before conception or during pregnancy)

It does not meet any of the above serious criteria but may jeopardize the subject or may require medical or surgical intervention to prevent one of the outcomes listed above (i.e., is a significant or important medical event)

Note: The causality of the serious Adverse Events must also be determined given that the patients will be undergoing invasive surgical procedures that can in and of themselves lead to untoward events or poor outcomes. Only those events deemed possibly or probably related to the study drug will be considered as DLTs.

Serious adverse events will be captured from the time the patient signs consent until 30 days after the last dose of drug. Serious adverse events must be followed until clinical recovery is complete and laboratory test have returned to baseline, progression of the event has stabilized, or there has been acceptable resolution of the event.

Safety

All subjects who received any Delta-24-RGD-4C will be included in the safety analysis. Subjects who do not complete the study for whatever reason will have all available data up until the time of termination included in the safety analysis.

Adverse events will be summarized both overall and by dose group and tabulated by severity, relationship to Delta-24-RGD-4C and causality. The number and percentage of subjects experiencing adverse events will be tabulated by body system/preferred term both overall and by dose group. When an adverse event occurs more than once, the maximum severity and causality will be counted. Additionally, serious adverse events, adverse events that are possibly related to Delta-24-RGD-4C and adverse events that are unrelated to Delta-24-RGD-4C will be summarized separately. Concurrent illnesses will be listed and may be examined as possible confounders in the treatment response relationship. Concomitant medications and therapies will also be listed, as will previous treatments for malignant glioma. Any potentially related side effects will be analyzed. Data listings for all adverse events will be provided by subject.

Vital Sign Measurements—Vital sign measurements (blood pressure, heart rate, respiratory rate and temperature) results will be presented in data listings by visit, dose cohort and time interval, as appropriate. Summary data including univariate statistics of mean, standard error and median will also be presented.

Physical and Neurological Examinations/Performance Status—Physical findings will be summarized for each subject by visit and dose cohort. Longitudinal analyses of tumor-related neurological symptoms, performance status and weight may also be performed. Summary data including univariate statistics of mean, standard error and median will also be presented as appropriate. Time to disease progression and performance status less than 60 will also be evaluated.

MRI Scans—MRI scans will be evaluated by the Investigator and descriptive statistics will be reported. Results will be reported by subject visit and dose cohort and/or as appropriate.

Clinical Laboratory Results—Descriptive statistics for selected laboratory parameters will be presented overall and by subject by study day and dose group. For the same laboratory parameters, shift tables may be presented showing the number and percent of subjects with high, normal, and low (or normal/abnormal) laboratory results at baseline and post-Delta-24-RGD-4C injection by dose cohort. Group means, medians and standard errors will be calculated for the various laboratory parameters. Laboratory values will also be listed by subject and those exceeding a normal reference range will be flagged.

Efficacy

In this study, tumor response will be evaluated according to the MacDonald criteria (i.e. based on 2D measurements). In order to be comparable to previously published studies, the thresholds for partial response and progressive disease are 50% and 25%, respectively.

Tumor response will be the change in the size of brain lesions from baseline (within 4 days post Delta-24-RGD-4C administration) compared to 7 days post Delta-24-RGD-4C administration, 14, 21, 28 days, 2, 3 and 4 months and every two months thereafter following the last injection of virus. Changes in clinical disease status and steroid administration will be considered when reviewing changes in tumor size. Measurements obtained at these study time points will also be analyzed with consideration of any anti-tumor cancer therapies and timeframes administered. Brain tumor size will be calculated from MRI scans.

Subjects developing new rim enhancement in a previously non-enhancing area of the tumor bed (e.g. as is commonly seen on post-gadolinium T1-weighted MRI beginning several days after a gross total resection) will not be considered to have developed progressive disease unless the maximum diameter of the enhancing rim exceeds 10 mm or an area of nodular enhancement develops. In cases judged to be indeterminate by the PI, a stereotactic biopsy may be performed to determine if progression has occurred. Additionally, measurement of the areas of contrast enhancement will be determined and compared to the sum of the products of perpendicular diameters of all lesions using WHO criteria.

Time to disease progression will be calculated from the time of initiation of Delta-24-RGD-4C administration at tumor injection as well as resection until evidence of progression by clinical exam, performance status, and/or MRI. The Investigators will read the MRI, as needed, for the purpose of clinical assessment.

Descriptive statistics will be used to summarize survival data. According to Brem et al, the 6-month historical survival rate is 35% for subjects with recurrent malignant glioblastoma.

The percentage of subjects with improved or stable symptoms at the end of the injection of each study phase will also be summarized using 95% confidence intervals. The change in Karnofsky score will also be summarized with univariate statistics. Time to disease progression and KPS≤60 may also be evaluated by the Kaplan-Meier analytical method.

The invention claimed is:

1. A method for treating cancer in a patient having or suspected of having cancer comprising (a) administering a Delta-24 oncolytic adenovirus for a treatment period, (b) measuring the level of one or more Th1 biomarkers at a first time point and at a subsequent second time point, and (c) comparing the level of one or more Th1 biomarkers at the first time point and the second time point, wherein a decrease in one or more Th1 biomarkers at the second time point compared to the first time point indicates that the patient is non-responsive to treatment with the Delta-24 oncolytic adenovirus.

2. The method of claim 1, further comprising administering a Th1 stimulating agent to the patient with the Delta-24 oncolytic adenovirus if the patient is determined to be non-responsive.

3. The method of claim 1, wherein said Delta-24 oncolytic adenovirus is a Delta-24-RGD oncolytic adenovirus.

4. The method of claim 1, wherein the cancer is selected from the group consisting of primary brain cancer, metastatic brain cancer, lung cancer, breast cancer and prostate cancer.

5. The method of claim 4, wherein the cancer is low-grade or high-grade glioma.

6. The method of claim 5, wherein the cancer is high-grade glioma.

* * * * *

UNITED STATES PATENT AND TRADEMARK OFFICE
CERTIFICATE OF CORRECTION

| | | |
|---|---|---|
| PATENT NO. | : 10,238,698 B2 | Page 1 of 1 |
| APPLICATION NO. | : 14/374619 | |
| DATED | : March 26, 2019 | |
| INVENTOR(S) | : Frank Tufaro et al. | |

It is certified that error appears in the above-identified patent and that said Letters Patent is hereby corrected as shown below:

On the Title Page

Item (71) Applicant, delete "DNA TRIX, INC." and insert --DNATRIX, INC.-- therefor.

Item (71) Applicant, delete "MD ANDERSON CANCER CENTER, Houston, TX" and insert --BOARD OF REGENTS, THE UNIVERSITY OF TEXAS SYSTEM, Austin, TX-- therefor.

Signed and Sealed this
Thirtieth Day of July, 2019

Andrei Iancu
*Director of the United States Patent and Trademark Office*